(12) United States Patent
Andresen

(10) Patent No.: US 11,524,033 B2
(45) Date of Patent: Dec. 13, 2022

(54) THERAPEUTIC PROTEIN COMPOSITIONS AND METHODS OF MAKING AND USING THE SAME

(71) Applicant: Torque Therapeutics, Inc., Cambridge, MA (US)

(72) Inventor: Thomas L. Andresen, Cambridge, MA (US)

(73) Assignee: Torque Therapeutics, Inc., Cambridge, MA (US)

( * ) Notice: Subject to any disclaimer, the term of this patent is extended or adjusted under 35 U.S.C. 154(b) by 319 days.

(21) Appl. No.: 16/644,647

(22) PCT Filed: Sep. 5, 2018

(86) PCT No.: PCT/US2018/049596
§ 371 (c)(1),
(2) Date: Mar. 5, 2020

(87) PCT Pub. No.: WO2019/050978
PCT Pub. Date: Mar. 14, 2019

(65) Prior Publication Data
US 2021/0060065 A1    Mar. 4, 2021

Related U.S. Application Data

(60) Provisional application No. 62/657,218, filed on Apr. 13, 2018, provisional application No. 62/554,058, filed on Sep. 5, 2017.

(51) Int. Cl.
| | | |
|---|---|---|
| A61K 35/17 | (2015.01) | |
| C07K 14/54 | (2006.01) | |
| C12N 11/089 | (2020.01) | |

(52) U.S. Cl.
CPC .......... *A61K 35/17* (2013.01); *C07K 14/5443* (2013.01); *C12N 11/089* (2020.01)

(58) Field of Classification Search
CPC ...... A61K 38/19; C07K 14/54; C07K 14/525; C07K 14/555; C07K 14/5443
See application file for complete search history.

(56) References Cited

U.S. PATENT DOCUMENTS

| | | |
|---|---|---|
| 4,085,269 A | 4/1978 | Daumiller et al. |
| 4,549,010 A | 10/1985 | Sparer et al. |
| 5,409,698 A | 4/1995 | Anderson et al. |
| 5,453,491 A | 9/1995 | Takatsu et al. |
| 5,464,629 A | 11/1995 | Monshipouri et al. |
| 5,591,630 A | 1/1997 | Anderson et al. |
| 5,753,261 A | 5/1998 | Fernandez et al. |
| 5,773,006 A | 6/1998 | Anderson et al. |
| 5,994,126 A | 11/1999 | Steinman et al. |
| 6,001,973 A | 12/1999 | Strom et al. |
| 6,013,480 A | 1/2000 | Grabstein et al. |
| 6,077,519 A | 6/2000 | Storkus et al. |
| 6,117,982 A | 9/2000 | Chang |
| 6,120,751 A | 9/2000 | Unger |
| 6,143,292 A | 11/2000 | Slavin |
| 6,194,388 B1 | 2/2001 | Krieg et al. |
| 6,197,298 B1 | 3/2001 | Chang |
| 6,319,715 B1 | 11/2001 | Luo et al. |
| 6,475,483 B1 | 11/2002 | Steinman et al. |
| 6,479,286 B1 | 11/2002 | Nelson et al. |
| 6,521,431 B1 | 2/2003 | Kiser et al. |
| 6,544,549 B1 | 4/2003 | Boni et al. |
| 6,548,065 B1 | 4/2003 | Anderson et al. |
| 6,602,709 B1 | 8/2003 | Albert et al. |
| 6,613,582 B1 | 9/2003 | Koadek et al. |
| 6,627,460 B1 | 9/2003 | Lihme et al. |
| 6,685,911 B1 | 2/2004 | Zitvogel et al. |
| 6,693,086 B1 | 2/2004 | Dow et al. |
| 6,787,132 B1 | 9/2004 | Gabizon et al. |
| 6,887,974 B2 | 5/2005 | Pathak |
| 6,998,476 B2 | 2/2006 | Strom et al. |
| 7,011,812 B1 | 3/2006 | Griffiths et al. |
| 7,108,863 B2 | 9/2006 | Zalipsky et al. |
| 7,122,202 B2 | 10/2006 | Allen et al. |
| 7,132,243 B2 | 11/2006 | Matsushita et al. |
| 7,223,544 B2 | 5/2007 | Luo et al. |
| 7,258,853 B2 | 8/2007 | Strom et al. |
| 7,402,431 B2 | 7/2008 | Har-Noy |
| 7,531,572 B2 | 5/2009 | Dai et al. |
| 7,604,804 B2 | 10/2009 | Wang et al. |
| 7,648,962 B2 | 1/2010 | James et al. |
| 7,662,773 B2 | 2/2010 | James et al. |
| 7,858,081 B2 | 12/2010 | Bernard et al. |
| 7,959,934 B2 | 6/2011 | Klinman et al. |
| 7,988,963 B1 | 8/2011 | Banchereau et al. |
| 8,067,237 B2 | 11/2011 | Mooney et al. |
| 8,124,084 B2 | 2/2012 | Lefrancois et al. |
| 8,153,425 B2 | 4/2012 | Pogue-Caley et al. |
| 8,163,879 B2 | 4/2012 | Wong et al. |
| 8,192,485 B2 | 6/2012 | Ravi |
| 8,232,101 B2 | 7/2012 | Cai et al. |
| 8,252,916 B2 | 8/2012 | Simard et al. |
| 8,287,857 B2 | 10/2012 | Dudley et al. |
| 8,323,696 B2 | 12/2012 | Hubbell et al. |
| 8,349,558 B2 | 1/2013 | Fatho et al. |
| 8,349,901 B2 | 1/2013 | Satyam |
| 8,440,309 B2 | 5/2013 | Ohri et al. |

(Continued)

FOREIGN PATENT DOCUMENTS

| | | |
|---|---|---|
| CN | 103370339 A | 10/2013 |
| EP | 772624 A1 | 5/1997 |

(Continued)

OTHER PUBLICATIONS

International Search Report in International Application No. PCT/US2018/049596 dated Nov. 19, 2018.

(Continued)

*Primary Examiner* — Prema M Mertz
(74) *Attorney, Agent, or Firm* — Goodwin Procter LLP

(57) ABSTRACT

Disclosed herein are compositions and methods for preparation and use of protein therapeutics, and more particularly protein clusters or backpacks having a plurality of therapeutic protein monomers reversibly crossed-linked by biodegradable linkers.

10 Claims, 22 Drawing Sheets

(56) References Cited

U.S. PATENT DOCUMENTS

| | | |
|---|---|---|
| 8,546,137 B2 | 10/2013 | Cannon et al. |
| 8,562,965 B2 | 10/2013 | McManus et al. |
| 8,580,545 B2 | 11/2013 | Alferiev et al. |
| 8,586,359 B2 | 11/2013 | Kruse |
| 8,623,837 B2 | 1/2014 | Fewell et al. |
| 8,629,098 B2 | 1/2014 | Fahmy et al. |
| 8,666,674 B2 | 3/2014 | Kruse |
| 8,728,806 B2 | 5/2014 | Decker et al. |
| 8,741,642 B2 | 6/2014 | Manjili et al. |
| 8,747,869 B2 | 6/2014 | Irvine et al. |
| 8,771,664 B2 | 7/2014 | Berraondo Lopez et al. |
| 8,871,191 B2 | 10/2014 | Pavlakis et al. |
| 8,951,542 B2 | 2/2015 | Irvine et al. |
| 9,089,593 B2 | 7/2015 | Hasumi |
| 9,090,640 B2 | 7/2015 | Bierbach et al. |
| 9,149,432 B2 | 10/2015 | Irvine et al. |
| 9,149,535 B2 | 10/2015 | Xu et al. |
| 9,211,321 B2 | 12/2015 | Karlsson-Parra et al. |
| 9,283,184 B2 | 3/2016 | Irvine et al. |
| 9,303,080 B2 | 4/2016 | Felber et al. |
| 9,303,247 B2 | 4/2016 | Abe et al. |
| 9,339,462 B2 | 5/2016 | Irvine et al. |
| 9,352,028 B2 | 5/2016 | Barner et al. |
| 9,393,199 B2 | 7/2016 | Irvine et al. |
| 9,415,070 B2 | 8/2016 | Irvine et al. |
| 9,445,994 B2 | 9/2016 | Irvine et al. |
| 9,476,028 B2 | 10/2016 | Karlsson-Parra et al. |
| 9,487,800 B2 | 11/2016 | Schonfeld et al. |
| 9,504,643 B2 | 11/2016 | Tice et al. |
| 9,597,356 B2 | 3/2017 | Lee |
| 9,597,383 B2 | 3/2017 | Lee |
| 9,603,944 B2 | 3/2017 | Tang et al. |
| 9,616,020 B2 | 4/2017 | Irvine et al. |
| 9,629,877 B2 | 4/2017 | Cooper et al. |
| 9,724,393 B2 | 8/2017 | Conejo-Garcia et al. |
| 9,750,803 B2 | 9/2017 | Irvine et al. |
| 9,884,026 B2 | 2/2018 | Fahmy et al. |
| 9,907,753 B2 | 3/2018 | Irvine et al. |
| 10,226,510 B2 | 3/2019 | Tang et al. |
| 10,357,544 B2 | 7/2019 | Tang et al. |
| 10,588,942 B2 | 3/2020 | Tang et al. |
| 11,034,752 B2 | 6/2021 | Irvine et al. |
| 2001/0038859 A1 | 11/2001 | Maskiewicz et al. |
| 2001/0043929 A1 | 11/2001 | Zalipsky et al. |
| 2002/0001841 A1 | 1/2002 | Kaltoft et al. |
| 2002/0007173 A1 | 1/2002 | Kundig et al. |
| 2002/0085993 A1 | 7/2002 | Steinman et al. |
| 2002/0151004 A1 | 10/2002 | Craig |
| 2003/0054027 A1 | 3/2003 | Unger |
| 2003/0078339 A1 | 4/2003 | Kiser et al. |
| 2003/0082806 A1 | 5/2003 | Berenson et al. |
| 2003/0235619 A1 | 12/2003 | Allen et al. |
| 2004/0009149 A1 | 1/2004 | Altman et al. |
| 2004/0057935 A1 | 3/2004 | Yu et al. |
| 2004/0161413 A1 | 8/2004 | Laus et al. |
| 2004/0247624 A1 | 12/2004 | Unger et al. |
| 2005/0042298 A1 | 2/2005 | Pardridge et al. |
| 2005/0053667 A1 | 3/2005 | Irvine et al. |
| 2005/0130180 A1 | 6/2005 | Luo et al. |
| 2005/0214274 A1 | 9/2005 | Har-Noy |
| 2005/0214762 A1 | 9/2005 | Ross et al. |
| 2005/0266067 A1 | 12/2005 | Sengupta et al. |
| 2006/0046967 A1 | 3/2006 | Satyam |
| 2006/0057680 A1 | 3/2006 | Zheng et al. |
| 2006/0074009 A1 | 4/2006 | James et al. |
| 2006/0100163 A1 | 5/2006 | Orlando et al. |
| 2006/0104945 A1 | 5/2006 | Choi |
| 2006/0216269 A1 | 9/2006 | Hasumi |
| 2006/0236411 A1 | 10/2006 | Dreher et al. |
| 2006/0246524 A1 | 11/2006 | Bauer et al. |
| 2006/0257361 A1 | 11/2006 | Watanabe et al. |
| 2006/0263857 A1 | 11/2006 | Lefrancois et al. |
| 2006/0270030 A1 | 11/2006 | Voigt et al. |
| 2006/0275371 A1 | 12/2006 | Dai et al. |
| 2006/0286066 A1 | 12/2006 | Basran |
| 2007/0059318 A1 | 3/2007 | Balu-Iyer et al. |
| 2007/0148246 A1 | 6/2007 | Luo et al. |
| 2007/0248584 A1 | 10/2007 | Kent |
| 2007/0298093 A1 | 12/2007 | Konur et al. |
| 2008/0014144 A1 | 1/2008 | Saltzman et al. |
| 2008/0131415 A1 | 6/2008 | Riddell et al. |
| 2008/0171059 A1 | 7/2008 | Howland et al. |
| 2008/0207505 A1 | 8/2008 | James |
| 2008/0254537 A1 | 10/2008 | Boynton et al. |
| 2008/0267986 A1 | 10/2008 | Pfeifer et al. |
| 2008/0279836 A1 | 11/2008 | Har-Noy |
| 2009/0155204 A1 | 6/2009 | Beurskens et al. |
| 2010/0008930 A1 | 1/2010 | Stanulla et al. |
| 2010/0226973 A1 | 9/2010 | Fujii et al. |
| 2010/0255499 A1 | 10/2010 | Wender et al. |
| 2010/0266642 A1 | 10/2010 | Langer et al. |
| 2010/0310501 A1 | 12/2010 | Boyman et al. |
| 2010/0323018 A1 | 12/2010 | Irvine et al. |
| 2010/0324124 A1 | 12/2010 | Irvine et al. |
| 2011/0020388 A1 | 1/2011 | Zepp et al. |
| 2011/0081311 A1 | 4/2011 | Pavlakis et al. |
| 2011/0097346 A1 | 4/2011 | Rubiolo |
| 2011/0177156 A1 | 7/2011 | Szoka, Jr. et al. |
| 2011/0182870 A1 | 7/2011 | Leen et al. |
| 2011/0206740 A1 | 8/2011 | Karp et al. |
| 2011/0229529 A1 | 9/2011 | Irvine et al. |
| 2011/0229556 A1 | 9/2011 | Irvine et al. |
| 2011/0262963 A1 | 10/2011 | Geierstanger et al. |
| 2011/0293705 A1 | 12/2011 | Irvine et al. |
| 2012/0003295 A1 | 1/2012 | Jiang et al. |
| 2012/0121688 A1 | 5/2012 | Ishii et al. |
| 2012/0177724 A1 | 7/2012 | Irvine et al. |
| 2012/0276156 A1 | 11/2012 | Fraser et al. |
| 2012/0276157 A1 | 11/2012 | Fraser et al. |
| 2013/0045491 A1 | 2/2013 | Unutmaz |
| 2013/0203675 A1 | 8/2013 | DeSimone et al. |
| 2013/0302257 A1 | 11/2013 | Minko et al. |
| 2013/0302276 A1 | 11/2013 | Cantor et al. |
| 2013/0337471 A1 | 12/2013 | Nie et al. |
| 2014/0010793 A1 | 1/2014 | Lee |
| 2014/0010794 A1 | 1/2014 | Lee |
| 2014/0017170 A1 | 1/2014 | Irvine et al. |
| 2014/0081012 A1 | 3/2014 | DeSimone et al. |
| 2014/0134128 A1 | 5/2014 | Wong et al. |
| 2014/0212398 A1 | 7/2014 | Reisner et al. |
| 2014/0234351 A1 | 8/2014 | Bender et al. |
| 2014/0249319 A1 | 9/2014 | Nguyen |
| 2014/0255363 A1 | 9/2014 | Metelitsa et al. |
| 2014/0377334 A1 | 12/2014 | Irvine et al. |
| 2015/0017723 A1 | 1/2015 | Rooney et al. |
| 2015/0044258 A1 | 2/2015 | Knaus et al. |
| 2015/0110740 A1 | 4/2015 | Tang et al. |
| 2015/0152188 A1 | 6/2015 | Morisseau et al. |
| 2015/0272884 A1 | 10/2015 | Irvine et al. |
| 2015/0328333 A1 | 11/2015 | Fraser et al. |
| 2015/0335679 A1 | 11/2015 | Chiriva-Internati |
| 2015/0335762 A1 | 11/2015 | Fraser et al. |
| 2015/0359853 A1 | 12/2015 | Felber et al. |
| 2016/0030304 A1 | 2/2016 | Nagamatsu et al. |
| 2016/0038415 A1 | 2/2016 | Irvine et al. |
| 2016/0051698 A1 | 2/2016 | Schneck et al. |
| 2016/0068584 A1 | 3/2016 | Bechard et al. |
| 2016/0130318 A1 | 5/2016 | Jacques et al. |
| 2016/0175397 A1 | 6/2016 | Umana et al. |
| 2016/0256386 A1 | 9/2016 | Irvine et al. |
| 2016/0303046 A1 | 10/2016 | Irvine et al. |
| 2016/0375149 A1 | 12/2016 | Irvine et al. |
| 2017/0020963 A1 | 1/2017 | Qu et al. |
| 2017/0042998 A1 | 2/2017 | Slanetz |
| 2017/0049882 A1 | 2/2017 | Irvine et al. |
| 2017/0065726 A1 | 3/2017 | Huang |
| 2017/0080104 A1 | 3/2017 | Irvine et al. |
| 2017/0088597 A1 | 3/2017 | Wong et al. |
| 2017/0151281 A1 | 6/2017 | Wagner et al. |
| 2017/0196938 A1 | 7/2017 | Tang et al. |
| 2017/0216218 A1 | 8/2017 | Farokhzad et al. |
| 2017/0246253 A1 | 8/2017 | McCauley |
| 2017/0266114 A1 | 9/2017 | Irvine et al. |
| 2017/0333571 A1 | 11/2017 | Bhargava et al. |

(56) References Cited

U.S. PATENT DOCUMENTS

| | | |
|---|---|---|
| 2017/0335281 A1 | 11/2017 | Loew et al. |
| 2017/0342119 A1 | 11/2017 | Liu et al. |
| 2017/0349875 A1 | 12/2017 | Coelho et al. |
| 2018/0044391 A1 | 2/2018 | Gundram et al. |
| 2018/0110733 A1 | 4/2018 | Irvine et al. |
| 2018/0185473 A1 | 7/2018 | Irvine et al. |
| 2019/0083576 A1 | 3/2019 | Tang et al. |
| 2020/0131239 A1 | 4/2020 | Pucci et al. |
| 2020/0360482 A1 | 11/2020 | Tang et al. |
| 2021/0060065 A1 | 3/2021 | Andresen |
| 2021/0154313 A1 | 5/2021 | Andresen |
| 2021/0259968 A1 | 8/2021 | Irvine et al. |
| 2021/0269500 A1 | 9/2021 | Irvine et al. |
| 2022/0008526 A1 | 1/2022 | Andresen et al. |

FOREIGN PATENT DOCUMENTS

| | | |
|---|---|---|
| EP | 772624 B1 | 9/2000 |
| EP | 1111039 A1 | 6/2001 |
| EP | 831860 B1 | 10/2004 |
| EP | 1777294 A1 | 4/2007 |
| EP | 2025746 A1 | 2/2009 |
| EP | 2286831 A1 | 2/2011 |
| EP | 2388266 B1 | 11/2011 |
| EP | 2470644 B1 | 7/2012 |
| EP | 2537933 A1 | 12/2012 |
| EP | 2915569 A1 | 9/2015 |
| EP | 2956544 B1 | 12/2015 |
| EP | 3049114 A2 | 8/2016 |
| EP | 3064507 A1 | 9/2016 |
| EP | 3235830 A1 | 10/2017 |
| GB | 1112021 A | 5/1968 |
| JP | H3-244601 A | 10/1991 |
| JP | 2009149526 A | 7/2009 |
| JP | 2013173689 A | 9/2013 |
| WO | WO-1999042564 A2 | 8/1999 |
| WO | WO-2000000587 A1 | 1/2000 |
| WO | WO-2004032970 A2 | 4/2004 |
| WO | WO-2004035622 A2 | 4/2004 |
| WO | WO-2005044303 A1 | 5/2005 |
| WO | WO-2005079581 A1 | 9/2005 |
| WO | WO-2007001677 A2 | 1/2007 |
| WO | WO-2007034479 A2 | 3/2007 |
| WO | WO-2007046006 A2 | 4/2007 |
| WO | WO-2010059253 A2 | 5/2010 |
| WO | WO-2010104865 A2 | 9/2010 |
| WO | WO-2010147655 A2 | 12/2010 |
| WO | WO-2011017151 A2 | 2/2011 |
| WO | WO-2011063156 A2 | 5/2011 |
| WO | WO-2012040323 A2 | 3/2012 |
| WO | WO-2012112689 A1 | 8/2012 |
| WO | WO-2012142410 A2 | 10/2012 |
| WO | WO-2013012961 A2 | 1/2013 |
| WO | WO-2014204762 A1 | 12/2014 |
| WO | WO-2015018528 A1 | 2/2015 |
| WO | WO-2015018529 A1 | 2/2015 |
| WO | WO-2015024666 A1 | 2/2015 |
| WO | WO-2015048498 A2 | 4/2015 |
| WO | WO-2015120421 A1 | 8/2015 |
| WO | WO-2015131994 A1 | 9/2015 |
| WO | WO-2015153753 A2 | 10/2015 |
| WO | WO-2015176662 A1 | 11/2015 |
| WO | WO-2015189357 A1 | 12/2015 |
| WO | WO-2015188141 A9 | 1/2016 |
| WO | WO-2016018920 A1 | 2/2016 |
| WO | WO-2016105542 A2 | 6/2016 |
| WO | WO-2016142314 A1 | 9/2016 |
| WO | WO-2016145317 A1 | 9/2016 |
| WO | WO-2016146035 A1 | 9/2016 |
| WO | WO-2016154508 A1 | 9/2016 |
| WO | WO-2016154625 A1 | 9/2016 |
| WO | WO-2017027843 A1 | 2/2017 |
| WO | WO-2017046200 A1 | 3/2017 |
| WO | WO-2017087857 A1 | 5/2017 |
| WO | WO-2017218533 A1 | 12/2017 |
| WO | WO-2018075989 A1 | 4/2018 |
| WO | WO-2019050977 A1 | 3/2019 |
| WO | WO-2019050978 A1 | 3/2019 |
| WO | WO-2020102745 A1 | 5/2020 |
| WO | WO-2020205808 A1 | 10/2020 |

OTHER PUBLICATIONS

U.S. Appl. No. 16/309,443, Methods and Compositions for Promoting Immune Cell Function, filed Dec. 12, 2018.

U.S. Appl. No. 16/644,675, Reversible Linkers and Use Thereof, filed Mar. 5, 2020.

U.S. Appl. No. 17/293,995, Methods and Compositions for Cancer Immunotherapy, filed May 14, 2021.

U.S. Appl. No. 17/599,948, Immunotherapeutic Compositions and Use Thereof, filed Sep. 29, 2021.

Akagi, et al., "Development of vaccine adjuvants using polymeric nanoparticles and their potential applications for anti-HIV vaccine," Yakugaku Zasshi, vol. 127(2):307-317 (2007).

Akin, et al., Bacteria-mediated delivery of nanoparticles and cargo into cells. Nat Nanotechnol., vol. 2(7):441-9 (2007).

Allen, T. et al., "Anti-CD19-Targeted Liposomal Doxorubicin Improves the Therapeutic Efficacy in Murine B-Cell Lymphoma and Ameliorates the Toxicity of Liposomes with Varying Drug Release Rates," Clin Cancer Res., vol. 11(9):3567-3573 (2005).

Allen, T. et al., "Drug Delivery Systems: Entering the Mainstream. Science," vol. 303(5665):1818-1822 (2004).

Alving, C., "Liposomes as carriers of antigens and adjuvants," J Immunol Methods., vol. 140(1):1-13 (1991).

Alving, C. "Lipopolysaccharide, Lipid A, and Liposomes Containing Lipid A as Immunologic Adjuvants," Immunobiology, vol. 187(3-5):430-446 (1993).

Babensee, J. et al., "Differential levels of dendritic cell maturation on different biomaterials used in combination products," J Biomed Mater Res A., vol. 74(4):503-510. (2005).

Bal, et al., "Efficient induction of immune responses through intradermal vaccination with N-trimethyl chitosan containing antigen formulations," J Control Release, vol. 142(3):374-83 (2010).

Barral, P. et al., "B cell receptor-mediated uptake of CD1d-restricted antigen augments antibody responses by recruiting invariant NKT cell help in vivo," Proc Natl Acad Sci USA, vol. 105(24):8345-8350 (2008).

Baudino, L. et al., "Crucial Role of Aspartic Acid at Position 265 in the CH2 domain for murine IgG2a and IgG2b Fc-Associated effector functions," J Immunol., vol. 181(9):6664-6669 (2008).

Beisiegel, U. et al., "The LDL-receptor-related protein, LRP, is an apolipoprotein E-binding protein," Nature, vol. 341(6328):162-164 (1989).

Bennewitz, N. et al., "The effect of the physical form of poly(lactic-co-glycolic acid) carriers on the humoral immune response to co-delivered antigen," Biomaterials, vol. (16):2991-2999 (2005).

Bernard, et al., "Identification of an Interleukin-15α Receptor-Binding Site on Human Interleukin-15," J. Biol. Chem. 279(23):24313-24322 (2004).

Bershteyn, et al., "Versatile lipid-based vaccine carriers elicit CTL and antibody responses to surface-conjugated or encapsulated antigen," Keystone Symposium. Poster Presentation, A44. 1 page.

Bershteyn, A. et al., "Polymer-supported lipid shells, onions, and flowers," Soft Matter, vol. 4(9):1787-1791 (2008).

Bershteyn, A. et al. "Lipid-Coated Nano-and Microparticles for Vaccine Design," Materials Research Society fall meeting, 7 pages (2009).

Bershteyn, A. et al., "Robust IgG responses to nanograms of antigen using a biomimetic lipid-coated particle vaccine," J Control Release, vol. 157(3):354-65 (2012).

Besser, M. et al., "Clinical responses in a phase II study using adoptive transfer of short-term cultured tumor infiltration lymphocytes in metastatic melanoma patients," Clin Cancer Res, vol. 16(9):2646-2655 (2010).

Bhowmick, S. et al., "Comparison of liposome based antigen delivery systems for protection against Leishmania donovani," J Controlled Release, vol. 141(2):199-207 (2010).

(56) References Cited

OTHER PUBLICATIONS

Bottini, "Luminescent Silica Nanobeads: Characterization and Evaluation as Efficient Cytoplasmatic Transporters for T-Lymphocytes," JACS, vol. 129(25) pp. 7814-7823 (2007).
Brocchini, S. et al. "Disulfide bridge based PEGylation of proteins," Advanced Drug Delivery Reviews, vol. 60: 3-12 (2008).
Cai, Z. et al., "Encapsulated enhanced green fluorescence protein in silica nanoparticle for cellular imaging," Nanoscale, vol. 3(5):1974-1976 (2011).
Carson, et al., "Interleukin (IL) 15 is a novel cytokine that activates human natural killer cells via components of the IL-2 receptor," J. Exp. Med. 180(4):1395-1403 (1994).
Cashion, M. et al., "Biomimetic Design and Performance of Polymerizable Lipids," Accounts Chem. Res., vol. 42(8):1016-1025 (2009).
Chacon, M. et al., "Optimized preparation of poly d,l (lactic-glycolic) microspheres and nanoparticles for oral administration," Int J Pharm., vol. 141(1-2):81-91 (1996).
Chambers, E. et al., "Long Circulating Nanoparticles via Adhesion on Red Blood Cells: Mechanism and Extended Circulation," Exp Biol Med (Maywood), vol. 232(7):958-966 (2007).
Chambers, E. et al., "Prolonged circulation of large polymeric nanoparticles by non-covalent adsorption on erythrocytes," J Control Release, vol. 100(1): 111-119 (2004).
Chen, L. et al., "Characterization of PLGA microspheres for the controlled delivery of IL-1a for tumor immunotherapy," J Controlled Rei., vol. 43:261-272 (1997).
Chirifu, M. et al., "Crystal Structure of the IL-15-IL-15 Ralpha complex, a cytokine-receptor unit presented in trans," Nature Immunology, Published online Jul. 22, 2007, pp. 1001-1007 (2007).
Cho, E. et al., "Understanding the Role of Surface Charges in Cellular Adsorption versus Internalization by Selectively Removing Gold Nanoparticles on the Cell Surface with a I-2/KI Etchant," Nano Lett., vol. 9(3):1080-1084 (2009) (17 pages).
Clemente-Casares, X. et al., "Peptide-MHC-based nanovaccines for the treatment of autoimmunity: a "one size fits all" approach?" J Mol Med., vol. 89(8):733-742 (2011).
Cole, C. et al., "Tumor-targeted, systemic delivery of therapeutic viral vectors using hitchhiking on antigen-specific T cells," Nat Med., vol. 11(10):1073-1081 (2005).
Collins, D. et al., "Processing of exogenous liposome-encapsulated antigens in vivo generates class I MHC-restricted T cell responses," J Immunol., vol. 148(11):3336-3341 (1992).
Coronoa-Ortega, T. et al., "Characterization of cationic liposomes having IL-2 expressed on their external surface, and their affinity to cervical cancer cells expressing the IL-2 receptor," Journal of Drug Testing, vol. 17(7):496-501 (2009).
Cosman, et al., "Interleukin 15 and its Receptor," Ciba. Found. Symp. 195:221-233 (1995).
Davis, M. et al., "Nanoparticle therapeutics: an emerging treatment modality for cancer," Nat Rev Drug Discov., 7(9):771-782 (2008).
De La Pena, H. et al., "Artificial exosomes as tools for basic and clinical immunology," J Immunol. Methods, vol. 344(2):121-132(2009).
Demento, S. et al., "Inflammasome-activating nanoparticles as modular systems for optimizing vaccine efficacy," Vaccine, vol. 27(23):3013-3021 (2009) (17 pages).
Dinauer, N. et al., "Selective targeting of antibody-conjugated nanoparticles to leukemic cells and primary T-lymphocytes," Biomaterials, vol. 26(29):5898-5906 (2005).
Ding H., et al., "Bioconjugated PLGA-4-arm-PEG branched polymeric nanoparticles as novel tumor targeting carriers," Nanotechnology, vol. 22(16) 12 pages (2011).
Diwan, et al., Dose sparing of CpG oligodeoxynucleotide vaccine adjuvants by nanoparticle delivery. Curr Drug Deliv., 1(4):405-412 (2004).
Dou, H. et al., "Development of a macrophage-based nanoparticle platform for antiretroviral drug delivery," Blood, vol. 108(8):2827-2835 (2006).

Drummond, D. et al., "Optimizing Liposomes for Delivery of Chemotherapeutic Agents to solid tumors," Pharmacol Rev., vol. 51(4):691-743 (1991).
Dubikovskaya, E. et al., "Overcoming multidrug resistance of small-molecule therapeutics through conjugation with releasable octaarginine transporters," PNAS USA, vol. 105(34):12128-12133 (2008).
Dudley, M. et al., "Cancer Regression and Autoimmunity in Patients after Clonal Repopulation with Antitumor Lymphocytes," Science, vol. 298(5594):850-854 (2002) (10 pages).
Dudley, M. et al., "A phase I study of nonmyeloablative chemotherapy and adoptive transfer of autologous tumor antigen-specific T lymphocytes in patients with metastatic melanoma," J. Immunother.,—vol. 25(3):243-251 (2002) (17 pages).
Eck, W. et al., "Anti-CD4-targeted gold nanoparticles induce specific contrast enhancement of peripheral lymph nodes in X-ray computed tomography of live mice," Nano Lett., vol. 10(7):2318-2322 (2010).
Edwards, B. et al., "The Remarkable Flexibility of the Human Antibody Repertoire Isolation of Over One Thousand Different Antibodies to a Single Protein, BLyS," J Mol Biol., vol. 334(1):103-118 (2003).
El-Giamal, et al., "Über Einige Copolyurethane Ausgehend von Piperazin," Macromol. Chem. Phys. 177:2259-2269 (1976).
Elamanchili, P. et al., "Characterization of poly(D,L-lactic-co-glycolic acid) based nanoparticulate system for enhanced delivery of antigens to dendritic cells," Vaccine, vol. 22(19):2406-2412 (2004).
Endsley, A. et al., "Enhanced anti-HIV Efficacy of Indinavir after inclusion in CD4-targeted lipid nanoparticles," J Acquir Immune Defic Syndr., vol. 61(4):417-424 (2012).
Fahmy, T. et al., "A nanoscopic multivalent antigen-presenting carrier for sensitive detection and drug delivery to T cells," Nanomedicine, vol. 3(1):75-85 (2007).
Fahmy, T. et al., "Nanosystems for simultaneous imaging and drug delivery to T cells," AAPS J., vol. 9(2):E171-E180 (2007).
Festel et al., "Synthesis and Properties of Segmented Polyurethane Elastomers with Molecularly Uniform Hard Segments Based on 1,5-Naphthalene Diisocyanate and 1,4-Butandiol," Gaofenzi Tongbao 6:42-62 (2004).
Fifis, T. et al., "Size-Dependent Immunogenicity: Therapeutic and protective properties of nano-vaccines against tumors," J Immunol., vol. 173(5):3148-3154 (2004).
Fischer, H. et al., "Nanotoxicity: the growing need for in vivo study," Current Opin Biotechnol., vol. 18(6):565-571 (2007).
Friede, M. et al., "Induction of immune response against a short synthetic peptide antigen coupled to small neutral liposomes containing monophosphoryl lipid A," Mol Immunol., vol. 30(6):539-547 (1993).
Gabizon, A. et al., "Prolonged circulation time and enhanced accumulation in malignant exudates of doxorubicin encapsulated in polyethylene-glycol coated liposomes," Cancer Res., vol. 54(4):987-992 (1994).
Gao, W. et al., "Treg versus Th17 lymphocyte lineages are cross-regulated by LIF versus IL-6," Cell Cycle, vol. 8(9):1444-1450 (2009) (17 pages).
Gao, X. et al., "Lectin-conjugated PEG-PLA nanoparticles: preparation and brain delivery after intranasal administration," Biomaterials, vol. 27(18):3482-3490 (2006).
Garinot, M. et al., "PEGylated PLGA-based nanoparticles targeting M cells for oral vaccination," J Control Release, vol. 120(3):195-204 (2007).
Giri, et al., "Identification and Cloning of a Novel IL-15 Binding Protein that is Structurally Related to the a Chain of the IL-2 Receptor," EMBO J. 14(15):3654-3663 (1995).
Giri, et al., "Utilization of the β and γ Chains of the IL-2 Receptor by the Novel Cytokine IL-15," EMBO J. 13(12):2822-2830 (1994).
Grabstein, et al., "Cloning of a T Cell Growth Factor that Interacts with the β Chain of the Interleukin-2 Receptor," Science 264(5161):965-968 (1994).
Green, J. et al., "Combinatorial Modification of Degradable Polymers Enables Transfection of Human Cells Comparable to Adenovirus," Advanced Materials, vol. 19(19):2836-2842 (2007).

(56) References Cited

OTHER PUBLICATIONS

Gregoriadis, G. et al., "Liposomes as immunological adjuvants and vaccine carriers," J Control Release, vol. 41 (1-2):49-56 (1996).
Gunn, J. et al., "A Multimodal Targeting Nanoparticle for Selectively Labeling T Cells," SMALL, vol. 4(6):712-715 (2008) (10 pages).
Guo, et al., "Immunobiology of the IL-15/IL-15Rα Complex as an Antitumor and Antiviral Agent," Cytokine Growth Factor Revs. 38 (2017) (45 pages).
Hamdy, S. et al., "Enhanced antigen-specific primary $CD4_+$ and $CD8_+$ responses by codelivery of ovalbumin and toll-like receptor ligand monophosphoryl lipid A in poly(D,L-lactic-co-glycolic acid) nanoparticles," J Biomed Mater Res A., vol. 81(3):652-662 (2006).
Han, et al., "IL-15:IL-15 receptor alpha superagonist complex: High-Level Co-expression in Recombinant Mammalian Cells, Purification and Characterization," Cytokine 56(3):804-810 (2011).
Hedge, M. et al., "Tandem CAR T cells targeting HER2 and IL13Ra2 mitigate tumor antigen escape," J Clin Invest., vol. 126(8):3036-3052 (2016).
Heffernan, M. et al., "The stimulation of $CD8_+$ T cells by dendritic cells pulsed with polyketal microparticles containing ion-paired protein antigen and poly(inosinic acid)-poly(cytidylic acid)," Biomaterials, vol. 30(5):910-918 (2009).
Heit, et al., "Antigen co-encapsulated with adjuvants efficently drive protective T cell immunity," Eur J Immunol., 37(8):2063-74 (2007).
Hodi, F. et al., "Improved survival with ipilimumab in Patients with Metastatic Melanoma," N Engl. J. Med., vol. 363(8):711-723 (2010).
Hong, et al., "Configuration-dependent Presentation of Multivalent IL-15:IL-15Rα Enhances the Antigen-Specific T Cell Response and Anti-tumor Immunity," J. Biol. Chem. 291(17): 8931-8950 (2016) (20 pages).
Hori, Y. et al., "Injectable dendritic cell-carrying alginate gels for immunization and immunotherapy," Biomaterials, vol. 29(27):3671-3682 (2008).
Hori, Y. et al., "Engulfing tumors with synthetic extracellular matrices for cancer immunotherapy," Biomaterials, vol. 30 (35):6757-6767 (2009) (20 pages).
Hotz, J. et al., "Vesicle-templated polymer hollow spheres," Langmuir, vol. 14(5):1031-1036 (1998).
Hsu, C. et al., "Cytokine-independent growth and clonal expansion of a primary human $CD8_+$ T-cell clone following retroviral transduction with the IL-15 gene," Blood, vol. 109(12):5168-5177 (2007).
Hu, Y. et al., "Cytosolic delivery of membrane-impermeable molecules in dendritic cells using pH-responsive core-shell nanoparticles," Nano Lett., vol. 7(10):3056-3064 (2007).
Hurton, et al., "Tethered IL-15 Augments Antitumor Activity and Promotes a Stem-Cell Memory Subset in Tumor-specific T cells," PNAS 113(48):E7788-E7797 (2016).
Immordino, M. et al., "Stealth liposomes: review of the basic science, rationale, and clinical applications, existing and potential," Int J Nanomedicine, vol. 1(3):297-315 (2006).
International Preliminary Report on Patentability in International Application No. PCT/US2018/049596 dated Dec. 21, 2020.
International Search Report in International Application No. PCT/US2017/037249 dated Sep. 19, 2017.
Irvine et al., "Combining cell therapy with nanotechnology for enhanced cancer immunotherapy." 16th International Symposium on Recent Advances in Drug Delivery Systems. Salt Lake City, UT, Abstract (2013) (2 pages).
Irvine, D.J. "Engineering nanomaterials as vaccine adjuvants and agents for cancer immunotherapy," Seminar at Scripps Res Institute, 9 pages (2011).
Irvine, D.J. "Engineering nanoparticle delivery for vaccines and immunotherapy," Nanotechnology in Infectious Disease Meeting, Atlanta, GA, 33 pages (2010).
Jain, N.K., et al., "Targeted drug delivery to macrophages," Expert Opin Drug Deliv., vol. 10(3):353-367 (2013).
Jeong, J. et al., "Enhanced adjuvantic property of polymerized liposome as compared to a phospholipid liposome," J Biotechnol., vol. 94(3):255-263 (2002).

Jiang, W. et al., "Biodegradable poly(lactic-co-glycolic acid) microparticles for injectable delivery of vaccine antigens," Adv Drug Deliv Rev., vol. 57(3):391-410 (2005).
Johnson, RM., "The kinetics of Resealing of Washed Erythrocyte Ghosts," J. Membr. Biol., vol. 22 (3-4):231-253 (1975).
Jones, DT "Critically assessing the state-of-the-art in protein structure prediction," Pharmacogenomics Journal, vol. 1(2):126-134 (2001).
Jones, L. et al., "Releasable Luciferin-Transporter Conjugates: tools for the real-time analysis of cellular uptake and release," J Am Chern Soc., vol. 128(20):6526-6527 (2006).
June, C. "Principles of adoptive T cell cancer therapy," J Clin Invest., vol. 117(5):1204-1212 (2007).
Kaiser-Schulz, G. et al., "Polylactide-coglycolide microspheres co-encapsulating recombinant tandem prion protein with CpG-oligonucleotide break self-tolerance to prion protein in wild-type mice and induce CD4 and CD8 T cell responses," J Immunol., vol. 179(5):2797-2807 (2007).
Kalos, M. "Biomarkers in T cell therapy clinical trials," J Trans Med., vol. 9(138) 9 pages (2011).
Kalos, M. et al., "T cells with chimeric antigen receptors have potent antitumor effects and can establish memory in patients with advanced leukemia," Sci Trans Med., vol. 3(95), 12 pages (2011).
Kerkar, S. et al., "Tumor-specific $CD8_+$ T cells expressing interleukin-12 eradicate established cancers in lymphodepleted hosts," Cancer Res., vol. 70(17):6725-6734 (2010).
Kim, et al., "IL-15 Superagonist /IL-15RαSushi-Fc fusion complex (IL-15SA/IL-15αSu-Fc; ALT-803) markedly enhances specific subpopulations of NK and memory $CD8_+$ T cells, and mediates potent anti-tumor activity against murine breast and colon carcinomas," Oncotarget 7(13):16130-16145 (2016).
Kirby, C. et al., "Dehydration-rehydration vesicles: a simple method for high yield drug entrapment in liposomes," Nat Biotechnol., vol. 2(11):979-984 (1984).
Kirpotin, D. et al., "Antibody targeting of long-circulating lipidic nanoparticles does not increase tumor localization but does increase internalization in animal models," Cancer Res., vol. 66(13):6732-6740 (2006).
Klebanoff, C. et al., "Sinks, suppressors and antigen presenters: how lymphodepletion enhances T cell-mediated tumor immunotherapy," Trends Immunol., vol. 26(2): 111-117 (2005) (14 pages).
Kobayashi, H. et al., "Phase I/II study of adoptive transfer of γδ T cells in combination with zoledronic acid and IL-2 to patients with advanced renal cell carcinoma," Cancer Immunol. Immunother, vol. 60(8):1075-1084 (2011).
Kochenderfer, J. et al., "Adoptive transfer of syngeneic T cells transduced with a chimeric antigen receptor that recognizes murine CD19 can eradicate lymphoma and normal B cells," Blood, vol. 116 (19):3875-3886 (2010).
Konigsberg, P.J. "The development of IL-2 conjugated liposomes for therapeutic purposes," Biochimica Biophysica Acta, vol. 1370(2):243-251 (1998).
Konrad, M. et al., "Pharmacokinetics of recombinant interleukin 2 in humans," Cancer Res., vol. 50(7):2009-2017 (1990).
Krishna, N. et al., "Genetic Determinants of Rous Sarcoma Virus Particle Size," Journal of Virology, vol. 72 (1):564-577 (1998).
Kudchodkar, S. et al., "Improving CAR T Cell Efficacy for Solid Tumors by Nanogel-Based Delivery of Immunomodulatory Proteins," Molecular Therapy: The Journal of The American Society of Gene Therapy, vol. 23(SI):S207-S207 (2015) (1page).
Kwon, et al., In vivo targeting of dendritic cells for activation of cellular immunity using vaccine carriers based on pH-responsive microparticles. Proc Natl Acad Sci USA., 102(51):18264-8 (2005).
Kwong, B. et al., "Localized immunotherapy via liposome-anchored Anti-CD137 $_+$ IL-2 prevents lethal toxicity and elicits local and systemic antitumor immunity," Cancer Res., vol. 73(5):1547-1558 (2013).
Kwong, B. et al., "Induction of potent anti-tumor responses while eliminating systemic side effects via liposome-anchored combinatorial immunotherapy," Biomaterials, vol. 32(22):5134-5147 (2011).
Kwong, B., "Liposome-anchored local delivery of immunomodulatory agents for tumor therapy," Biological Engineering, Massachusetts Institute of Technology, 175 pages (2012).

(56) References Cited

OTHER PUBLICATIONS

Lachman, L. et al., "Cytokine-containing liposomes as vaccine adjuvants," Eur Cytokine Netw., vol. 7(4):693-698 (1996).
Lateef, S. et al., "An Improved Protocol for Coupling Synthetic Peptides to Carrier Proteins for Antibody Production using DMF to Solubilize Peptides," J Biomolecular Techniques, vol. 18:173-176 (2007).
Lavelle, E.C. et al., "The stability and immunogenicity of a protein antigen encapsulated in biodegradable microparticles based on blends of lactide polymers and polyethylene glycol.," Vaccine, vol. 17(6):512-529 (1999).
Lee, J. et al., "Multifunctional nanoarchitectures from DNA-based ABC monomers," Nat Nanotechnol. vol. 4(7):430-436 (2009) (8 pages).
Leland, P. et al., "Cancer Chemotherapy-Ribonucleases to the Rescue," Chem Biol. vol. 8(5):405-413 (2001) (16 pages).
Li, J. et al., "Purification of melanoma reactive T cell by using a monocyte-based solid phase T-cell selection system for adoptive therapy," J Immunother., vol. 31(1):81-88 (2008).
Li, Y. et al., "PEGylated PLGA nanoparticles as protein carriers: synthesis, preparation and biodistribution in rats," J Control Release, vol. 71(2):203-211 (2001).
Lloyd, C. et al., "Modelling the human immune response: performance of a 1011 human antibody repertoire against a broad panel of therapeutically relevant antigens," Protein Engineering, Design & Selection, vol. 22(3):159-168 (2009).
Lodish, H. et al., "Chemical Foundations," In: Molecular Cell Biology, Fifth Eds. Chapter 2 (2004) (19 pages).
Lowenthal, J. et al., "Similarities between interleukin-2 receptor number and affinity on activated B and T lymphocytes," Nature, vol. 315(20):669-672 (1985).
Lowenthal, J. et al., "High and low affinity IL 2 receptors: analysis by IL 2 dissociation rate and reactivity with monoclonal antireceptor antibody PC61," J Immunol., vol. 135(6):3988-3994 (1985).
Lu, W. et al., "Cationic albumin-conjugated pegylated nanoparticles as novel drug carrier for brain delivery," J Control Release, vol. 107(3):428-448 (2005).
Lutsiak, M. et al., "Analysis of poly(D,L-lactic-co-glycolic acid) nanosphere uptake by human dendritic cells and macrophages in vitro," Pharm Res., vol. 19(10):1480-1487 (2002).
MacLaughlin, C.M., et al., "Polymer-coated surface enhanced Raman scattering (SERS) gold nanoparticles for multiplexed labeling of chronic lymphocytic leukemia cells," Frontiers in Biological Detection: From Nanosensors to Systems IV, SPIE, vol. 8212(1):1-11 (2012).
Maeda, H. et al., "Tumor vascular permeability and the EPR effect in macromolecular therapeutics: a review.," J Control Release, vol. 65(1-2):271-284 (2000).
Maloy, K. et al., "Induction of mucosal and systemic immune responses by immunization with ovalbumin entrapped in poly(lactide-co-glycolide) microparticles," Immunology, vol. 81(4):661-667 (1994).
Markley, J. et al., "IL-7 and IL-21 are superior to IL-2 and IL-15 in promoting human T cell-mediated rejection of systemic lymphoma in immunodeficient mice," Blood, vol. 115(17):3508-3519 (2010).
Martinez Gomez, J. et al., "A protective allergy vaccine based on CpG-and protamine-containing PLGA microparticles," Pharm Res., vol. 24(10):1927-1935 (2007).
Matsumoto, N. et al., "Synthesis of Nanogel-Protein Conjugates," Polym Chem., vol. 4(8):2464-2469 (2013) (15 pages).
Matsumura, Y. et al., "A new concept for macromolecular therapeutics in cancer chemotherapy: mechanism of tumoritropic accumulation of proteins and the antitumor agent smancs," Cancer Res., vol. 46(12 Pt 1):6387-6392 (1986).
McInnis et al., "A Fully Closed, High Efficiency Manufacturing Technology Platform for the Production of T Cell Therapies Targeting Multiple Tumor Antigens," Society for Immunotherapy for Cancer (SITC) 33rd Annual Meeting. Nov. 10, 2018 (1 page).
McKee, A. et al., "How do adjuvants work? Important considerations for new generation adjuvants," Immunity, vol. 27(5):687-690 (2007).
Mellman, I. et al., "Cancer immunotherapy comes of age," Nature, vol. 480(7378):480-489 (2011).
Meng, F. et al., "Reduction-sensitive polymers and bioconjugates for biomedical applications," Biomaterials, vol. 30:2180-2198 (2009) (19 pages).
Minami, Y. et al., "The IL-2 receptor complex: its structure, function, and target genes," Annu Rev. Immunol., vol. 11:245-268 (1993).
Moghimi, S. et al., "Long-circulating and target-specific nanoparticles: theory to practice," Pharmacol Rev., vol. 53(2):283-318 (2001).
Mohammed, A. et al., "Lyophilisation and sterilisation of liposomal vaccines to produce stable and sterile products," Methods, vol. 40(1):30-38 (2006).
Moon, J. et al., "Engineering nano-and microparticles to tune immunity," Adv Mater., vol. 24(28):3724-3746 (2012) (39 pages).
Moon, J. et al., "Enhancing humoral responses to a malaria antigen with nanoparticle vaccines that expand Tfh cells and promote germinal center induction," Proc Natl Acad Sci USA., vol. 109(4):1080-1085 (2012).
Moon, J. et al., "Interbilayer-crosslinked multilamellar vesicles as synthetic vaccines for potent humoral and cellular immune responses," Nat Mater., vol. 10(3):243-251 (2011) (21 pages).
Moore, A. et al., "Tracking the recruitment of diabetogenic $CD8_+$ T-cells to the pancreas in real time," Diabetes, vol. 53(6):1459-1466 (2004).
Morgan, R. et al., "Cancer regression in patients after transfer of genetically engineered lymphocytes," Science, vol. 314(5796):126-129 (2006) (10 pages).
Mortensen, M.W. et al., "Next generation adoptive immunotherapy—human T cells as carriers of therapeutic nanoparticles," J Nanosci Nanotechnol., vol. 7(12):4575-4580 (2007).
Mortier et al., "Soluble Interleukin-15 Receptor α (IL-15Rα)-sushi as a Selective and Potent Agonist of IL-15 Action through IL-15Rβ/γ; Hyperagonist IL-15.IL-15Rα Fusion Proteins," J. Biol. Chem. 281(3):1612-1619 (2006).
Mundargi, R. et al., "Nano/micro technologies for delivering macromolecular therapeutics using poly(D,L-lactide-co-glycolide) and its derivatives," J Control Release., vol. 125(3):193-209 (2008).
Murcia et al., "Design of quantum dot-conjugated lipids for long-term, high-speed tracking experiments on cell surfaces," J Am Chem Soc., vol. 130(45): 15054-62 (2008) (21 pages).
Murphy, R. et al., "Endosome pH measured in single cells by dual fluorescence flow cytometry: rapid acidification of insulin to pH 6," J Cell Biol., vol. 98(5):1757-1762 (1984).
Nguyen, D. et al., "Disulfide-crosslinked heparin-pluronic nanogels as a redox-sensitive nanocarrier for intracellular protein deliver," J. Bioactive and Compatible Polymers, vol. 26(3):287-300 (2011).
Nuhn, et al., "pH-Degradable Imidazoquinoline-Ligated Nanogels for Lymph Node-Focused Immune Activation," PNAS 113(29):8098-8103 (2016).
O'Hagan, D. et al., "Induction of potent immune responses by cationic microparticles with adsorbed human immunodeficiency virus DNA vaccines," J Virol., vol. 75(19):9037-9043 (2001).
O'Hagan, D. et al., "Microparticles as potentially orally active immunological adjuvants," Vaccine, vol. 7(5):421-424 (1989).
O'Hagan, D. et al., "Microparticles as vaccine adjuvants and delivery systems," Expert Rev Vaccines, vol. 2(2):269-283 (2003).
O'Hagan, D. et al., "Poly(lactide-co-glycolide) microparticles for the development of single-dose controlled-release vaccines," Adv Drug Deliv. Rev., vol. 32(3):225-246 (1987).
Overwijk, W. et al., "Tumor regression and autoimmunity after reversal of a functionally tolerant state of self-reactive $CD8_+$ T cells," J Exp Med., vol. 198(4):569-580 (2003).
Owens, D. et al., "Opsonization, biodistribution, and pharmacokinetics of polymeric nanoparticles.," Int J Pharm. , vol. 307(1):93-102 (2006).
Park, J. et al., "Anti-HER2 immunoliposomes: enhanced efficacy attributable to targeted delivery," Clin Cancer Res., vol. 8(4):1172-1181 (2002).
Park, J. et al., "Modulation of $CD4_+$ T lymphocyte lineage outcomes with targeted, nanoparticle-mediated cytokine delivery," Mol Pharm., vol. 8(1):143-152 (2011) (16 pages).

(56) References Cited

OTHER PUBLICATIONS

Paulos, C. et al., "Toll-like receptors in tumor immunotherapy," Clin Cancer Res., vol. 13(18 Pt 1):5280-5289 (2007).
Perche, F. et al., "Recent trends in multifunctional liposomal nanocarriers for enhanced tumor targeting," J Drug Deliv., vol. 2013, Article ID. 705265, 32 pages (2013).
Perdreau, et al., "Different Dynamics of IL-15R Activation Following IL-15 cis- or trans-Presentation," Eur. Cytokine Netw. 21(4):297-307 (2010).
Perica, K. et al., "Magnetic field-induced T cell receptor clustering by nanoparticles enhances T cell activation and stimulates antitumor activity," ACS Nano., vol. 8(3):2252-2260 (2013).
Petros, R. et al., "Strategies in the design of nanoparticles for therapeutic applications," Nature Reviews, vol. 9:615-627 (2010).
Phillips, N.et al., "Immunoliposome targeting to murine $CD4_+$ leucocytes is dependent on immune status," J Immunol., vol. 152(6):3168-3174 (1993).
Plunkett, K. et al., "Chymotrypsin Responsive Hydrogel: Application of a Disulfide Exchange Protocol for the Preparation of Methacrylamide Containing Peptides," Biomacromolecules, vol. 6(2):632-637 (2005).
Popescu, M. et al., "A novel proteoliposomal vaccine elicits potent antitumor immunity in mice," Blood, vol. 109(12):5407-5410 (2007).
Press, O. et al., "Retention of B-Cell-Specific Monoclonal Antibodies by Human Lymphoma Cells," Blood, vol. 83(5):1390-1397 (1994).
Prieto, P. et al., "Enrichment of $CD8_+$ cells from melanoma tumor-infiltrating lymphocyte cultures reveals tumor reactivity for use in adoptive cell therapy," J Immunother., vol. 33(5):547-556 (2010).
Prokop, A. et al., "Hydrogel-based colloidal polymeric system for protein and drug delivery: physical and chemical characterization, permeability control and applications," Advances in Polymer Science, vol. 160:119-173 (2002).
Puri, A. et al., "HER2-specific affibody-conjugated thermosensitive liposomes (Affisomes) for improved delivery of anticancer agents," J Liposome Res., vol. 18(4):293-307 (2008) (20 pages).
Qiao, J. et al., "Purging metastases in lymphoid organs using a combination of antigen-nonspecific adoptive T cell therapy, oncolytic virotherapy and immunotherapy," Nat Med, vol. 14(1):37-44 (2008).
Rangel-Corona, R. et al., "Cationic liposomes bearing IL-2 on their external surface induced mice leukocytes to kill human cervical cancer cells in vitro, and significantly reduced tumor burden in immunodepressed mice," J Drug Target., vol. 19(2):79-85 (2011).
Reddy, R. et al., "In vivo cytotoxic T lymphocyte induction with soluble proteins administered in liposomes," J Immunol., vol. 148(5):1585-1589 (1992).
Reddy, S. et al., "Exploiting lymphatic transport and complement activation in nanoparticle vaccines," Nature Biotechnology, vol. 25(10):1159-1164 (2007).
Reed, S. et al., "New horizons in adjuvants for vaccine development," Trends Immunol., vol. 30(1):23-32 (2009).
Restifo, N. et al., "Adoptive immunotherapy for cancer: harnessing the T cell response," Nat Rev. Immunol., vol. 12(4):269-281(2012).
Ring, A. et al., "Mechanistic and structural insight into the functional dichotomy between IL-2 and IL-15," Nature Immunology, vol. 13(12):1187-1197 (2012).
Rosenberg, S. et al., "Adoptive cell transfer: a clinical path to effective cancer immunotherapy," Nat Rev Cancer, vol. 8(4):299-308 (2008) (22 pages).
Rubin, B. et al., "Fractionation of T cell subsets on Ig anti-Ig columns Isolation of helper T cells from nonresponder mice, demonstration of antigen-specific T suppressor cells, and selection of CD-3 negative variants of Jurkat T cells," Cellular Immunology, vol. 119(2):327-340. (1989).
Rubinstein, et al., "Converting IL-15 to a Superagonist by Binding to Soluble IL-15Rα," PNAS 103(24):9166-9171 (2006).
Rubinstein, M. et al., "Ex vivo IL-12-priming during $CD8_+$ T cell activation dramatically improves adoptive T cell transfer anti-tumor efficacy in a lymphodepleted host," J Am Coll Surg., vol. 214(4):700-708 (2012) (13 pages).
Schlosser, et al., "TLR ligands and antigen need to be coencapsulated into the same biodegradable microsphere for the generation of potent cytotoxic T lymphocyte responses," Vaccine, vol. 26(13):1626-1637 (2008).
Scott, E. et al., "Protein adsorption and cell adhesion on nanoscale bioactive coatings formed from poly(ethylene glycol) and albumin microgels," Biomaterials, vol. 29(34):4481-4493 (2008).
Seeman, P. et al., "Transient Holes in the Erythrocyte Membrane During Hypotonic Hemolysis and Stable Holes in the Membrane After Lysis by Saponin and Lysolecithin," The Rockefeller University, J Cell Biol., vol. 32(1):55-70 (1967).
Shi, et al., "Dendrimer-functionalized shell-crosslinked iron oxide nanoparticles for in-vivo magnetic resonance imaging of tumors.," Advanced Materials, vol. 20(9):1671-1678 (2008).
Shilyansky, J. et al., "T-cell receptor usage by melanoma-specific clonal and highly oligoclonal tumor-infiltrating lymphocyte lines," PNAS, vol. 91:2829-2833 (1994).
Shimizu, T. et al., "Nanogel DDS enables sustained release of IL-12 for tumor immunotherapy," BBRC, vol. 367(2):330-335 (2008).
Singh, et al., "Anionic microparticles are a potent delivery system for recombinant antigens from Neisseria meningitidis serotype B," J Pharm Sci., vol. 93(2):273-282 (2003).
Singh, et al., "Cationic microparticles: A potent delivery system for DNA vaccines," Proc Natl Acad Sci USA., vol. 97(2):811-816 (2007).
Singh, et al., "Charged polylactide co-glycolide microparticles as antigen delivery systems," Expert Opin Biol Ther., vol. 4(4):483-491 (2004).
Singh, et al., "Immunogenicity and protection in small-animal models with controlled-release tetanus toxoid microparticles as a single-dose vaccine," Infect Immun., vol. 65(5):1716-1721 (1997).
Singh, et al., "Nanoparticles and microparticles as vaccine-delivery systems," Expert Rev Vaccines., vol. 6(5):797-808 (2007).
Singh, et al., "Polylactide-co-glycolide microparticles with surface adsorbed antigens as vaccine delivery systems," Curr Drug Deliv., vol. 3(1):115-120 (2006).
Singh, et al., "Recent advances in vaccine adjuvants," Pharm Res., vol. 19(6):715-728 (2002).
Singh, S. et al., "Embedding of Active Proteins and Living Cells in Redox-Sensitive Hydro-gels and Nanogels through Enzymatic Cross-Linking," Angew. Chem. tnt. Ed., vol. 52:3000-3003 (2013).
Society for Experimental Biology and Medicine, Nanoparticles hitchhike on red blood cells for drug delivery. RxPG News. Jun. 27, 2007. Last retrieved from http://www.rxpgnews.com/drugdelivery/Nanoparticles-hitchhike-on-red-blood-cells-a-potential-new-method-for-drug-delivery_40324.shtml (2012) (3 pages).
Steers, N. et al.,"Liposome-encapsulated HIV-1 Gag p24 containing lipid A induces effector $CD4_+$ T-cells, memory $CD8_+$ T-cells, and pro-inflammatory cytokines," Vaccine, vol. 27(49):6939-6949 (2009).
Steinfeld, U., et al., "T lymphocytes as potential therapeutic drug carrier for cancer treatment," Int. J. Pharm., vol. 311:229-236 (2006).
Stephan, et al., "Enhancing Cell therapies from the Outside in: Cell Surface Engineering Using Synthetic Nanomaterials," Nano Today., vol. 6(3):309-325 (2011) (28 pages).
Stephan, et al., "Synapse-directed delivery of immunomodulators using T-cell-conjugated nanoparticles," Biomaterials, vol. 33(23):5776-5787 (2012) (25 pages).
Stephan, et al., "T cell-encoded CD80 and 4-1BBL induce auto- and transcostimulation, resulting in potent tumor rejection," Nat Med., vol. 13(12): 1440-1449 (2007).
Stephan, M. et al., "Therapeutic cell engineering with surface-conjugated synthetic nanoparticles," Nat Med., vol. 16(9):1035-1041 (2010) (17 pages).
Stoklasek, et al., "Combined IL-15/IL-15Rα Immunotherapy Maximizes IL-15 Activity in vitro," J. Immunol. 177:6072-6080 (2006).
Stonier, et al., "Trans-presentation: A Novel Mechanism Regulating IL-15 Delivery and Responses," Immunol. Lett. 127(2) (2010) (16 pages).
Swiston, et al., "Surface functionalization of living cells with multilayer patches," Nano Lett., vol. 8(12):4446-4453 (2008).

(56) References Cited

OTHER PUBLICATIONS

Takasaki, et al., "Micelles as intermediates in the preparation of protein-liposome conjugates," Bioconjug Chem., vol. 17(2):438-450 (2006).
Tan, H. et al., "PEG-urokinase nanogels with enhanced stability and controllable bioactivity," Soft Matter, vol. 8:2644-2650 (2012).
Tang, L. et al., "Abstract 2792: Engineering T lymphocytes with protein nanogels for cancer immunotherapy," Cancer Research, AACR Annual Meeting, 2 pages (2014).
Tang, L. et al., "Enhancing T cell therapy through TCR-signaling-responsive nanoparticle drug delivery," Nat Biotechnol. 36(8): 707-716 (2018) (29 pages).
Tangney, M. et al., "The use of Listeria monocytogenes as a DNA delivery vector for cancer gene therapy," Bioeng Bugs., vol. 1(4):284-287 (2010).
Tanna, et al., "Critical Testing and Parameters for Consideration When Manufacturing and Evaluating Tumor-Associated Antigen-Specific T Cells," Cytotherapy 21(3):278-288 (2019).
Topalian, et al., "Expansion of human tumor infiltrating lymphocytes for use in immunotherapy trials", J Immunol Methods, 102(1):127-41 (1987).
Topalian, S. et al., "Safety, activity, and immune correlates of anti-PD-1 antibody in cancer," N Engl. J Med., vol. 366(26):2443-2454 (2012) (19 pages).
Torchilin, "Recent advances with liposomes as pharmaceutical carriers," Nat Rev Drug Disc., vol. 4(2):145-160 (2005).
Tosatto, S.C., et al., "Large-scale prediction of protein structure and function from sequence," Current Pharmaceutical Design, vol. 12:2067-2086 (2006).
Trevaskis, NL et al., "Targeted drug delivery to lymphocytes: a route to site-specific immunomodulation," Mol Pharm., vol. 7(6):2297-2309 (2010).
Tsai, S. et al., "Reversal of autoimmunity by boosting memory-like autoregulatory T cells," Immunity, vol. 32(4):568-580 (2010).
Um, et al., "Enzyme-catalysed assembly of DNA hydrogel," Nat Mater., vol. 5(10):797-801 (2006).
Van Broekhoven, et al., "The novel chelator lipid 3(nitrilotriacetic acid)-ditetradecylamine (NTA3-DTDA) promotes stable binding of His-tagged proteins to liposomal membranes: potent anti-tumor responses induced by simultaneously targeting antigen, cytokine and costimulatory signals to T cells," Biochim Biophys Acta., vol. 1716(2):104-116 (2006).
van Ostaijen-ten Dam, et al., "Preparation of Cytokine-activated NK Cells for Use in Adoptive Cell Therapy in Cancer Patients: Protocol Optimization and Therapeutic Potential," J. Immunother. 39:90-100 (2016).
Vancha, A. et al., "Use of polyethyleneimine polymer in cell culture as attachment factor and lipofection enhancer," BMC Biotechnology, vol. 4 (23) (2004) (12 pages).
Vangala, et al., "Comparison of vesicle based antigen delivery systems for delivery of hepatitis B surface antigen," J Controlled Release, vol. 119(1):102-110 (2007).
Vasir, et al., "Biodegradable nanoparticles for cytosolic delivery of therapeutics," Adv Drug Deliv Rev, vol. 59(8):718-728 (2007) (20 pages).
Verma, et al., "Surface-structure-regulated cell-membrane penetration by monolayer-protected nanoparticles," Nat Mater., vol. 7(7):588-595 (2008) (15 pages).
Von Maltzahn, et al., "In vivo tumor cell targeting with click nanoparticles," Bioconjug Chem., vol. 19(8):1570-1578 (2008) (15 pages).
Vonarbourg, et al., "Parameters influencing the stealthiness of colloidal drug delivery systems," Biomaterials, vol. 27(24):4356-4373 (2006).
Vugmeyster, Yulia et al., "Pharmacokinetic, biodistribution, and biophysical profiles of TNF nanobodies conjugated to linear or branched poly(ethylene glycol)," Bioconjugate Chemistry, vol. 23(7):1452-1462 (2012).
Wakita, et al., "An indispensable role of type-1 IFNs for inducing CTL-mediated complete eradication of established tumor tissue by CpG-liposome co-encapsulated with model tumor antigen," Int Immunol., vol. 18(3):425-434 (2006).
Walter, R. et al., "Simultaneously targeting CD45 significantly increases cytotoxicity of the anti-CD33 immunoconjugate, gemtuzumab ozogamicin, against acute myeloid leukemia (AML) cells and improves survival of mice bearing human AML xenografts," Blood, vol. 111(9):4813-4816 (2008).
Wang, X. et al., "A transgene-encoded cell surface polypeptide for selection, in vivo tracking, and ablation of engineered cells," Blood, vol. 118(5):1255-1263 (2011).
Wei, et al., "The Sushi Domain of Soluble IL-15 Receptor a Is Essential for Binding IL-15 and Inhibiting Inflammatory and Allogenic Responses In Vitro and In Vivo," J. Immunol. 167:277-282 (2001).
Weinstein, J. et al., "Antibody-mediated targeting of liposomes, Binding to lymphocytes does not ensure incorporation of vesicle contents into the cells," Biochimica Biophys Acta., vol. 509(2):272-288 (1978).
Westwood, J.et al., "Three agonist antibodies in combination with high-dose IL-2 eradicate orthotopic kidney cancer in mice," Journal of Translational Medicine, vol. 8(42):1-8 (2010).
Westwood, J.et al., "Toll-Like Receptor Triggering and T-Cell Costimulation Induce Potent Antitumor Immunity in Mice," CCR, vol. 15(24):7624-7633 (2009).
Wilson-Welder, et al., "Vaccine adjuvants: current challenges and future approaches," J Pharm Sci., vol. 98(4):1278-1316 (2008).
Written Opinion of the International Search Authority in International Application No. PCT/US2017/037249 dated Sep. 19, 2017.
Written Opinion of the International Search Authority in International Application No. PCT/US2018/049596 dated Nov. 19, 2018.
Wu, et al., "Synthesis and Performance of Hot Melt Polyurethane Adhesive via Diels-Alder Reaction," Gaofenzi Cailiao Kexue Yu Gongcheng 31:1-5 (2015).
Xing, T. et al., "Disulfide Core Cross-Linked PEGylated Polypeptide Nanogel Prepared by a One-Step Ring Opening Copolymerization of N-Carboxyanhydrides fordrug delivery," Macromolecular Journals, vol. 11:962-969 (2011).
Xu, J. et al., "Rendering protein-based particles transiently insoluble for therapeutic applications," The Journal of the American Chemical Society, vol. 134 (21):8774-8777 (2012).
Yan, M. et al. "A novel intracellular protein delivery platform based on single-protein nanocapsules," Nat Nanotechnol., vol. 5(I):48-53 (2010).
Yee, et al., "Adoptive T cell therapy using antigen-specific $CD8_+$ T cell clones for the treatment of patients with metastatic melanoma: in vivo persistence, migration, and antitumor effect of transferred T cells," Proc Natl Acad Sci USA., vol. 99(25): 16168-16173 (2002).
Zahn, et al., "Isolierung und Synthese von Oligomeren aus Hexamethylen-di-isocyanat und Butandiol-(1.4)," Chem. Ber. 94:125-131 (1961).
Zahn, et al., "Lineare Oligomere aus Hexamethylendiisocyanat und Butandiol-(1,4)," Macromol. Chem. Phys. 44:290-311 (1961).
Zauner, et al., "In vitro uptake of polystyrene microspheres: effect of particle size, cell line and cell density," J Control Release, vol. 71(1):39-51 (2001).
Zhang, et al., "Folate-decorated poly(lactide-co-glycolide)-vitamin E TPGS nanoparticles for targeted drug delivery," Biomaterials, vol. 28(10):1889-1899 (2007).
Zhao, et al., "Directed cell migration via chemoattractants released from degradable microspheres," Biomaterials, vol. 26(24):5048-5063 (2005).
Zheng, et al., "In vivo targeting of adoptively transferred T-cells with antibody- and cytokineconjugated liposomes," J Control Release, vol. 172(2):426-435 (2013).
Zheng, "In vivo Arming of Adoptively Transferred T-cells with Drug-loaded Nanoparticles for Cancer Immunotherapy," BMES. Presentation MIT., 18 pages (2012).
Zhu, et al., "Stabilization of proteins encapsulated in injectable poly (lactide-co-glycolide)," Nat Biotechnol. vol. 18(1):52-57 (1999).
Sahaf, B. et al., "Lymphocyte surface thiol levels," Proc Natl Acad Sci USA., vol. 100(7):4001-4005 (2003).

THERAPEUTIC PROTEIN COMPOSITIONS AND METHODS OF MAKING AND USING THE SAME

CROSS REFERENCE TO RELATED APPLICATIONS

This application is a U.S. National Phase application under 35 U.S.C. 371 of International Application No. PCT/US2018/049596, filed Sep. 5, 2018, which claims priority to and the benefit of U.S. Provisional Application Nos. 62/554,058 filed Sep. 5, 2017 and 62/657,218 filed Apr. 13, 2018, the disclosures of each of which applications are hereby incorporated herein by reference in its entirety.

FIELD

The present disclosure generally relates to compositions and methods for preparation and delivery of protein therapeutics, and more particularly protein clusters or backpacks having a plurality of therapeutic protein monomers reversibly crossed-linked by biodegradable linkers.

BACKGROUND

Protein therapeutics, such as antibodies, cytokines, growth factors and vaccines, are important therapeutics for the treatment of a variety of diseases including, for example, cancer, diabetes and cardiovascular diseases. This class of protein therapeutics has been developed rapidly in the global pharmaceutical industry over the last few years. Protein therapeutics have the advantages of high specificity and potency relative to small molecule drugs. Nonetheless, the use of protein therapeutics is limited as a result of their intrinsic instability, immunogenicity and short half-life.

To address these limitations, there are generally two approaches: one is genetic fusion of the therapeutic protein, and the other is use of engineered carriers to deliver protein therapeutics. With engineered carriers, proteins are loaded by either encapsulation/adsorption or conjugation. Encapsulation or adsorption of proteins in/onto liposomes or nanoparticles is typically inefficient. Conjugation of proteins typically reduces their bioactivity. Therefore, both approaches are problematic.

Thus, a significant need exists for new compositions and methods that incorporate therapeutics into a delivery system with high efficiency.

SUMMARY

Disclosed herein are improved methods and compositions for protein therapeutics. More particularly, disclosed herein are protein clusters or backpacks having a plurality of therapeutic protein monomers reversibly crossed-linked by biodegradable linkers, and methods for preparing and using the same.

In one aspect, disclosed herein is a therapeutic composition comprising:
  a protein cluster comprising a plurality of therapeutic protein monomers reversibly crossed-linked to one another, wherein the protein cluster has a size between 30 nm and 1000 nm in diameter measured by dynamic light scattering;
  a plurality of biodegradable cross-linkers each having two, three or four functional groups capable of reacting with nucleophilic groups on the therapeutic protein monomers, thereby cross-linking the therapeutic protein monomers into the protein cluster, wherein the cross-linker degrades, after administration into a subject in need thereof, under physiological conditions so as to release the therapeutic protein monomers from the protein cluster;
  a pharmaceutically acceptable carrier or excipient; and
  optionally, a surface modification on the protein cluster, wherein preferably the surface modification is polycation.

In some embodiments, the cross-linker has the formula of A-B-C wherein B is optional, wherein A represents a structural template, B represents a polymer spacer, C represents a hydrolysable linkage and a functional group that can react with nucleophilic groups.

In some examples, A is selected from di-ols, tri-ols, tetra-ols, poly-ols, di-thiols, tri-thiols, tetra-thiols, poly-thiols, di-amines, tri-amines, tetra-amines, or poly-amines. In some embodiments, B can be selected from polyethylene glycol, saccharides, poly-ols, poly-ethers, poly-thioethers, poly-amines, poly-esters, alkanes, phenyls, or amino-acids. In some embodiments, C can have C has formula (Ia):

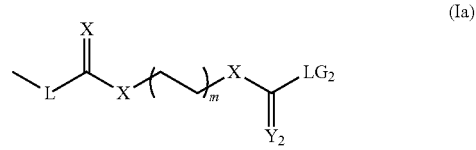

wherein:
  $LG_2$ is a leaving group selected from triflate, tosyl, Cl, N-hydroxysuccinimide and imidazolide;
  $Y_2$ is selected from O and S;
  X, at each occurrence, is independently selected from O, S, and N;
  L is optional and is a linker such

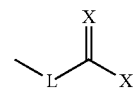

that is biodegradable; and
  m is an integer selected from 1-6, preferably 2.

In certain embodiments, the cross-linker has formula (I):

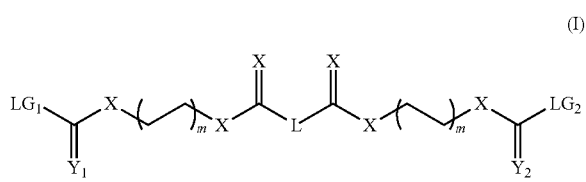

wherein:
  $LG_1$ and $LG_2$ are each a leaving group, independently selected from triflate, tosyl, Cl, N-hydroxysuccinimide and imidazolide;
  $Y_1$ and $Y_2$ are each independently selected from O and S;
  X, at each occurrence, is independently selected from O, S, and N;

L is a linker such that

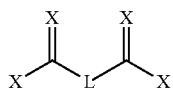

is biodegradable; and m, at each occurrence, is an integer selected from 1-6.

In some embodiments, the cross-linker of formula (I) is symmetrical.

In some embodiments, $LG_1$ and $LG_2$ are capable of reacting with a protein, a drug and/or a particle. In one example, $LG_1$ and $LG_2$ are both imidazolide. In another example, $LG_1$ and $LG_2$ are both N-hydroxysuccinimide.

In some embodiments,

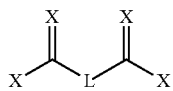

is hydrolysable.

In some embodiments, e.g., when one or more X is N, L is selected from:
(a) —$(CH_2)_n$— wherein n is an integer selected from 0-5;
(b)

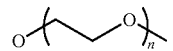

wherein n is an integer selected from 0-5; or
(c)

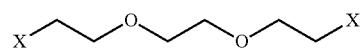

wherein X, at each occurrence, is independently selected from O, S, and N.

In some embodiments, m is 2.

In certain embodiments, the cross-linker has formula (II):

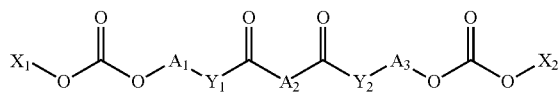

(II)

wherein:
$X_1$ and $X_2$ are each independently selected from triflate, tosyl, Cl, N-hydroxysuccinimide and imidazolide,
$A_1$ and $A_3$ are each independently —$(CR^1R^2)_n$—;
$A_2$ is —$(CR^1R^2)_m$—;
$Y_1$ and $Y_2$ are each independently selected from $NR^3$, O and S;
wherein $R^1$ and $R^2$ at each occurrence are independently selected from hydrogen, halogen, hydroxyl, $C_{1-12}$ alkyl, $C_{2-12}$ alkenyl, $C_{3-12}$ cycloalkyl, $C_{2-12}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl wherein $R^3$ is selected from hydrogen, $C_{1-12}$ alkyl, $C_{2-12}$ alkenyl, $C_{3-12}$ cycloalkyl, $C_{2-12}$ heterocyclyl; $C_{6-12}$ aryl optionally substituted with 1 or more halo, hydroxyl, $C_{1-6}$ alkyl and/or $C_{1-6}$ alkoxyl; and $C_{4-12}$ heteroaryl optionally substituted with 1 or more halo, hydroxyl, $C_{1-6}$ alkyl and/or $C_{1-6}$ alkoxyl;
n, at each occurrence, is an integer independently selected from 1-12; and
m is an integer selected from 0-12.

In some embodiments, the cross-linker of formula (II) is symmetrical. In some embodiments, $X_1$ and $X_2$ can each be a leaving group capable of reacting with a protein, a drug and/or a particle. In one example, $X_1$ and $X_2$ are both imidazolide. In another example, $X_1$ and $X_2$ are both N-hydroxysuccinimide. In some embodiments, $R^1$ and $R^2$ are both hydrogen. In one example, $A_1$ and $A_3$ are both —$(CH_2)_2$—. In one embodiment, $A_2$ is —$(CH_2)_2$—. In some embodiments, $Y_1$ and $Y_2$ are both 0.

In one embodiment, the cross-linker is:

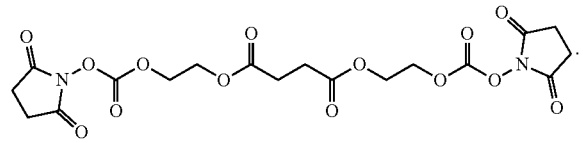 [SMILES: O=C(CCC(=O)OCCOC(=O)ON1C(=O)CCC1=O)OCCOC(=O)ON1C(=O)CCC1=O]

In some embodiments, in the cross-linker of formula (II), $A_2$ is a bond (e.g., when m is 0). In one embodiment, $Y_1$ and $Y_2$ are both NH.

The cross-linker, in some embodiments, is:

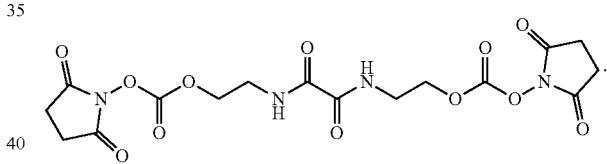

In some embodiments, the cross-linker can be used as a degradable or hydrolysable linker. In some embodiments, the degradable linker is a redox responsive linker. Methods of making and using various linkers (e.g., to make nanogels or backpacks) are disclosed in U.S. Publication No. 2017/0080104, U.S. Pat. No. 9,603,944, and U.S. Publication No. 2014/0081012, each of which is incorporated herein by reference in its entirety.

In some embodiments, the composition further comprises an agent that optimizes formation of the protein cluster. For example, the agent can increase yield of the protein cluster formation by reducing non-reacted proteins in comparison to a composition without the agent. In some embodiments, the agent increases yield of the protein cluster formation by reducing formation of clusters that are larger than 1000 nm in size compared to a composition without the agent.

In some embodiments, in the composition disclosed herein, the therapeutic protein monomers comprise one or more cytokine molecules and/or one or more costimulatory molecules, wherein:
(i) the one or more cytokine molecules are selected from IL15, IL2, IL7, IL10, IL12, IL18, IL21, IL-23, IL-4, IL1alpha, IL1beta, IL-5, IFNgamma, TNFa, IFNalpha, IFNbeta, GM-CSF, or GCSF; and (ii) the one or more costimulatory molecules are selected from CD137, OX40, CD28, GITR, VISTA, anti-CD40, or CD3.

Another aspect relates to a method for preparing any one of the composition disclosed herein, the method comprising reacting the plurality of therapeutic protein monomers with the plurality of cross-linkers to form the protein cluster. In some embodiments, the reacting step is performed at a temperature between about 5° C. and about 40° C. In some embodiments, the reacting step is performed for about 1 minute to about 8 hours. The method can further include providing the surface modification to the protein cluster and/or purifying the protein cluster.

Also provided herein is a method for preparing a cell therapy composition, comprising: providing any one of the composition disclosed herein; and incubating the protein cluster with a nucleated cell such as T and NK cells, preferably for about 30-60 minutes.

A further aspect relates to a cell therapy composition, comprising any one of the composition disclosed herein, associated with a nucleated cell such as T and NK cells.

Still a further aspect relates to a method of providing cell therapy, comprising administering the cell therapy composition disclosed herein into a subject in need thereof.

DETAILED DESCRIPTION

Figure 1A:
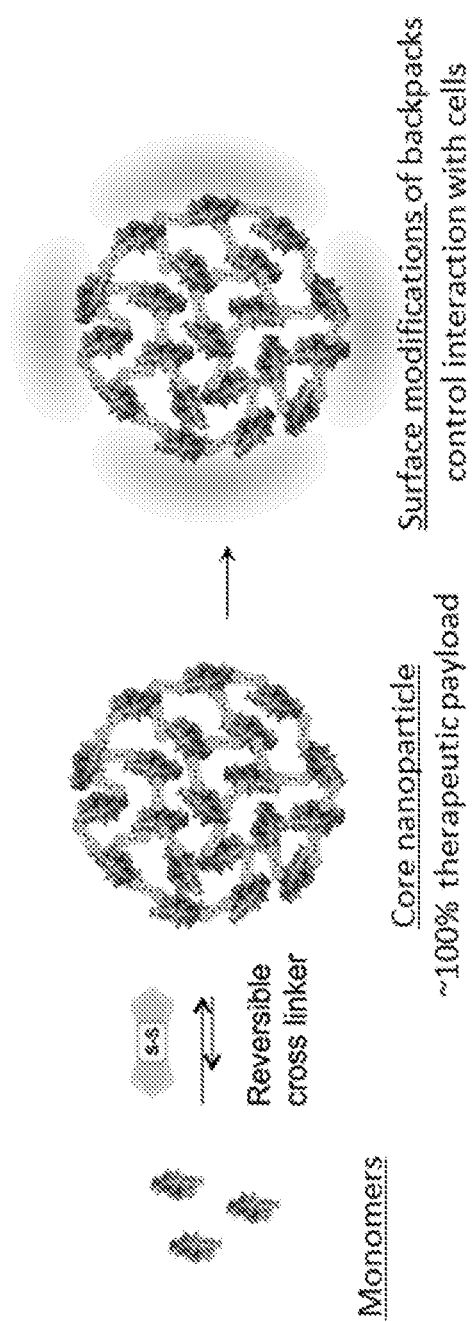
FIGS. 1A-1C illustrates exemplary backpacks and their making and using.

Cancer immunotherapy, including adoptive T cell therapy, is a promising strategy to treat cancer because it harnesses a subject's own immune system to attack cancer cells. Nonetheless, a major limitation of this approach is the rapid decline in viability and function of the transplanted T lymphocytes. In order to maintain high numbers of viable tumor-specific cytotoxic T lymphocytes in tumors, co-administration of immunostimulatory agents with transferred cells is necessary. When given systemically at high doses, these agents could enhance the in vivo viability of transferred (i.e., donor) cells, improve the therapeutic function of transferred cells, and thus lead to overall improved efficacy against cancer; however, high doses of such agents could also result in life-threatening side effects. For example, the use of interleukin-2 (IL-2) as an adjuvant greatly supports adoptive T cell therapy of melanoma, where IL-2 provides key adjuvant signals to transferred T cells but also elicits severe dose-limiting inflammatory toxicity and expands regulatory T cells (Tregs). One approach to focus adjuvant activity on the transferred cells is to genetically engineer the transferred cells to secrete their own supporting factors. The technical difficulty and challenges as well as the high cost for large-scale production of genetically engineered T lymphocytes have significantly limited the potential of this method in clinical applications, to date.

Disclosed herein, in some aspects, is a technology platform that permits simple, safe and efficient delivery of biologically-active agents, such as a drug, protein (e.g., adjuvants such as IL-2) or particle to cells through chemical conjugation of protein, drug, or particle-loaded, carrier-free linkers directly onto the plasma membrane of cells. In certain embodiments, such composition is referred to as "nanogel," "nanoparticle," or "backpack," which terms are used interchangeably herein. The composition can be loaded or backpacked onto cells, e.g., nucleated cells. The loading or backpacking process is also referred to as "priming." Backpacked or primed cells can have many therapeutic applications. For example, backpacked T cells can be used in T cell therapies including ACT (adoptive cell therapy). Other important immune cell types can also be backpacked, including for example, B cells, tumor infiltrating lymphocytes, NK cells, antigen-specific CD8+ T cells, T cells genetically engineered to express chimeric antigen receptors (CARs) or CAR-T cells, T cells genetically engineered to express T-cell receptors specific to an tumor antigen, tumor infiltrating lymphocytes (TILs), and/or antigen-trained T cells (e.g., T cells that have been "trained" by antigen presenting cells (APCs) displaying antigens of interest, e.g. tumor associated antigens (TAA)).

In addition to the foregoing, the present disclosure further contemplates other nanostructures that comprise other protein therapeutics for purposes other than adjuvant effect on adoptively-transferred cells. Those of skill in the art will readily recognize that the disclosure has broader applications, as provided herein.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values. The term "substantially" means more than 50%, preferably more than 80%, and most preferably more than 90% or 95%.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used herein, "a plurality of" means more than 1, e.g., 2, 3, 4, 5, 6, 7, 8, 9, 10, 11, 12, 13, 14, 15, 16, 17, 18, 19, 20, or more, e.g., 25, 30, 40, 50, 60, 70, 80, 90, 100, 200, 300, 400, 500, or more, or any integer therebetween.

The term "therapeutic," "therapeutic agent," "active," "active agent," "active pharmaceutical agent," "active drug" or "drug" as used herein means any active pharmaceutical ingredient ("API"), including its pharmaceutically acceptable salts (e.g. the hydrochloride salts, the hydrobromide salts, the hydroiodide salts, and the saccharinate salts), as well as in the anhydrous, hydrated, and solvated forms, in the form of prodrugs, and in the individually optically active enantiomers of the API as well as polymorphs of the API. Therapeutic agents include pharmaceutical, chemical or biological agents. Additionally, pharmaceutical, chemical or biological agents can include any agent that has a desired property or affect whether it is a therapeutic agent. For example, agents also include diagnostic agents, biocides and the like.

The terms "protein", "peptide" and "polypeptide" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures. It should be understood that the term "protein" includes fusion or chimeric proteins, as well as cytokines, antibodies and antigen-binding fragments thereof.

"Antibody" or "antibody molecule" as used herein refers to a protein, e.g., an immunoglobulin chain or fragment thereof, comprising at least one immunoglobulin variable domain sequence. An antibody molecule encompasses antibodies (e.g., full-length antibodies) and antibody fragments. In an embodiment, an antibody molecule comprises an antigen binding or functional fragment of a full length antibody, or a full length immunoglobulin chain. For example, a full-length antibody is an immunoglobulin (Ig) molecule (e.g., IgG) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')$_2$, F(ab)$_2$, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')$_2$ fragments, and single chain variable fragments (scFvs). The terms "Fab" and "Fab fragment" are used interchangeably and refer to a region that includes one constant and one variable domain from each heavy and light chain of the antibody, i.e., $V_L$, $C_L$, $V_H$, and $C_H$1.

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Antigen" (Ag) as used herein refers to a macromolecule, including all proteins or peptides. In some embodiments, an antigen is a molecule that can provoke an immune response, e.g., involving activation of certain immune cells and/or antibody generation. Antigens are not only involved in antibody generation. T cell receptors also recognized antigens (albeit antigens whose peptides or peptide fragments are complexed with an MHC molecule). Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site" or "antigen-binding fragment" or "antigen-binding portion" (used interchangeably herein) of an antibody molecule refers to the part of an antibody molecule, e.g., an immunoglobulin (Ig) molecule such as IgG, that participates in antigen binding. In some embodiments, the antigen-binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions" (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4. Variable light chain (VL) CDRs are generally defined to include residues at positions 27-32 (CDR1), 50-56 (CDR2), and 91-97 (CDR3). Variable heavy chain (VH) CDRs are generally defined to include residues at positions 27-33 (CDR1), 52-56 (CDR2), and 95-102 (CDR3). One of ordinary skill in the art would understand that the loops can be of different length across antibodies and the numbering systems such as the Kabat or Chotia control so that the frameworks have consistent numbering across antibodies.

In some embodiments, the antigen-binding fragment of an antibody (e.g., when included as part of a fusion molecule) can lack or be free of a full Fc domain. In certain embodiments, an antibody-binding fragment does not include a full IgG or a full Fc but may include one or more constant regions (or fragments thereof) from the light and/or heavy chains. In some embodiments, the antigen-binding fragment can be completely free of any Fc domain. In some embodiments, the antigen-binding fragment can be substantially free of a full Fc domain. In some embodiments, the antigen-binding fragment can include a portion of a full Fc domain (e.g., CH2 or CH3 domain or a portion thereof). In some embodiments, the antigen-binding fragment can include a full Fc domain. In some embodiments, the Fc domain is an IgG domain, e.g., an IgG1, IgG2, IgG3, or IgG4 Fc domain. In some embodiments, the Fc domain comprises a CH2 domain and a CH3 domain.

As used herein, a "cytokine" or "cytokine molecule" refers to full length, a fragment or a variant of a naturally-occurring, wild type cytokine (including fragments and functional variants thereof having at least 10% of the activity of the naturally-occurring cytokine molecule). In embodiments, the cytokine molecule has at least 30, 50, or 80% of the activity, e.g., the immunomodulatory activity, of the naturally-occurring molecule. In embodiments, the cytokine molecule further comprises a receptor domain, e.g., a cytokine receptor domain, optionally, coupled to an immunoglobulin Fc region. In other embodiments, the cytokine molecule is coupled to an immunoglobulin Fc region. In other embodiments, the cytokine molecule is coupled to an antibody molecule (e.g., an immunoglobulin Fab or scFv fragment, a Fab fragment, a FAB$_2$ fragment, or an affibody fragment or derivative, e.g., a sdAb (nanobody) fragment, a heavy chain antibody fragment, single-domain antibody, a bi-specific or multispecific antibody), or non-antibody scaffolds and antibody mimetics (e.g., lipocalins (e.g., anticalins), affibodies, fibronectin (e.g., monobodies or Adnectins), knottins, ankyrin repeats (e.g., DARPins), and A domains (e.g., avimers)).

As used herein, "administering" and similar terms mean delivering the composition to an individual being treated. Preferably, the compositions of the present disclosure are administered by, e.g., parenteral, including subcutaneous, intramuscular, or preferably intravenous routes.

As used herein, the terms "cancer" and "cancerous" refer to or describe the physiological condition in mammals that is typically characterized by unregulated cell growth. Examples of cancer include, but are not limited to, melanoma, carcinoma, lymphoma, blastoma, sarcoma, and leukemia or lymphoid malignancies. More particular examples of cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Nucleated cells" are cells which contain nucleus. In some embodiments, the nucleated cells can be immune cells.

As used herein, an "immune cell" refers to any of various cells that function in the immune system, e.g., to protect against agents of infection and foreign matter. In embodiments, this term includes leukocytes, e.g., neutrophils, eosinophils, basophils, lymphocytes, and monocytes. The term "immune cell" includes immune effector cells described herein. "Immune cell" also refers to modified versions of cells involved in an immune response, e.g. modified NK cells, including NK cell line NK-92 (ATCC cat. No. CRL-2407), haNK (an NK-92 variant that expresses the high-affinity Fc receptor FcγRIIIa (158V)) and taNK (targeted NK-92 cells transfected with a gene that expresses a CAR for a given tumor antigen), e.g., as described in Klingemann et al. supra.

"Immune effector cell," as that term is used herein, refers to a cell that is involved in an immune response, e.g., in the promotion of an immune effector response. Examples of immune effector cells include, but are not limited to, T cells, e.g., CD4+T cells, CD8+ T cells, alpha T cells, beta T cells, gamma T cells, and delta T cells; B cells; natural killer (NK) cells; natural killer T (NKT) cells; dendritic cells; and mast cells. In some embodiments, the immune cell is an immune cell (e.g., T cell or NK cell) that comprises, e.g., expresses, a Chimeric Antigen Receptor (CAR), e.g., a CAR that binds to a cancer antigen. In other embodiments, the immune cell expresses an exogenous high affinity Fc receptor. In some embodiments, the immune cell comprises, e.g., expresses, an engineered T-cell receptor. In some embodiments, the immune cell is a tumor infiltrating lymphocyte. In some embodiments the immune cells comprise a population of immune cells and comprise T cells that have been enriched for specificity for a tumor-associated antigen (TAA), e.g. enriched by sorting for T cells with specificity towards MHCs displaying a TAA of interest, e.g. MART-1. In some embodiments immune cells comprise a population of immune cells and comprise T cells that have been "trained" to possess specificity against a TAA by an antigen presenting cell (APC), e.g. a dendritic cell, displaying TAA peptides of interest. In some embodiments, the T cells are trained against a TAA chosen from one or more of MART-1, MAGE-A4, NY-ESO-1, SSX2, Survivin, or others. In some embodiments the immune cells comprise a population of T cells that have been "trained" to possess specificity against a multiple TAAs by an APC, e.g. a dendritic cell, displaying multiple TAA peptides of interest. In some embodiments, the immune cell is a cytotoxic T cell (e.g., a CD8+ T cell). In some embodiments, the immune cell is a helper T cell, e.g., a CD4+ T cell.

"Cytotoxic T lymphocytes" (CTLs) as used herein refer to T cells that have the ability to kill a target cell. CTL activation can occur when two steps occur: 1) an interaction between an antigen-bound MHC molecule on the target cell and a T cell receptor on the CTL is made; and 2) a costimulatory signal is made by engagement of costimulatory molecules on the T cell and the target cell. CTLs then recognize specific antigens on target cells and induce the destruction of these target cells, e.g., by cell lysis. In some embodiments, the CTL expresses a CAR. In some embodiments, the CTL expresses an engineered T-cell receptor.

As used herein, an "effective amount" means the amount of bioactive agent or diagnostic agent that is sufficient to provide the desired local or systemic effect at a reasonable risk/benefit ratio as would attend any medical treatment or diagnostic test. This will vary depending on the patient, the disease, the treatment being effected, and the nature of the agent.

As used herein, "pharmaceutically acceptable" shall refer to that which is useful in preparing a pharmaceutical composition that is generally safe, non-toxic, and neither biologically nor otherwise undesirable and includes that which is acceptable for veterinary use as well as human pharmaceutical use. Examples of "pharmaceutically acceptable liquid carriers" include water and organic solvents. Preferred pharmaceutically acceptable aqueous liquids include PBS, saline, and dextrose solutions etc.

The term "treatment" or "treating" means administration of a drug for purposes including: (i) preventing the disease or condition, that is, causing the clinical symptoms of the disease or condition not to develop; (ii) inhibiting the disease or condition, that is, arresting the development of clinical symptoms; and/or (iii) relieving the disease or condition, that is, causing the regression of clinical symptoms.

The following definitions for certain chemical groups are used, unless otherwise described. Specific and general values listed below for radicals, substituents, and ranges, are for illustration only; they do not exclude other defined values or other values within defined ranges for the radicals and substituents. Unless otherwise indicated, alkyl, alkoxy, alkenyl, and the like denote both straight and branched groups.

The term "alkyl" refers to a saturated hydrocarbon chain that may be a straight chain or branched chain, containing the indicated number of carbon atoms. For example, $C_{1-6}$ alkyl indicates that the group may have 1 to 6 (inclusive) carbon atoms in it. Any atom can be optionally substituted, e.g., by one or more substituents. Examples of alkyl groups include without limitation methyl, ethyl, n-propyl, isopropyl, and tert-butyl.

As referred to herein, the term "alkoxy" refers to a group of formula —O(alkyl). Alkoxy can be, for example, methoxy (—OCH$_3$), ethoxy, propoxy, isopropoxy, butoxy, iso-butoxy, sec-butoxy, pentoxy, 2-pentoxy, 3-pentoxy, or hexyloxy. As used herein, the term "hydroxyl," employed alone or in combination with other terms, refers to a group of formula —OH.

The term "alkenyl." refers to a straight or branched hydrocarbon chain containing the indicated number of carbon atoms and having one or more carbon-carbon double bonds. Any atom can be optionally substituted., e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from O, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein 1-2 of the ring atoms is independently selected from N, NH, N($C_1$-$C_6$ alkyl), NC(O)($C_1$-$C_6$ alkyl), O, and S; and wherein said heterocyclic ring is optionally substituted with 1-3 independently selected $R^{a}$" would include (but not be limited to) tetrahydrofuryl, tetrahydropyranyl, piperidyl (piperidino), piperazinyl, morpholinyl (morpholino), pyrrolinyl, and pyrrolidinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "aryl" refers to an aromatic monocyclic, bicyclic (2 fused rings), or tricyclic (3 fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polcyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents. Examples of heteroaryl groups include, but are not limited to, 2H-pyrrolyl, 3H-indolyl, acridinyl, benzo[b]thienyl, benzothiazolyl, P-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, phenanthridinyl, phenanthrolinyl, phenarsazinyl, phenazinyl, phenothiazinyl, phenoxathiinyl, phenoxazinyl, phthalazinyl, pteridinyl, purinyl, pyrallyl, pyrazinyl, pyrazolyl, pyridazinyl, pyridyl, pyrimidinyl, pyrrolyl, quinazolnyl, quinolyl, quinoxalinyl, thiadiazolyl, thianthrenyl, thiazolyl, thienyl, triazolyl, and xanthenyl.

The term "substituent" refers to a group "substituted" on, e.g., an alkyl, haloalkyl, cycloalkyl, heterocyclyl, heterocycloalkenyl, cycloalkenyl aryl, or heteroaryl group at any atom of that group. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. As used herein, the term "substituted" means that a hydrogen atom is removed and replaced by a substituent. It is understood that substitution at a given atom is limited by valency.

Various aspects of the disclosure are described in further detail below. Additional definitions are set out throughout the specification.

Linkers

In some embodiments, at least one drug, protein, polymer and/or particle (collectively, "agents") of the present disclosure are reversibly linked to one another through a degradable linker such that under physiological conditions, the linker degrades and releases the intact, biologically-active agent. In an embodiment, protein monomers can be cross-linked together to form a cluster that contains a plurality of the protein monomers. In other embodiments, various agents are linked to functional groups through a degradable linker. In various embodiments, the agents are reversibly modified or linked, as described below.

An agent that is "reversibly linked to another" agent, as used herein, refers to a drug, protein, polymer or particle that is attached (e.g., covalently attached) to another drug, protein, polymer or particle through a degradable linker.

An agent that is "reversibly linked to a functional group," or an agent that is "reversibly modified," herein refers to an agent that is attached (e.g., covalently attached) to a functional group through a degradable linker. Such an agent may be referred to herein as an "agent conjugate" or a "reversibly modified agent conjugate"—the terms may be used interchangeably herein. It should be understood that proteins and polymers (e.g., polyethylene glycol) each contain functional groups to which an agent can be linked via a reversible linker, such as amine, silane, hydroxyl, poly(ethylene oxide), polylactic acid, poly(lactic-co-glycolic acid), etc. Examples of agent conjugates and reversibly modified proteins, as provided herein, include without limitation, an agent reversibly linked (e.g., via a degradable linker) to another agent, an agent reversibly linked to a polymer, and a protein reversibly linked to another functional group. It should be understood that the term "protein" includes fusion proteins.

In some embodiments, the cross-linker has the formula of A-B-C wherein B is optional, wherein A represents a structural template, B represents a polymer spacer, C represents a hydrolysable linkage and a functional group that can react with nucleophilic groups.

In some examples, A is selected from di-ols, tri-ols, tetra-ols, poly-ols, di-thiols, tri-thiols, tetra-thiols, poly-thiols, di-amines, tri-amines, tetra-amines, or poly-amines. In some embodiments, B can be selected from polyethylene glycol, saccharides, poly-ols, poly-ethers, poly-thioethers, poly-amines, poly-esters, alkanes, phenyls, or amino-acids. In some embodiments, C can have C has formula (Ia):

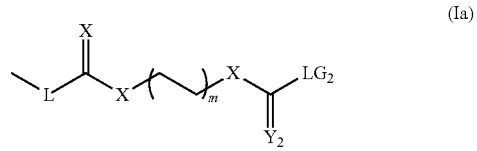

(Ia)

wherein:
LG$_2$ is a leaving group selected from triflate, tosyl, Cl, N-hydroxy succinimide and imidazolide;
Y$_2$ is selected from O and S;
X, at each occurrence, is independently selected from O, S, and N;
L is optional and is a linker such that

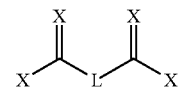

is biodegradable; and
m is an integer selected from 1-6, preferably 2.

An example of a degradable linker for use in accordance with the present disclosure is represented by formula (I):

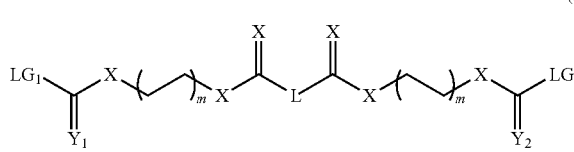
(I)

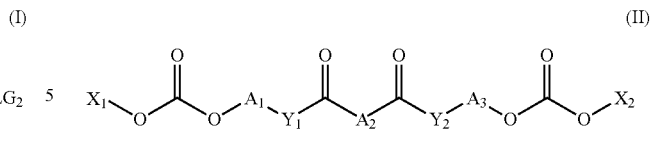
(II)

wherein:

LG$_1$ and LG$_2$ are each a leaving group, preferably independently selected from triflate, tosyl, Cl, N-hydroxysuccinimide and imidazolide;

Y$_1$ and Y$_2$ are each independently selected from O and S;

X, at each occurrence, is independently selected from O, S, and N;

L is a linkage such that

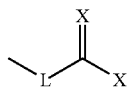

is biodegradable; and m, at each occurrence, is an integer selected from 1-6.

In some embodiments, the cross-linker represented by formula (I) is symmetrical at L. For example, LG$_1$ and LG$_2$ can be the same. Y$_1$ and Y$_2$ can be the same.

In various embodiments, LG$_1$ and LG$_2$ may be capable of reacting with a protein, a drug and/or a particle. LG$_1$ and LG$_2$ can both be imidazolide. In another example, LG$_1$ and LG$_2$ are both N-hydroxysuccinimide.

In certain embodiments,

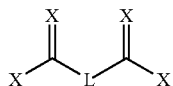

is hydrolysable. L can be selected from:

(a) —(CH$_2$)$_n$— wherein n is an integer selected from 0-5;

(b)

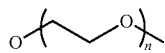

wherein n is an integer selected from 0-5; or (c)

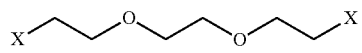

wherein X, at each occurrence, is independently selected from O, S, and N.

Another example of a degradable linker for use in accordance with the present disclosure is represented by formula (II):

wherein:

X$_1$ and X$_2$ are each independently selected from triflate, tosyl, Cl, N-hydroxysuccinimide and imidazolide;

A$_1$ and A$_3$ are each independently —(CR$^1$R$^2$)$_n$—;

A$_2$ is —(CR$^1$R$^2$)$_m$—;

Y$_1$ and Y$_2$ are each independently selected from NR$^3$, O and S;

wherein R$^1$ and R$^2$ at each occurrence are independently selected from hydrogen, halogen, hydroxyl, C$_{1-12}$ alkyl, C$_{2-12}$ alkenyl, C$_{3-12}$ cycloalkyl, C$_{2-12}$ heterocyclyl; C$_{6-12}$ aryl optionally substituted with 1 or more halo, hydroxyl, C$_{1-6}$ alkyl and/or C$_{1-6}$ alkoxyl; and C$_{4-12}$ heteroaryl optionally substituted with 1 or more halo, hydroxyl, C$_{1-6}$ alkyl and/or C$_{1-6}$ alkoxyl wherein R$^3$ is selected from hydrogen, C$_{1-12}$ alkyl, C$_{2-12}$ alkenyl, C$_{3-12}$ cycloalkyl, C$_{2-12}$ heterocyclyl; C$_{6-12}$ aryl optionally substituted with 1 or more halo, hydroxyl, C$_{1-6}$ alkyl and/or C$_{1-6}$ alkoxyl; and C$_{4-12}$ heteroaryl optionally substituted with 1 or more halo, hydroxyl, C$_{1-6}$ alkyl and/or C$_{1-6}$ alkoxyl;

n, at each occurrence, is an integer independently selected from 1-12; and m is an integer selected from 0-12.

In some embodiments, the cross-linker represented by formula (II) is symmetrical.

In some embodiments, X$_1$ and X$_2$ are each a leaving group capable of reacting with a protein, a drug and/or a particle. In certain embodiments, X$_1$ and X$_2$ are both imidazolide or N-hydroxysuccinimide.

In some embodiments, R$^1$ and R$^2$ are both hydrogen.

In some embodiments, A$_1$ and A$_3$ are both —(CH$_2$)$_2$—.

In certain embodiments, A$_2$ is —(CH$_2$)$_2$—.

In some embodiments, Y$_1$ and Y$_2$ are both O.

In some embodiments, the cross-linker is:

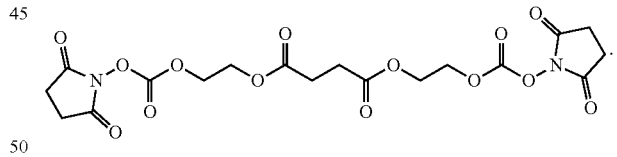

In some embodiments, A$_2$ is a bond. In certain embodiments, Y$_1$ and Y$_2$ are both NH.

In some embodiments, the cross-linker is:

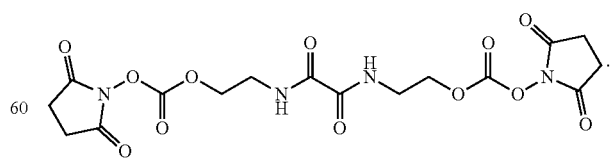

Monomers

Examples of protein monomers for use in accordance with the present disclosure include, without limitation, antibodies (e.g., IgG, Fab, mixed Fc and Fab), single chain antibodies, antibody fragments, engineered proteins such as Fc fusions, enzymes, co-factors, receptors, ligands, transcription factors and other regulatory factors, cytokines, chemokines, human serum albumin, and the like. These proteins may or may not be naturally occurring. Other proteins are contemplated and may be used in accordance with the disclosure. Any of the proteins can be reversibly modified through cross-linking to form a cluster or nanogel structure as disclosed in, e.g., U.S. Publication No. 2017/0080104, U.S. Pat. No. 9,603,944, U.S Publication No. 2014/0081012, and PCT Application No. PCT/US17/37249 filed Jun. 13, 2017, all incorporated herein by reference.

In various embodiments, therapeutic protein monomers can be cross-linked using one or more cross-linkers disclosed herein. The therapeutic protein monomers can comprise one or more cytokine molecules and/or one or more costimulatory molecules. Cytokine molecules can be selected from IL-15, IL-2, IL-7, IL-10, IL-12, IL-18, IL-21, IL-23, IL-4, IL1alpha, IL1beta, IL-5, IFNgamma, TNFa, IFNalpha, IFNbeta, GM-CSF, or GCSF. Costimulatory molecules are selected from CD137, OX40, CD28, GITR, VISTA, anti-CD40, or CD3.

In some embodiments, protein monomers of the disclosure are immunostimulatory proteins. As used herein, an immunostimulatory protein is a protein that stimulates an immune response (including enhancing a pre-existing immune response) in a subject to whom it is administered, whether alone or in combination with another protein or agent. Examples of immunostimulatory proteins that may be used in accordance with the disclosure include, without limitation, antigens, adjuvants (e.g., flagellin, muramyl dipeptide), cytokines including interleukins (e.g., IL-2, IL-7, IL-15 , IL-10, IL-18, IL-21, IL-23 (or superagonist/mutant forms of these cytokines, such as, IL-15SA), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunostimulatory proteins are contemplated and may be used in accordance with the disclosure. In some embodiments, the immunostimulatory proteins can be an antibody or antigen-binding fragment thereof that binds an inhibitor of an immunosuppressor, e.g., an inhibitor of a checkpoint inhibitor, such as PD-1, PD-L1, LAG-3, TIM-3, CTLA-4, inhibitory KIR, CD276, VTCN1, BTLA/HVEM, HAVCR2 and ADORA2A, e.g., as described in US 2016/0184399 incorporated herein by reference.

In some embodiments, protein monomers of the disclosure are antigens. Examples of antigens that may be used in accordance with the disclosure include, without limitation, cancer antigens, self-antigens, microbial antigens, allergens and environmental antigens. Other protein antigens are contemplated and may be used in accordance with the disclosure.

In some embodiments, proteins of the disclosure are cancer antigens. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-0017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-05. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, Imp-1, PIA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20 and c-erbB-2. Other cancer antigens are contemplated and may be used in accordance with the disclosure.

In some embodiments, proteins of the disclosure are antibodies or antibody fragments including, without limitation, bevacizumab (AVASTIN®), trastuzumab (HERCEPTIN®), alemtuzumab (CAMPATH®, indicated for B cell chronic lymphocytic leukemia,), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-05, IOR-T6 (anti-CD1), IOR EGF/R3, celogovab (ONCOSCINT® OV103), epratuzumab (LYMPHOCIDE®), pemtumomab (THERAGYN®) and Gliomab-H (indicated for brain cancer, melanoma). Other antibodies and antibody fragments are contemplated and may be used in accordance with the disclosure.

Proteins may be linked (e.g., covalently linked) to a degradable linker through any terminal or internal nucleophilic groups such as a —NH$_2$ functional group (e.g., side chain of a lysine). For example, proteins can be contacted with a degradable linker under conditions that permit reversible covalent crosslinking of proteins to each other through the degradable linker. In some embodiments, the proteins can be cross-linked to form a plurality of protein nanogels. In some embodiments, the conditions include contacting the protein with the degradable linker in an aqueous buffer at a temperature of 4° C. to 25° C. in some embodiments, the contacting step can be performed in an aqueous buffer for 3(minutes to one hour. In some embodiments, the aqueous buffer comprises phosphate buffered saline (PBS). In some embodiments, the concentration of the protein in the aqueous buffer is 10 mg/mL to 50 mg/mL (e.g., 10, 15, 20, 25, 30, 35, 40, 45 or 50 mg/mL).

Cytokines

The methods and compositions, e.g., linker compounds, described herein can be used to cross-link one or more cytokine molecules. In embodiments, the cytokine molecule is full length, a fragment or a variant of a cytokine, e.g., a cytokine comprising one or more mutations. In some embodiments the cytokine molecule comprises a cytokine chosen from interleukin-1 alpha (IL-1 alpha), interleukin-1 beta (IL-1 beta), interleukin-2 (IL-2), interleukin-4 (IL-4), interleukin-5 (IL-5), interleukin-6 (IL-6), interleukin-7 (IL-7), interleukin-10 (IL-10), interleukin-12 (IL-12), interleukin-15 (IL-15), interleukin-17 (IL-17), interleukin-18 (IL-18), interleukin-21 (IL-21), interleukin-23 (IL-23), interferon (IFN) alpha, IFN beta, IFN gamma, tumor necrosis alpha, GM-CSF, GCSF, or a fragment or variant thereof, or a combination of any of the aforesaid cytokines. In other embodiments, the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), interleukin-23 (IL-23) or interferon gamma, or a fragment or variant thereof, or a combination of any of the aforesaid cytokines. The cytokine molecule can be a monomer or a dimer.

In embodiments, the cytokine molecule further comprises a receptor domain, e.g., a cytokine receptor domain. In one embodiment, the cytokine molecule comprises an IL-15 receptor, or a fragment thereof (e.g., an extracellular IL-15 binding domain of an IL-15 receptor alpha) as described herein. In some embodiments, the cytokine molecule is an IL-15 molecule, e.g., IL-15 or an IL-15 superagonist as described herein. As used herein, a "superagonist" form of a cytokine molecule shows increased activity, e.g., by at least 10%, 20%, 30%, compared to the naturally-occurring cytokine. An exemplary superagonist is an IL-15 SA. In some embodiments, the IL-15 SA comprises a complex of IL-15 and an IL-15 binding fragment of an IL-15 receptor, e.g., IL-15 receptor alpha or an IL-15 binding fragment thereof, e.g., as described herein.

In other embodiments, the cytokine molecule further comprises an antibody molecule, e.g., an immunoglobulin Fab or scFv fragment, a Fab fragment, a FAB2 fragment, or an affibody fragment or derivative, e.g. a sdAb (nanobody) fragment, a heavy chain antibody fragment, e.g., an Fc region, single-domain antibody, a bi-specific or multispecific antibody). In one embodiment, the cytokine molecule further comprises an immunoglobulin Fc or a Fab.

In some embodiments, the cytokine molecule is an IL-2 molecule, e.g., IL-2 or IL-2-Fc. In other embodiments, a cytokine agonist can be used in the methods and compositions disclosed herein. In embodiments, the cytokine agonist is an agonist of a cytokine receptor, e.g., an antibody molecule (e.g., an agonistic antibody) to a cytokine receptor, that elicits at least one activity of a naturally-occurring cytokine. In embodiments, the cytokine agonist is an agonist of a cytokine receptor, e.g., an antibody molecule (e.g., an agonistic antibody) to a cytokine receptor chosen from an IL-15Ra or IL-21R.

In some embodiments, the cytokine molecule is an IL-15 molecule, e.g., a full length, a fragment or a variant of IL-15, e.g., human IL-15. In embodiments, the IL-15 molecule is a wild-type, human IL-15. In other embodiments, the IL-15 molecule is a variant of human IL-5, e.g., having one or more amino acid modifications. In some embodiments, the IL-15 molecule comprises a mutation, e.g., an N72D point mutation.

In other embodiments, the cytokine molecule further comprises a receptor domain, e.g., an extracellular domain of an IL-15R alpha, optionally, coupled to an immunoglobulin Fc or an antibody molecule. In embodiments, the cytokine molecule is an IL-15 superagonist (IL-15SA) as described in WO 2010/059253. In some embodiments, the cytokine molecule comprises IL-15 and a soluble IL-15 receptor alpha domain fused to an Fc (e.g., a sIL-15Ra-Fc fusion protein), e.g., as described in Rubinstein et al PNAS 103:24 p. 9166-9171 (2006).

The IL-15 molecule can further comprise a polypeptide, e.g., a cytokine receptor, e.g., a cytokine receptor domain, and a second, heterologous domain. In one embodiment, the heterologous domain is an immunoglobulin Fc region. In other embodiments, the heterologous domain is an antibody molecule, e.g., a Fab fragment, a Fab2 fragment, a scFv fragment, or an affibody fragment or derivative, e.g. a sdAb (nanobody) fragment, a heavy chain antibody fragment. In some embodiments, the polypeptide also comprises a third heterologous domain. In some embodiments, the cytokine receptor domain is N-terminal of the second domain, and in other embodiments, the cytokine receptor domain is C-terminal of the second domain.

Certain cytokines and antibodies are disclosed in e.g., U.S. Publication No. 2017/0080104, U.S. Pat. No. 9,603,944, U.S. Publication No. 2014/0081012, and PCT Application No. PCT/US2017/037249 (each incorporated herein by reference in its entirety).

In some embodiments, the cytokines or other immunemodulators can target receptors (e.g., on an immune cell) by way of a fusion protein, such as those disclosed in PCT Application Nos. PCT/US2018/040777, PCT/US18/40783 and PCT/US18/40786 (each incorporated herein by reference in its entirety).

Backpacks and Cell Therapy

Backpacks or nanoparticles can be prepared by crosslinking various therapeutic protein monomers using one or more cross-linkers disclosed herein, as shown in FIG. 1A. While the figure shows disulfide-containing linker, other biodegradable linkers disclosed herein can also be used.

In certain embodiments, the backpacks can be prepared by reacting the plurality of therapeutic protein monomers with the plurality of cross-linkers to form protein clusters having a size of, e.g., about 30 nm to 1000 nm in diameter. In some embodiments, the reaction can be performed at a temperature between about 5° C. and about 40° C. The reaction can be performed for about 1 minute to about 8 hours.

The protein clusters can be provided with a surface modification such as polycation. Certain surface modification is disclosed in U.S. Publication No. 2017/0080104 and U.S. Pat. No. 9,603,944, both incorporated herein by reference in their entirety. Examples include poly-Lysine (polyK), PEG-polyK, and poly-Arginine.

In some embodiments, the cross-linking reaction can proceed in the presence of one or more crowding agents such as polyethylene glycol (PEGs) and triglycerides. Exemplary PEGs include PEG400, PEG1000, PEG1500, PEG2000, PEG3000 and PEG4000.

Certain protein solubility aids such as glycerol, ethylene glycol and propylene glycol, Sorbitol and Mannitol can also improve the yield of backpack formation.

In certain embodiments, certain crosslinkers of the invention, due to the reaction of cationic lysine residues in the backpack, will result in a backpack having a net negative charge which will inhibit cell attachment. As such, it may be useful to first complex backpacks with a polycation via electrostatic interactions to drive cell attachment. For example, the backpacks can be coated or surface modified with a polycation such as polylysine (poly-L-lysine), polyethyleneimine, polyarginine, polyhistidine, polybrene and/or DEAE-dextran. Polycation can help the backpacks nonspecifically bind or adsorb on cell membranes which are negatively charged. In some embodiments, polycation to be contained in a mixed solution may be a polymeric compound having a cationic group or a group that may become a cationic group, and an aqueous solution of a free polycation shows basic. Examples of the group that may become a cationic group include an amino group, an imino group, and the like. Examples of polycation include: polyamino acid such as polylysine, polyornithine, polyhistidine, polyarginine, polytryptophan, poly-2,4-diaminobutyric acid, poly-2,3-diaminopropionic acid, protamine, and polypeptide having at least one or more kinds of amino acid residues in a polypeptide chain selected from the group consisting of lysine, histidine, arginine, tryptophan, ornithine, 2,4-diaminobutyric acid and 2,3-diaminopropionic acid; polyamine such as polyallylamine, polyvinylamine, a copolymer of allylamine and diallylamine, and polydiallylamine; and polyimine such as polyethyleneimine.

In some embodiments, the polycation coating or surface modifying agent used to promote backpack adhesion to the cell is a cationic block copolymer of PEG-polylysine such as [methoxy-poly(ethylene glycol)n-block-poly(L-lysine hydrochloride), PEG-polylysine] (PK30). This block copolymer may contain approximately 114 PEG units (MW approximately 5000 Da) and 30 lysine units (MW approximately 4900 Da). The linear PEG polymer has a methoxy end group, the poly-lysines are in the hydrochloride salt form. PK30 is a linear amphiphilic block copolymer which has a poly(L-lysine hydrochloride) block and a non-reactive PEG block. The poly-L-lysine block provides a net cationic charge at physiological pH and renders the backpack with a net positive charge after association. PK30 Structure [Methoxy-poly(ethylene glycol)n-block-poly(L-lysine hydrochloride)] is as follows.

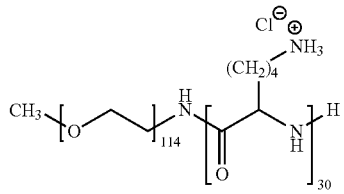

In some embodiments, the backpacks can be coated with an antibody or antigen-binding fragment thereof that bind to a receptor on the surface of an immune cell, so as to specifically target the backpacks to the immune cell. Exemplary antibodies include those disclosed herein, or fusion proteins containing the same.

Figure 1B:
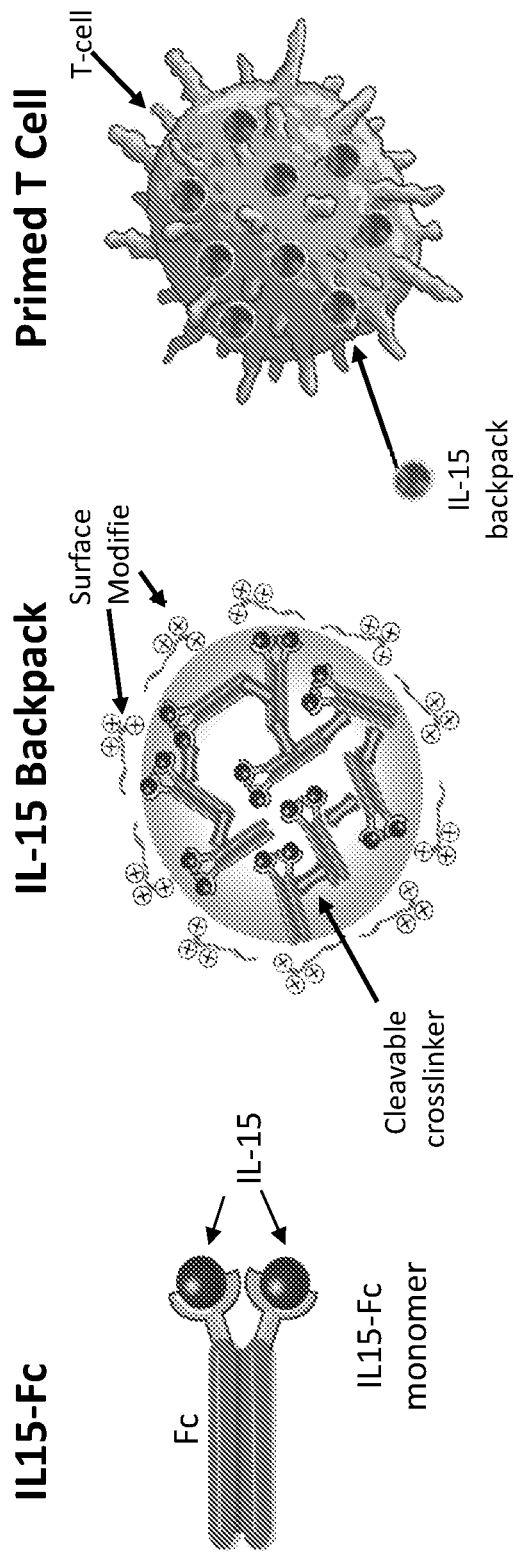

In one example, as illustrated in FIG. 1B, "IL15-Fc" (IL15Ra-sushi-domain-Fc fusion homodimer protein with two associated IL-15 Proteins) monomers can be crossed linked and surface modified with polycation, to form IL-15 backpacks. The IL-15 backpacks can then be loaded onto immune cells such as T cells to form primed T cells.

Figure 1C:
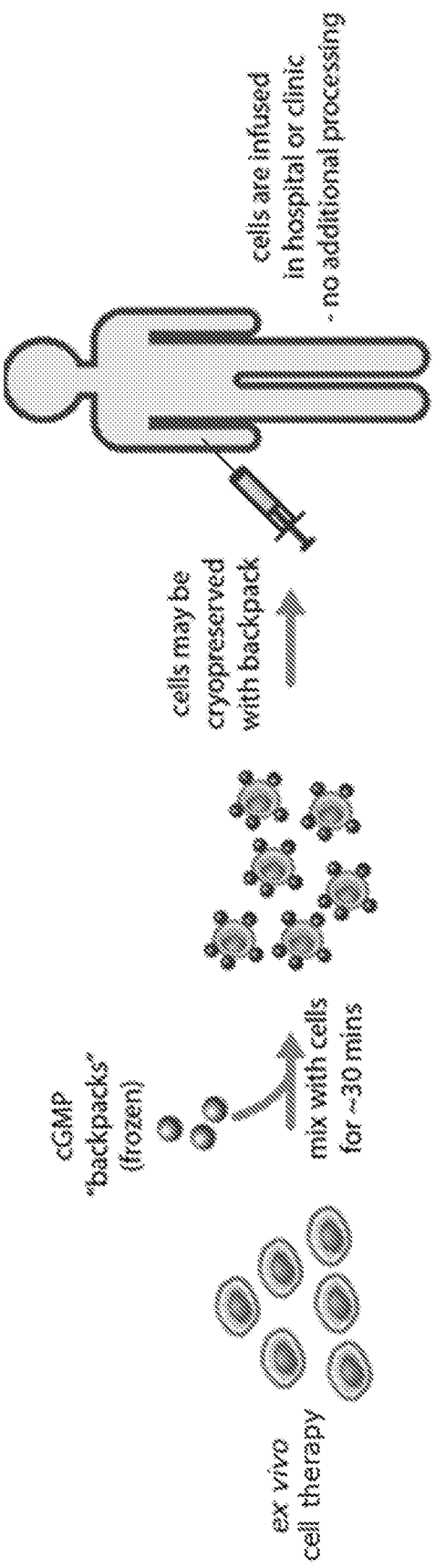

In some embodiments, once prepared and purified, the backpacks can be optionally frozen until use in cell therapy, as illustrated in FIG. 1C. The cell therapy can be selected from, e.g., an adoptive cell therapy, CAR-T cell therapy, engineered TCR T cell therapy, a tumor infiltrating lymphocyte therapy, an antigen-trained T cell therapy, or an enriched antigen-specific T cell therapy.

In various embodiments, a cell therapy composition can be prepared by providing the protein cluster or backpack composition disclosed herein, and incubating the protein cluster or backpack composition with nucleated cells such as immune cells, preferably for about 30-60 minutes. The cells can be cryopreserved with backpacks until administration to a patient via, e.g., infusion.

Also disclosed herein is a cell therapy composition, comprising the protein cluster or backpack composition disclosed herein, associated with a nucleated cell such as T and NK cells. Such cell therapy composition may be administered into a subject in need thereof. Upon administration, the cross-linkers can degrade under physiological conditions so as to release the therapeutic protein monomers from the protein cluster.

Compositions, including pharmaceutical compositions, comprising the backpacks are provided herein. A composition can be formulated in pharmaceutically-acceptable amounts and in pharmaceutically-acceptable compositions. The term "pharmaceutically acceptable" means a non-toxic material that does not interfere with the effectiveness of the biological activity of the active ingredients (e.g., biologically-active proteins of the nanoparticles). Such compositions may, in some embodiments, contain salts, buffering agents, preservatives, and optionally other therapeutic agents. Pharmaceutical compositions also may contain, in some embodiments, suitable preservatives. Pharmaceutical compositions may, in some embodiments, be presented in unit dosage form and may be prepared by any of the methods well-known in the art of pharmacy. Pharmaceutical compositions suitable for parenteral administration, in some embodiments, comprise a sterile aqueous or non-aqueous preparation of the nanoparticles, which is, in some embodiments, isotonic with the blood of the recipient subject. This preparation may be formulated according to known methods. A sterile injectable preparation also may be a sterile injectable solution or suspension in a non-toxic parenterally-acceptable diluent or solvent.

The backpacks and compositions containing such have numerous therapeutic utilities, including, e.g., the treatment of cancers, autoimmune diseases and infectious diseases. Methods described herein include treating a cancer in a subject by using backpacks or backpacked cells as described herein. Also provided are methods for reducing or ameliorating a symptom of a cancer in a subject, as well as methods for inhibiting the growth of a cancer and/or killing one or more cancer cells. In embodiments, the methods described herein decrease the size of a tumor and/or decrease the number of cancer cells in a subject administered with a described herein or a pharmaceutical composition described herein.

In embodiments, the cancer is a hematological cancer. In embodiments, the hematological cancer is leukemia or lymphoma. As used herein, a "hematologic cancer" refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sézary syndrome, Waldenstrom macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof In embodiments, the backpacks or backpacked cells are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or backpacks) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

In embodiments, the backpacks or backpacked cells are administered to the subject parenterally. In embodiments, the cells are administered to the subject intravenously, subcutaneously, intratumorally, intranodally, intramuscularly, intradermally, or intraperitoneally. In embodiments, the cells are administered, e.g., injected, directly into a tumor or lymph node. In embodiments, the cells are administered as an infusion (e.g., as described in Rosenberg et al., New Eng. J. of Med. 319:1676, 1988) or an intravenous push. In embodiments, the cells are administered as an injectable depot formulation.

In embodiments, the subject is a mammal. In embodiments, the subject is a human, monkey, pig, dog, cat, cow, sheep, goat, rabbit, rat, or mouse. In embodiments, the subject is a human. In embodiments, the subject is a pediatric subject, e.g., less than 18 years of age, e.g., less than 17, 16, 15, 14, 13, 12, 11, 10, 9, 8, 7, 6, 5, 4, 3, 2, 1 or less years of age. In embodiments, the subject is an adult, e.g., at least 18 years of age, e.g., at least 19, 20, 21, 22, 23, 24, 25, 25-30, 30-35, 35-40, 40-50, 50-60, 60-70, 70-80, or 80-90 years of age.

EXAMPLES

Example 1

Synthesis of Linker-1

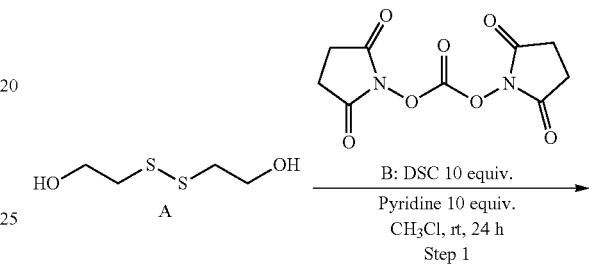

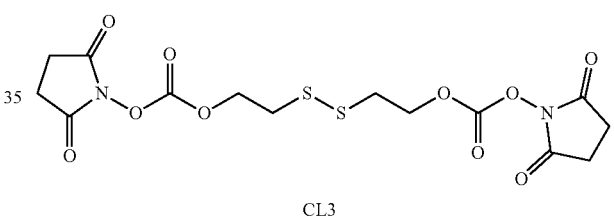

CL3

Carbonate Formation

A: 2,2'-disulfanediyldi(etha n-1-ol)(2.0 g, 1 equiv.)

B: DSC (N,N'-Disuccinimidyl carbonate) (33.2 g, 10.0 equiv.)

Pyridine (11.3 mL, 10.0 equiv.)

CHCl$_3$, r.t., 24 h (1) Stir a solution of 2,2'-disulfanediyldi (etha n-1-ol) (2.0 g, 12.98 mmol, 1 equiv.), in chloroform (333 mL, 165 V)

(2) Add DSC (33.2 g, 12.98 mmol, 10.0 equiv.)

(3) Add Pyridine (11.3 mL, 12.98 mmol, 10.0 equiv.)

(4) Stir reaction mixture at room temperature for 24 h (TLC control)

(5) Concentrate reaction mixture under reduced pressure to produce a semi solid (6) Dilute semi solid with ethyl acetate (200 mL) and wash with water (2×200 mL)

(7) Concentrate the organic layer under reduced pressure to produce a white solid (2.4 g, impure)

(8) Purify white solid by DCM to yield product (60% yield)

HPLC purity-96.75%. $^1$HNMR contains 1.63% DCM

Example 2

Synthesis of Linker-2

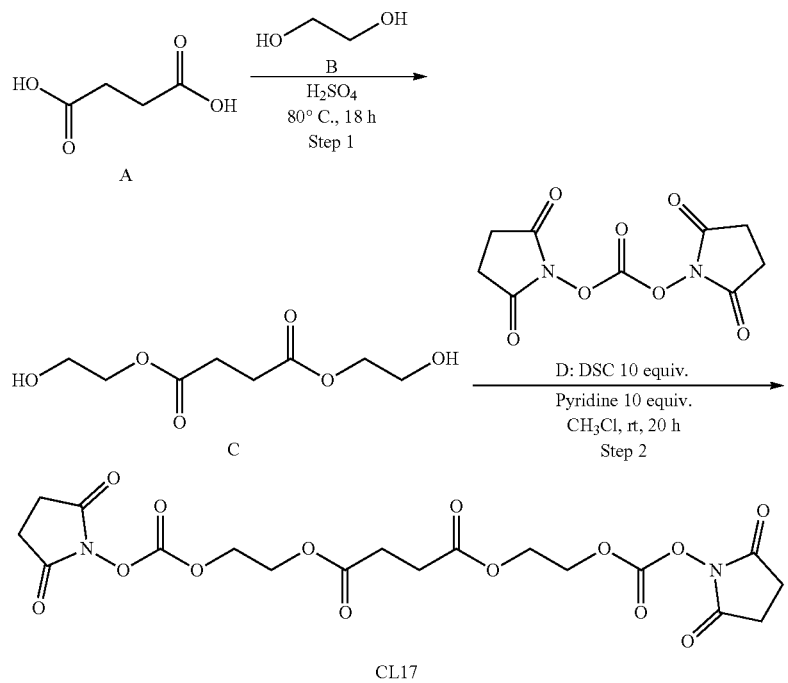

CL17

Step:1 (Ester Formation)
A: Succinic acid (5.0 g, 1 equiv.)
B: Mono Ethylene Glycol (10 V)
$H_2SO_4$ (35 drops)
80° C., 18 h
 (1) To succinic acid (A) (5.0 g, 42.34 mmol, 1 equiv.) at room temperature
 (2) Add Mono Ethylene Glycol (B) (50 mL)
 (3) Add $H_2SO_4$ (35 drops)
 (4) Heat resulting reaction mixture to 80° C. for 18 h (TLC control)
 (5) Cool to room temperature
 (6) Neutralize with sodium bicarbonate (pH~7-8)
 (7) Purify crude material by column chromatography; Elute desired compound with ethyl acetate
 (8) Result is a colorless liquid C: (bis(2-hydroxyethyl) butanedioate) (3.96 g, 45.36% yield)

Step:2 (Carbonate Formation)
C: Bis(2-hydroxyethyl) butanedioate (1.5 g, 1 equiv.)
D: DSC (18.66 g, 10 equiv.)
pyridine (5.76 g, 10 equiv.)
$CHCl_3$, r.t., 20 h
 (1) Stir solution of bis(2-hydroxyethyl) butanedioate (C) (1.5g, 1 equiv., 7.2 mmol) in $CHCl_3$ (150 mL, 100 V)
 (2) Add DSC (D) (18.66 g, 72.74 mmol, 10 equiv.)
 (3) Add pyridine (5.76 g, 72.74 mmol, 10 equiv.)
 (4) Stir reaction mixture at room temperature for 20 h (TLC control)
 (5) Concentrate reaction mixture under reduced pressure
 (6) Dilute with DCM and wash with water (2×300 mL)
 (7) Separate organic layer and dry over anhydrous sodium sulfate
 (8) Concentrate under reduced pressure to produce 1.9 g off white semi solid,
 (9) Lyophilize
 (10) 1.9 g (impure) compound was triturated with DCM: Methanol to afford 1.06 g of off white solid

Example 3

Backpacking of Immune Cells

Purpose: Human cells (e.g., Tcells, CAR-T, NK cells, other immune cells) can be labeled with 5 concentrations of IL15 backpack in HBSS at a cell concentration of 50 M/mL. After labeling the cells can be tested for:
 a. Viability via 7-AAD staining measured by FACS
 b. Expansion in culture via counting beads measured by FACS
 c. Backpack surface labeling via antibodies against IL15 and human anti-IgG Thawing of IL15 Backpacks:

Backpacks should be stored at −80C before use. Thawed backpacks can be re-frozen and re-used up to 3 or more freeze/thaw cycles.

Take backpack aliquots out of the freezer, and thaw them on ice.
 1. After BP solution is thawed, let it warm up to room temperature 15min prior to cell labeling experiments
 2. Adjust the BP stock solution to a final working solution of 3 mg/mL with HBSS

| | [BP] stock (mg/mL) | [BP] working conc. (mg/mL) | BP stock needed (uL) | HBBS needed (uL) | Total vol of BP working sol (uL) |
|---|---|---|---|---|---|
| CYT15 | 4.2 | 3 | 100 | 40 | 140 |

Backpack Dilution and Cell Labeling:

7 reactions total: one PBS only control, one soluble IL15 constant control added to cells after plating), and five backpack samples to be done in triplicate (21 samples total). The backpack samples are:
   a. BP-Dose1: 3 mg/mL
   b. BP-Dose2: 1.5 mg/mL
   c. BP-Dose3: 0.75 mg/mL
   d. BP-Dose 4: 0.375 mg/mL
   e. BP-Dose 5: 0.1875 mg/mL
 1. Make serial dilutions of backpacks in round-bottom 96-well plate:

| Backpack Dose | Concentration | Volume HBSS (>3x) | Volume of Previous Dose (>3x) |
|---|---|---|---|
| Dose 1 | 3 mg/mL | NA | 60 ul stock |
| Dose 2 | 1.5 mg/mL | 60 ul | 60 ul of stock |
| Dose 3 | 0.75 mg/mL | 60 ul | 60 ul of Dose 2 |
| Dose 4 | 0.375 mg/mL | 60 ul | 60 ul of Dose 3 |
| Dose 5 | 0.1875 mg/mL | 60 ul | 60 ul Dose 4 |
| PBS control | 0 | 60 ul | NA |
| Soluble IL15 control | 0 | 60 ul | NA |

2. Distribute 10 ul of diluted backpack from each well above into three wells in a round-bottom 96-well plate (backpacking in triplicate)-21 wells total. NOTE: Round-bottom plates are preferable to V-bottom as they limit backpack toxicity Cell Washing and Backpacking:

The buffers, PBS, and media used in the steps below should be pre-warmed to 37° C.
 1. Collect $30 \times 10^6$ cells from culture and pellet them at 500 g for 5 minutes
 2. Remove cell supernatant by aspiration.
 3. Wash cells by resuspending the pellet in 10 mL pre-warmed (37° C.) HBSS buffer and count by Cellometer (with AOPI dye) or Trypan Blue.
 4. Centrifuge at 500 g for 5 min
 5. Aspirate supernatant and suspend cell pellet in pre-warmed (37° C.) HBSS to a concentration of $100 \times 10^6$/mL cells (approximately 300 ul of buffer)
 6. Pipet 10 ul of cells into each well with backpacks or HBSS and gently mix them by pipetting.

| Samples | Cell # | Cell Vol (ul) | BP Vol (ul) | Final BP Conc. (mg/mL) | HBSS (uL) | Final vol. (uL) |
|---|---|---|---|---|---|---|
| Dose 1 | $1 \times 10^6$ | 10 | 10 | 1.5 | 0 | 20 |
| Dose 2 | $1 \times 10^6$ | 10 | 10 | 0.75 | 0 | 20 |
| Dose 3 | $1 \times 10^6$ | 10 | 10 | 0.375 | 0 | 20 |
| Dose 4 | $1 \times 10^6$ | 10 | 10 | 0.188 | 0 | 20 |
| Dose 5 | $1 \times 10^6$ | 10 | 10 | 0.094 | 0 | 20 |
| PBS | $1 \times 10^6$ | 10 | 0 | 0 | 10 | 20 |
| Soluble IL15 | $1 \times 10^6$ | 10 | 0 | 0 | 10 | 20 |

7. Cover plate with a microfilm to prevent evaporation, and incubate in the cell culture incubator (typically 37° C. with 5% $CO_2$ or what is best for culture).
 8. Incubate cells for one hour at 37° C.
 9. Add 180 uL pre-warmed complete cell media (with serum) to each well.
 10. Pellet cells at 500 g for 5 min, and aspirate media with a multiwell manifold
 11. Wash cells two more times with 200 uL full media, pellet cells, and aspirate supernatant as in steps 9 and 10.
 12. After the third wash, resuspend cells from each sample in 200 uL full media. The cells should be at $\sim 5 \times 10^6$ cells/mL density and need to be further diluted by 1:10 during plating.
 13. Dilute cells 1:10 by transferring 20 ul of cell suspension from the 96-well U bottom to 96-well flat-bottom tissue culture plate and then adding 180 ul cell media (without added cytokines) to achieve a final plating density of $5 \times 10^5$ cells/mL.
 14. Repeat step 13 three additional times in three separate 96-well flat bottom plates (4 plates total: Day0, Day1, Day3, DayX for splitting for future time points)

NOTE:
   a. It is typical to plate several "splits" of cells into multiple 96-well pates which allows individual splits to be analyzed at different time points while allowing for continued propagation in other plates, hence the 4 plates of Day0, Day1, Day3, DayX.
   b. When cells grow too confluent, on DayX, they need to be passaged. We recommend passaging the cells by direct media dilution. For example, on DayX, take the 96-well plate out of the incubator. Resuspend the cells in media by pipetting up and down. Transfer 40 uL of cell solution to a new 96-well flat bottom plate, add 160 uL of fresh, warm media to each well to make a 1:5 splitting.
 15. Add soluble IL15 monomers to soluble IL15 constant control wells of each plate.

Cell Count and Viability Test:

Cells are counted using 7-AAD and CountBright counting beads on flow cytometer.
 1. At each time point, take a 96-well flat bottom plate out of the incubator, resuspend cells in media by pipetting up and down
 2. Transfer 20 uL of cell solution to a 96-well V-bottom plate
 3. To each well, add 20 uL of "CountBright Bead solution".
   CountBright Bead Solution contains (volumes for labeling 1 well is listed below):
   a. 19.6 ul CountBright bead stock
   b. 0.4 ul of 100×7AAD (7-AAD, LifeTech, A1310, 10 ug/mL is 100×)
 4. Repeat these steps on days 1, 3 and X after culturing to assess viability and expansion.

BP Loading Efficiency Test by Surface Staining:

Analyze surface levels of IL-15 backpacks by flow cytometry on Days 0 and Day 1 using anti-IL15 and anti-human IgG antibodies.
 1. Take a 96-well flat bottom plate out of the incubator, resuspend cells in media by pipetting up and down
 2. Transfer 100 uL of cell solution to a new V-bottom 96-well plate (this should contain 50,000 cells)
 3. Pellet cells (500 g for 5 min) and aspirate supernatant
 4. Resuspend cells in 40 uL "Antibody Cell Surface Staining Solution"
   Antibody Staining Solution (volumes for labeling 1 well is listed below):

a. 0.4 uL of Mouse anti-human IgG BV421—Biolegend cat. no. 409318, 1:100 dilution
b. 0.4 uL of Anti-IL15 PE: R&D Systems cat. no. IC2471IP, 1:100 dilution
c. 0.4 uL of 100×7AAD (7-AAD, LifeTech, A1310, 10 ug/mL is 100×)
d. 38.8 uL of MACS buffer
5. Incubate cells for 10 min at room temperature
6. Add 160 uL of cold MACS buffer to each well, pellet cells at 500 g for 5 min, aspirate.
7. Wash cells one additional time with 200 uL cold MACS buffer
8. Resuspend in 30 uL per well of MACS buffer and analyze on flow cytometer (HTS mode)

Reagents Used:
Hank's Balanced Salt Solution (HBSS, Gibco, with calcium and magnesium. cat #14025-092)
Phosphate-Buffered Saline (PBS, Gibco, no calcium, no magnesium, cat #10010-023)
Round-bottom 96-well plate (Granier-Bio, clear, sterile, polypropylene plates, cat #650261)
v-bottom 96-well plate (optional but recommended): Costar 3894
Plat-bottom 96-well plate (FisherSci, cat #353072)
Counting Beads (LifeTech, CountBright Absolute Counting Beads, cat #C036950)
7-aminoactinotnycin-D (7-AAD, LifeTech, cat #A1310)
Human 11,-15 PE-Conjugated Antibody (R&D Systems, cat #IC2471P)
Mouse anti-Human IgG, BV421 (Biolegend. cat #409318)
Alternative Ab: Mouse anti-Human IgG, APC (Biolegend, cat #409306)
Alternative Ab: Donkey anti-Human IgG (H+L), DyLight 650 (ThermoFisher, cat #SA5-10129)
MACS Buffer (optional):
    EDTA: LifeTechnologies, 15575-038
    Phosphate-Buffered Saline, pH 7.4 (same as above)
    Bovine Serum Albumin (BSA): AmericanBio, Inc. cat #AB01243-00050

Example 4

IL-15 Backpack Provides Autocrine Stimulation and Expansion of T Cells After Adoptive Transfer Driven by Controlled Concentrated Release of IL-15

Interleukin 15, a powerful stimulator of CD8 and NK cell expansion is capable of driving anti-tumor activity of adoptively transferred T cells. However, systemic delivery does not safely provide sufficient doses to drive T cell expansion engraftment and anti-tumor activity.

Our interleukin 15 backpack (IL-15 backpack) program was initiated with the aim of providing safe and effective doses of Interleukin 15 (IL-15)) by loading transferred T cells with an autocrine source of the cytokine (Stephan et al., Therapeutic cell engineering with surface-conjugated synthetic nanoparticles. Nat. Med. (2010) 16(9):1035-1041). High levels of IL-15 in the blood of cancer patients is associated with successful clinical responses (Kochenderfer et al., Lymphoma remissions caused by anti-CD19 chimeric antigen receptor T cells are associated with high serum interleukin-15 levels. J. Clinical Oncology (2017) 35(16): 1803-1813).

The IL-15 backpack primed T-cells disclosed herein are autologous T cells that carry tightly controlled doses of IL-15, which is slowly released over a 7-14 day period for directed autocrine activation of infused T cells without affecting endogenous T cells.

One example is IL-15 backpack primed cytotoxic T cells (CTLs) that are tumor antigen primed using a novel dendritic cell priming sequence. We have developed a fully closed manufacturing process to produce autologous T cells, with tightly controlled loading of IL-15 backpack on these cells, at high yields of reactive cells, and with cell numbers exceeding one billion per apheresis.

Figure 2:
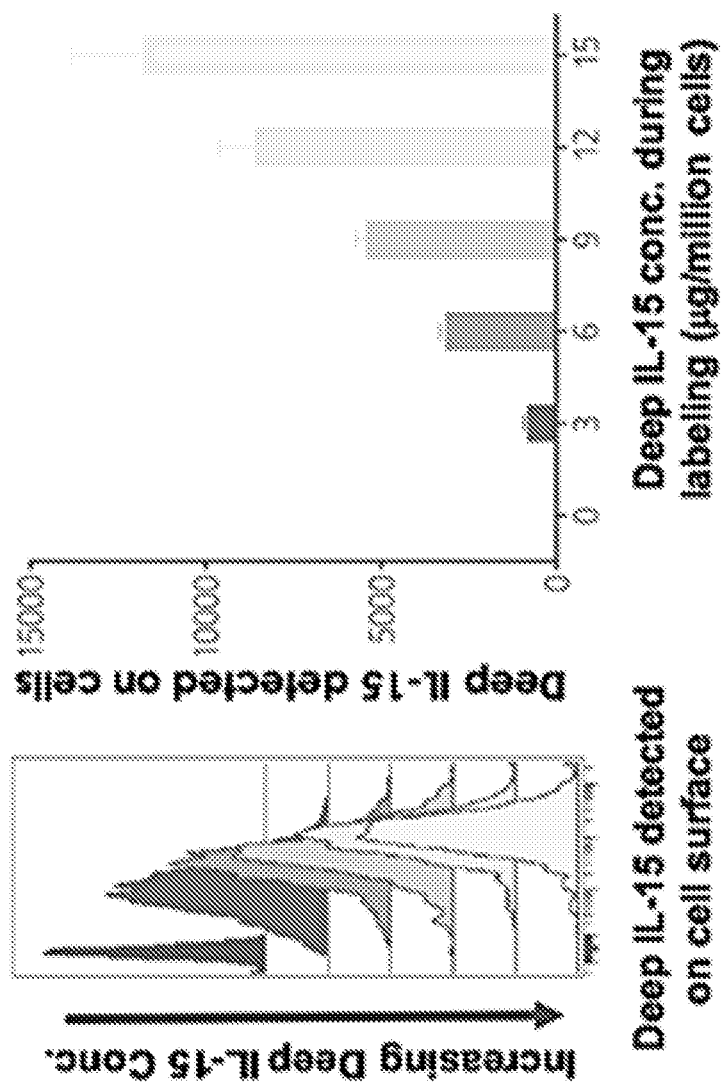
FIG. 2: Titratable loading of IL-15 backpack on human T cells.

As shown in FIG. 2, fluorophore-containing IL-15 backpacks were titrated in a cell labeling reaction using healthy human CD8 T cells. Fluorescent histograms (LHS) and MFI quantification (RHS) show that the extent of IL-15 backpack loading increases with increased IL-15 backpack loading concentration.

Figure 3:
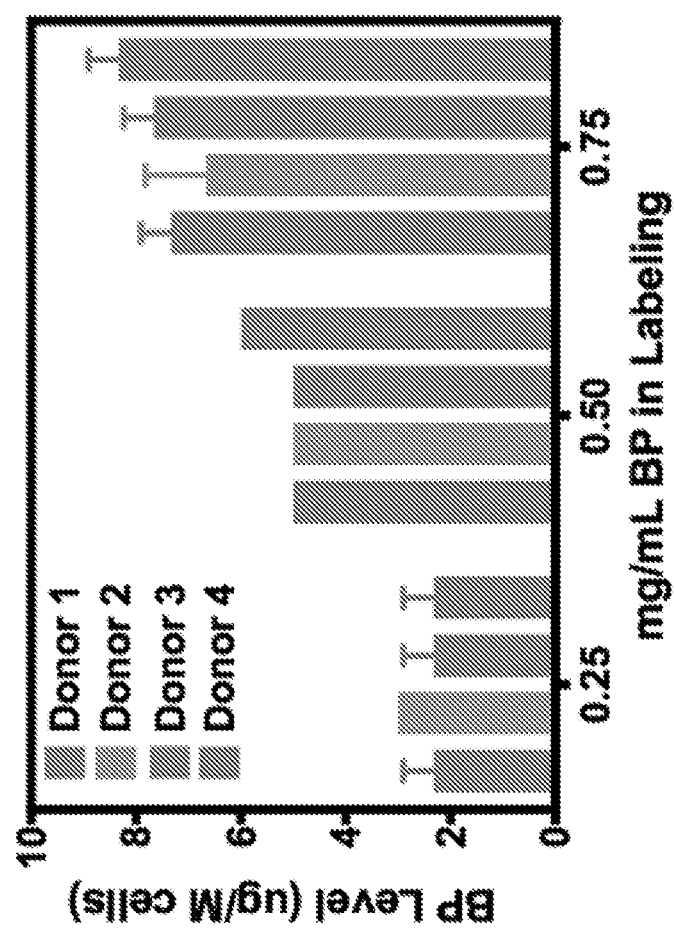
FIG. 3: Consistent and precise loading of IL-15 backpack across multiple donors.

FIG. 3 shows dynabead-activated human CD3 T cells from four healthy donors were labeled with IL-15 backpack at three different concentrations. Cell-associated IL-15 backpack loading was assessed by quantifying the remaining IL-15 backpack from the labeling reaction and subtracting that number from the total amount of IL-15 backpack added in the reaction.

Figure 4:
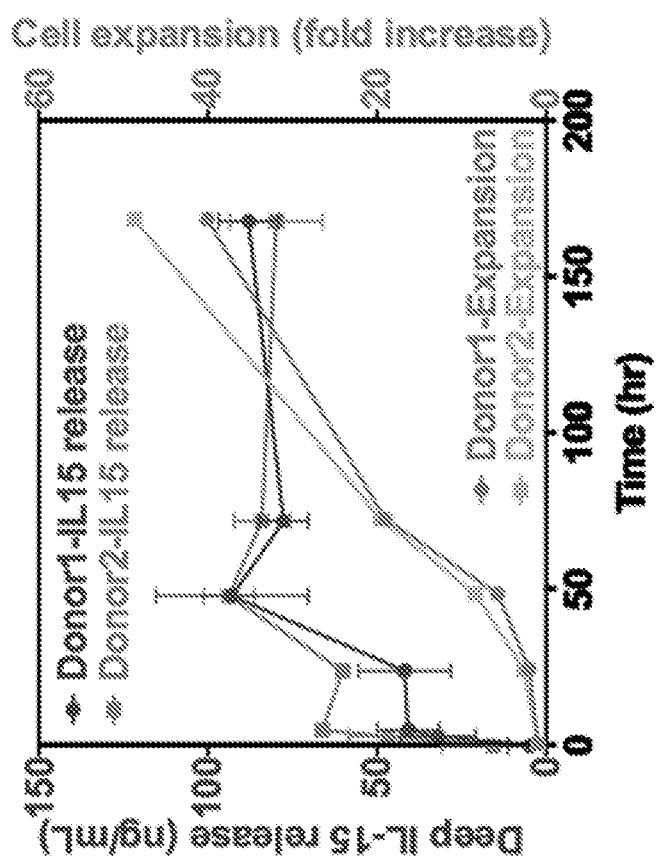
FIG. 4: IL-15 backpack release from labeled cells drives expansion.

FIG. 4 shows dynabead-activated human CD3 cells were treated with or without IL-15 backpack before culturing for 7 days. IL-15 levels in the culture supernatants were assessed by ELISA. Expansion was assessed by flow cytometry.

Figure 5:
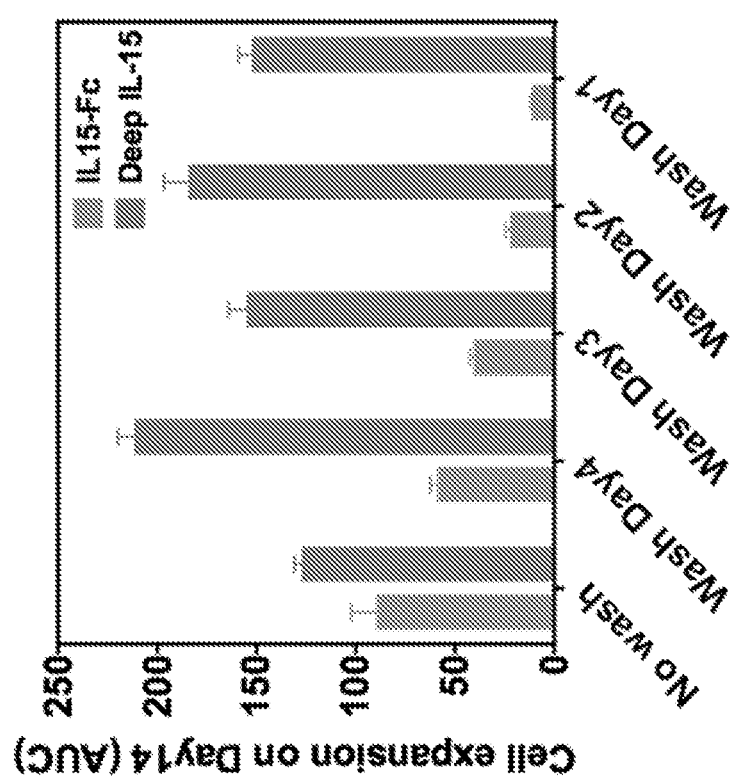
FIG. 5: Cell-associated IL-15 backpack drives cell expansion at Day 14 following intermittent wash.

FIG. 5 shows IL-15 backpack labeled human CD3 T cells were cultured for 14 days. Media exchange was carried out on Day 1, or Day 2, or Day3, or Day4 to remove secreted IL-15.

Figure 6B:
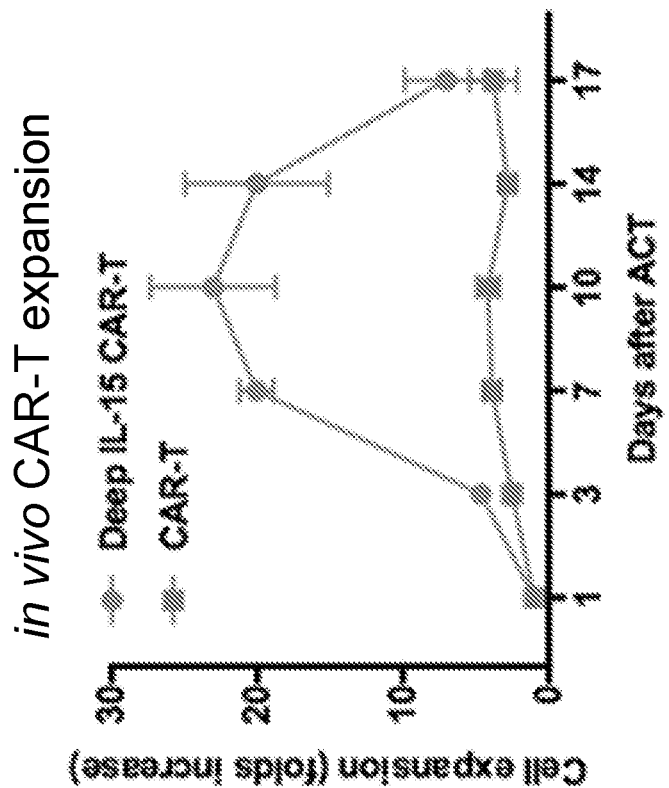
FIGS. 6A-6C: IL-15 backpack drives expansion of anti-EGFR CAR-expressing human CD3 T cells.
Figure 6A:
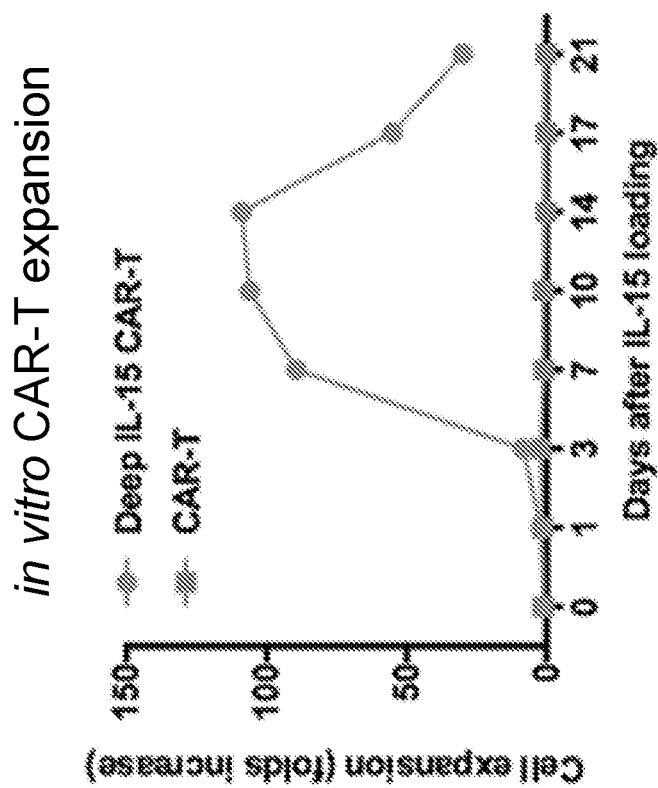
Figure 6C:
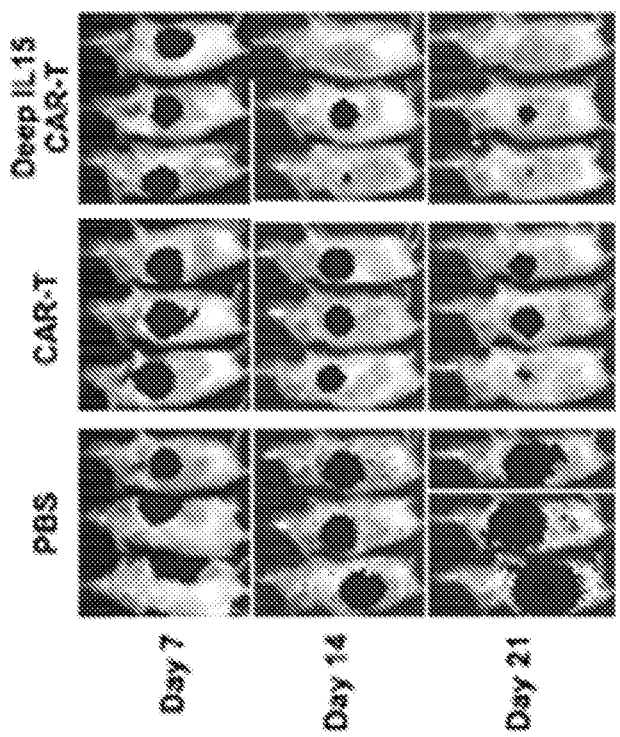

FIG. 6A shows in vitro cell expansion measured by flow cytometry for ±IL-15 backpack loaded CAR-T cells. FIG. 6B shows flow cytometry measured serum levels of CAR-T cells following injection into NSG mice bearing NSCLC tumor. FIG. 6C shows PET imaging of tumor size.

Figure 7A:
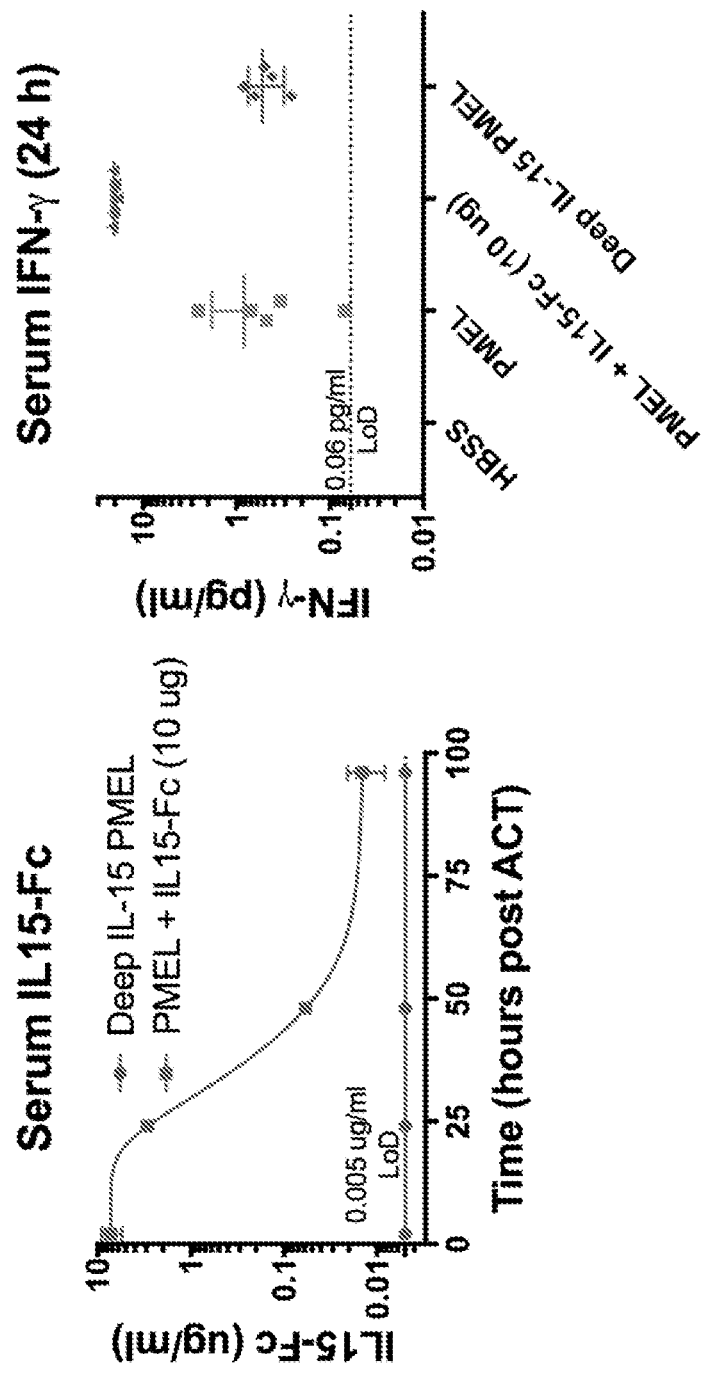
FIGS. 7A-7C: Contrasting effects of systemic IL15-Fc and IL-15 backpack in C57B6 mouse model with intact immune system.
Figure 7B:
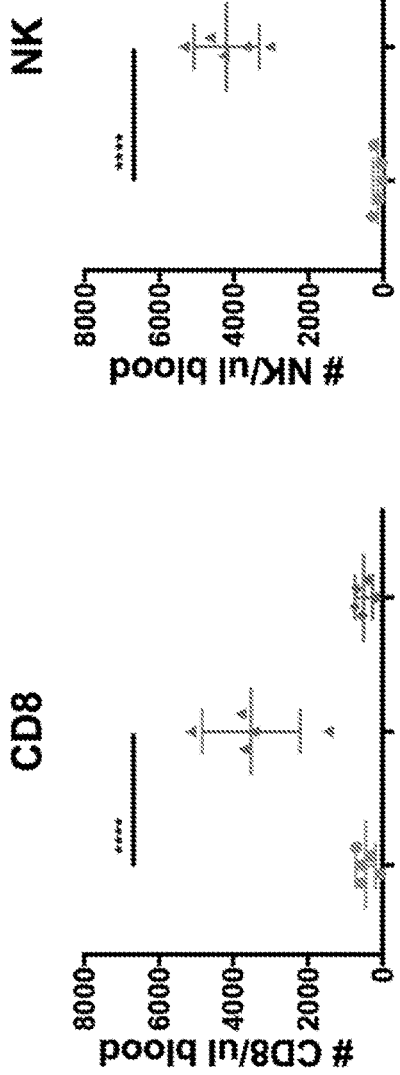
Figure 7B:
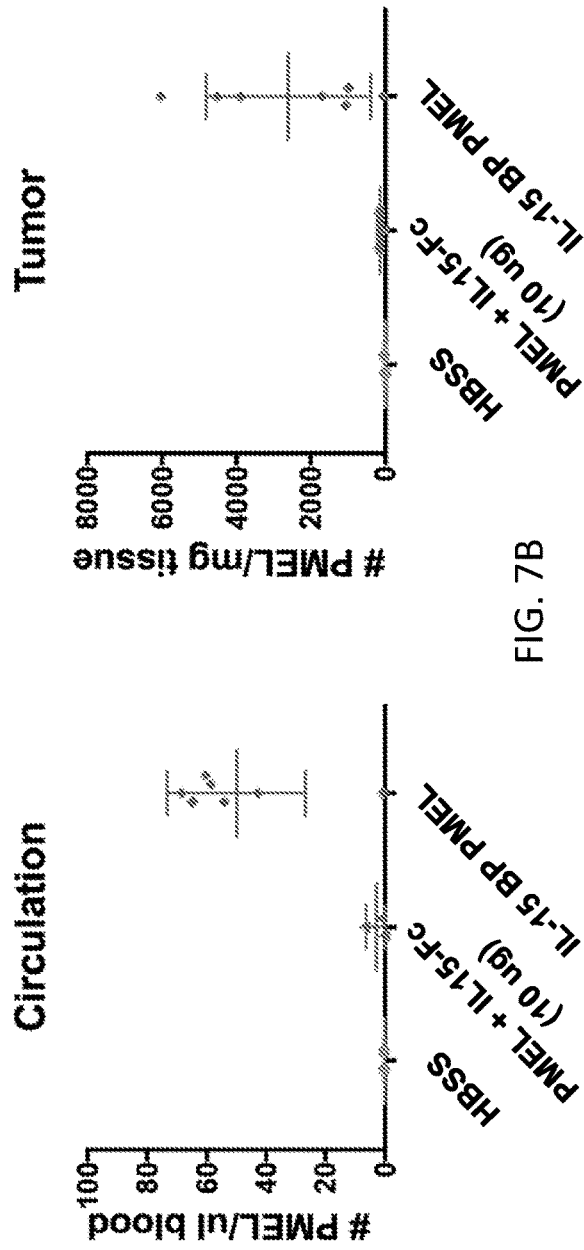
Figure 7C:
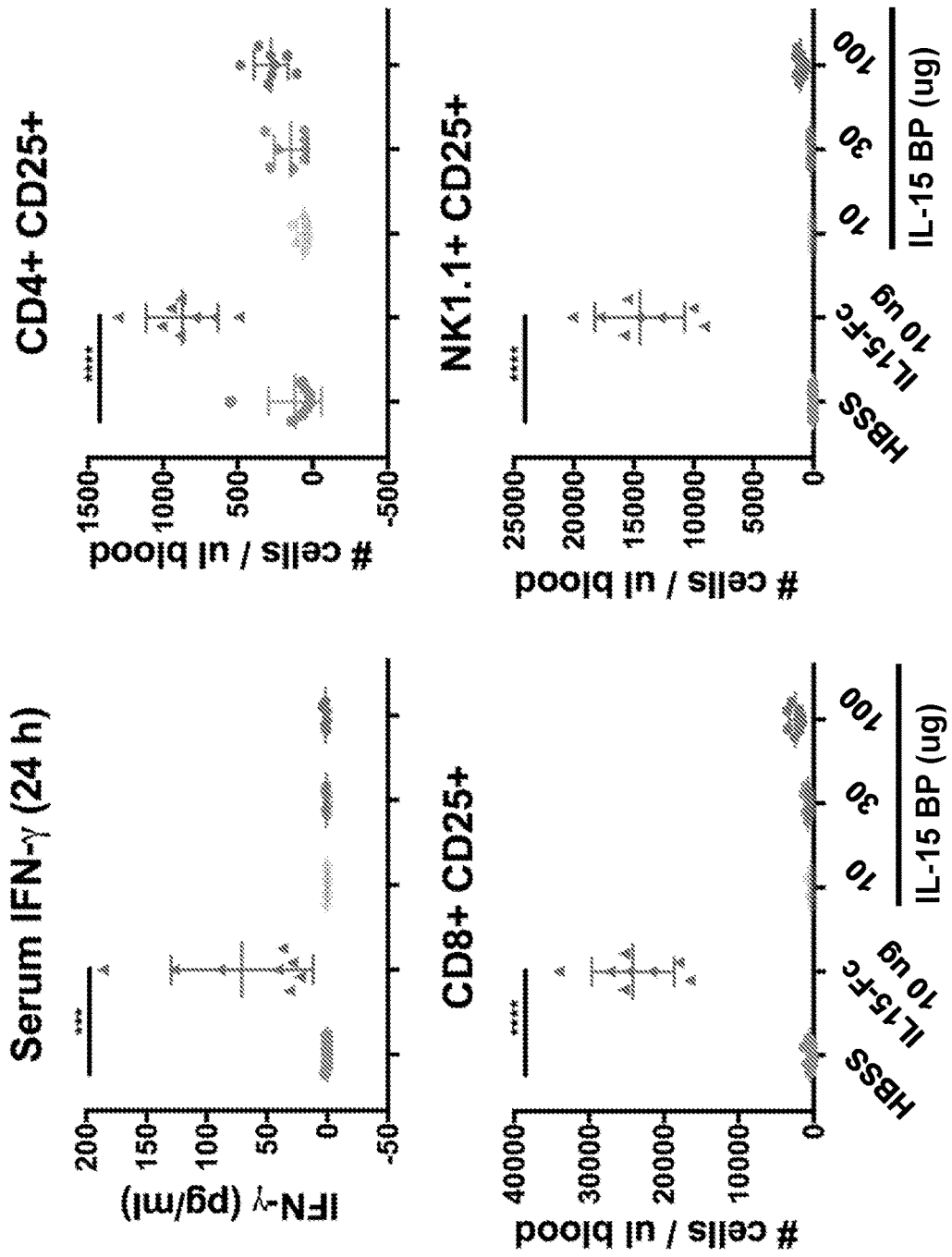
Figure 8A:
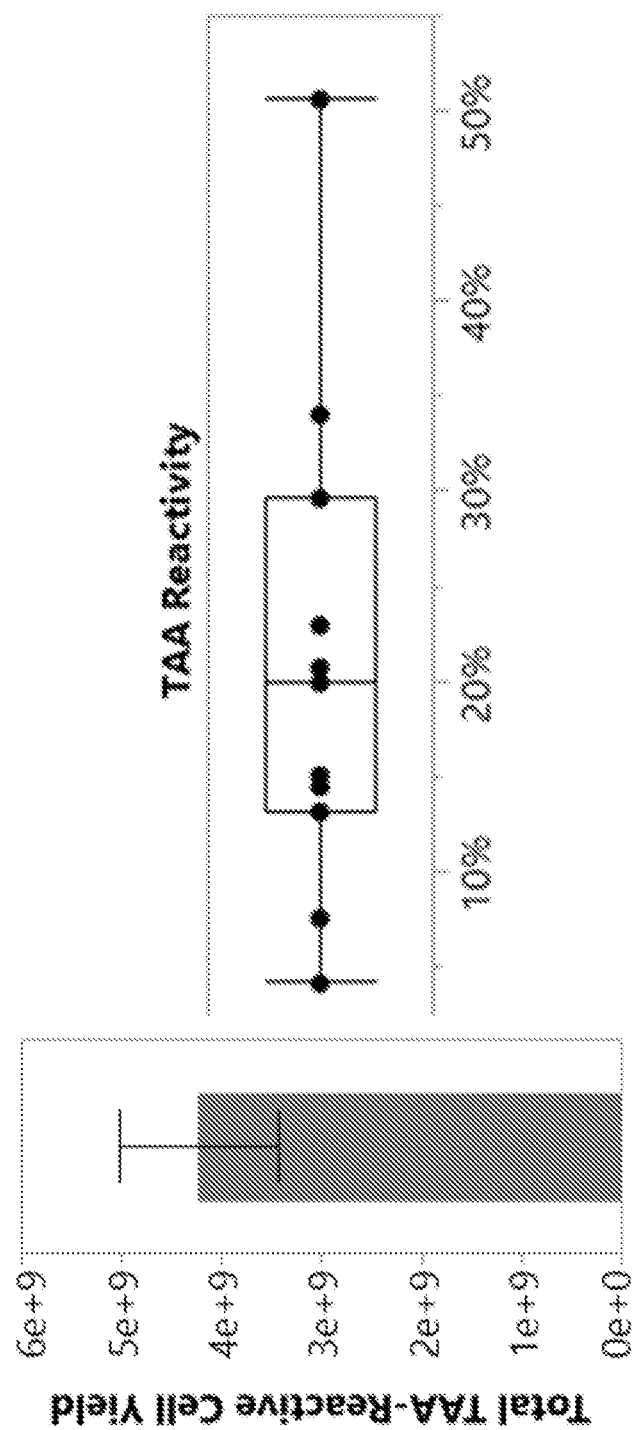
FIGS. 8A-8E: CTLs from process completion were harvested and characterized
Figure 8B:
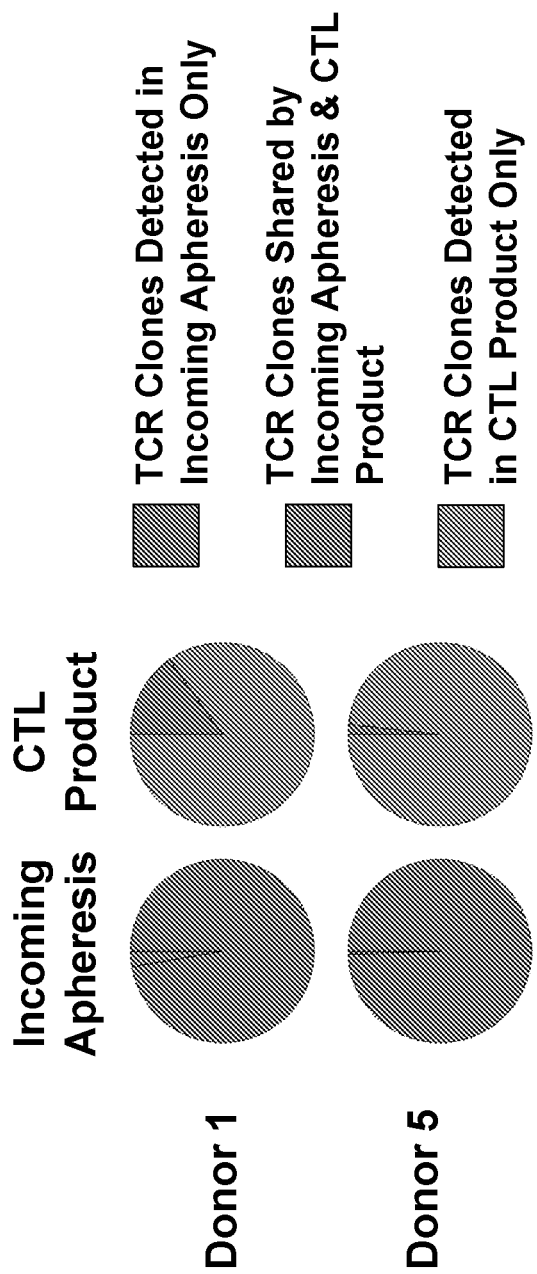
Figure 8C:
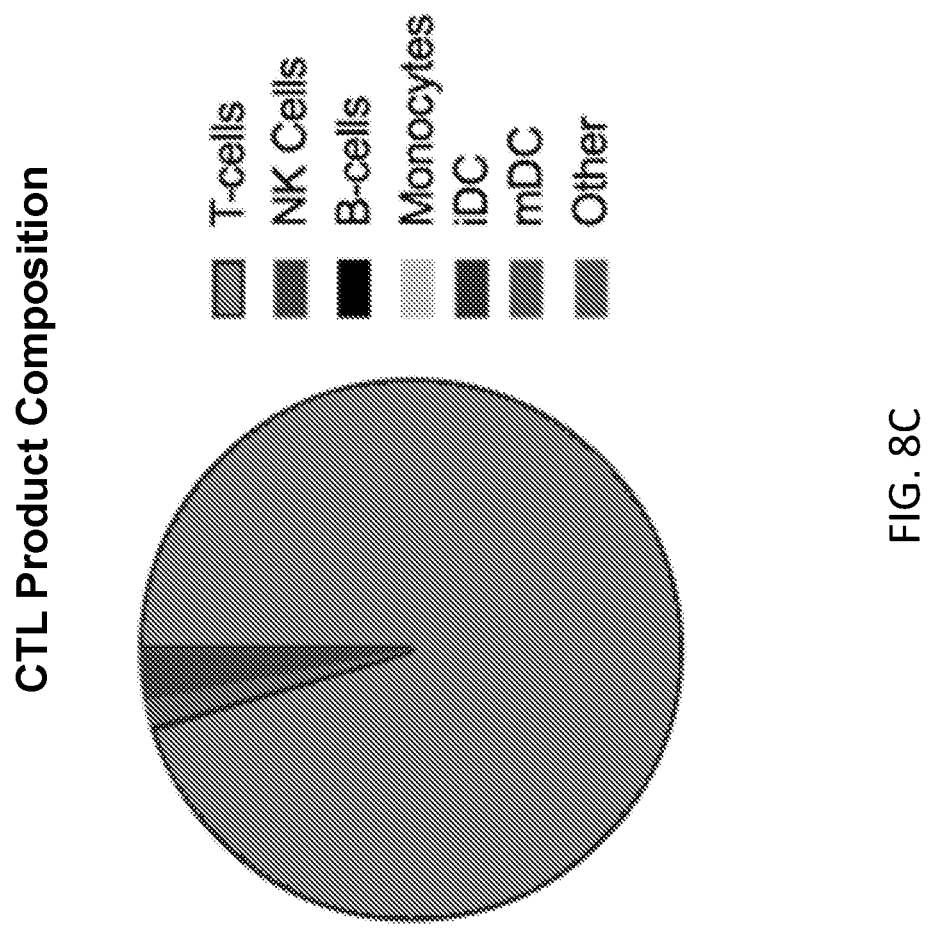
Figure 8E:
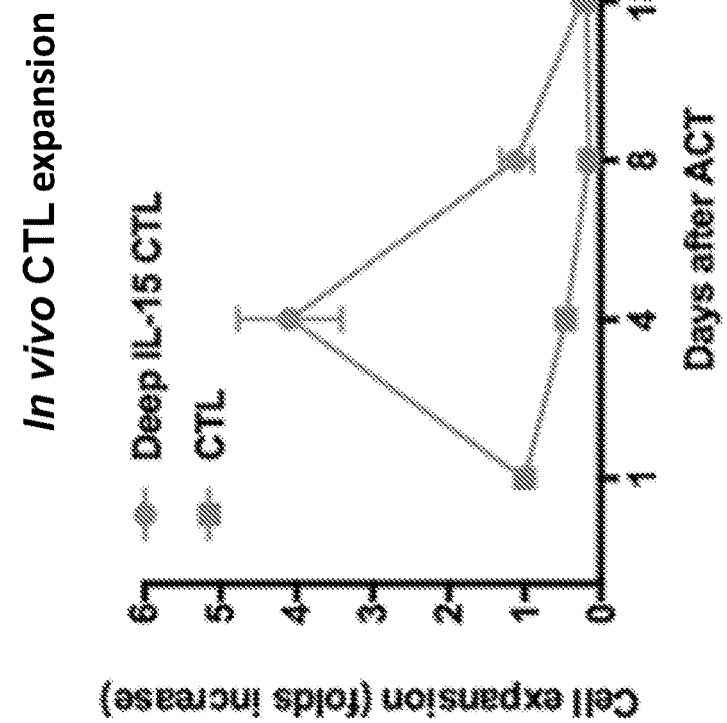
Figure 8D:
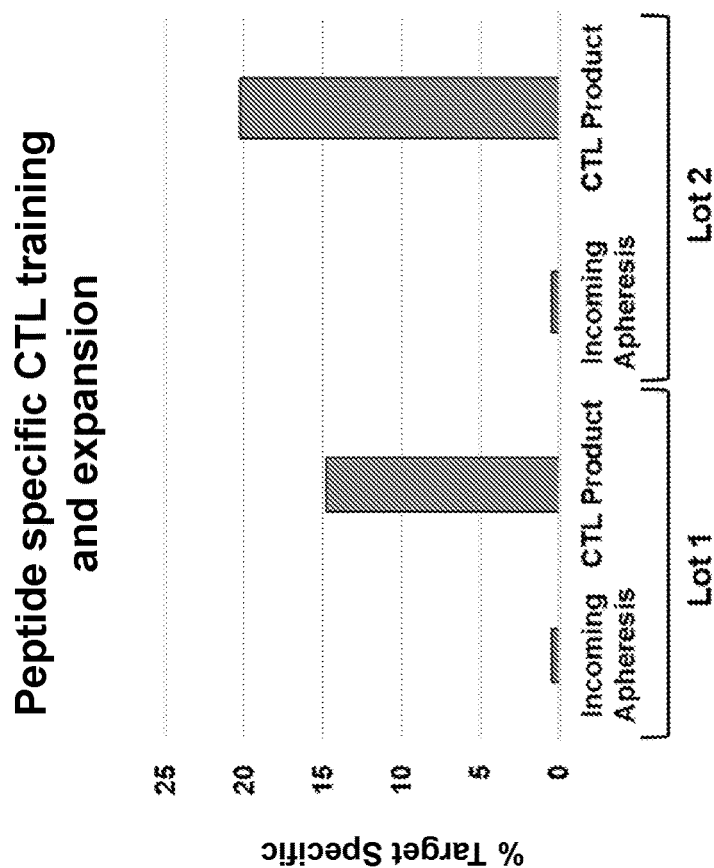

FIGS. 7A-7B shows PMEL T cells, activated ex vivo with anti-CD3/anti-CD28 coated plates and either injected, primed with IL-15 backpack ("IL-15 BP"), or co-administered with IL15-Fc monomers into B16-F10 tumor-bearing C57B6 mice. Mice were sacrificed on days 1, 4, 10 and 16 for blood and tissue collection. Blood was drawn at 2, 24, 48, and 96 hrs for quantification of IL15-Fc (ELISA) and IFN-γ (Luminex) (FIG. 7A), and for enumeration of CD8, NK, and PMEL cells (FIG. 7B, Flow Cytometry). FIG. 7C shows IL15-Fc or IL-15 backpacks were injected into non-tumor bearing C56BL6 mice in the absence of PMEL T cell injection. Blood was drawn for quantification of IFN-γ, and for enumeration of activated (CD25 +) CD4, CD8, and NK cells.

Novel, closed, semi-automated cell manufacturing process with a yield of up to several billion of cytotoxic T lymphocytes (CTLs) that are targeted against a customizable set of tumor-associated antigens (TAAs). In a final step the antigen-directed CTLs are loaded with IL-15 backpack to generate the TRQ15-01 cell product.

FIGS. 8A-8E show that CTLs from process completion were harvested and characterized for: (A) Product TAA-specific cell count and reactivity (intracellular cytokine staining after peptide stimulation); (B) TCR sequencing comparing TRQ15-01 CTL products to their incoming apheresis, and (C) flow-based immune cell composition. (D) TAA-trained CTLs were labeled with an MHC tetramer bearing one of the antigen peptides; (E) CTLs±IL-15 backpack were injected into NSG mice and blood was drawn on days 1, 4, 8, 10. Cell expansion was measured by flow cytometry.

In conclusion, IL-15 backpack cell loading is robust and tunable giving a controlled IL-15 dose per cell. The design of our IL-15 backpack technology provides slow and controllable release of IL-15 resulting in autocrine stimulation and sustained cell expansion in adoptive T cell therapy. In contrast to systemically delivered IL-15, IL-15 backpack Priming induces orders of magnitude lower systemic IFNg levels, endogenous CD8 and NK cell expansion, due to lack of systemic exposure. A fully closed, semi-automated cell process reproducibly generates several billion antigen-directed human CTLs with ~20% reactivity and 95% T cell purity from healthy donors despite ultra low frequency (<1%) precursors. Human CTLs are highly dependent on IL-15 backpack priming technology for cell survival and expansion in vivo.

Example 5

Pharmacological Activity of Deep IL-15 Primed PMEL T Cells

Deep IL-15 refers to a multimer of human IL-15 receptor a-sushi-domain-Fc fusion homodimers with two associated IL-15 molecules (IL15-Fc), connected by a cleavable crosslinker (Linker-2), and non-covalently coated with a polyethylene glycol (PEG)-polylysine$_{30}$ block copolymer (PK30). Specifically, Deep IL-15 is a multimer of human IL15-Fc monomers, connected by a hydrolysable crosslinker (CL17) and non-covalently coated with a polyethylene glycol (PEG)-polylysine$_{30}$ block copolymer (PK30). IL15-Fc monomers consist of two subunits, each consisting of an effector attenuated IgG2 Fc variant fused with an IL-15 receptor α-sushi-domain noncovalently bound to a molecule of IL-15. Deep IL-15 Primed T cells are generated via a loading process in which target cells are co-incubated with Deep IL-15 at high concentrations. Through this process, Deep IL-15 becomes associated with the cell via electrostatic interactions and is internalized to create intracellular reservoirs of Deep IL-15. From these reservoirs, Deep IL-15 slowly releases bioactive IL15-Fc by hydrolysis of the crosslinker. This extended release of IL15-Fc promotes proliferation and survival of Deep IL-15 Primed T cells, providing a targeted, controllable and time-dependent immune stimulus.

The objective of this study was to test the pharmacological activity of Deep IL-15 primed PMEL T cells in C57BL/6J mice with and without orthotopically placed B16-F10 melanoma tumors. Control groups included vehicle control, PMEL cells alone and PMEL cells+IL15-Fc, administered in a separate injection (10 µg, maximum tolerated dose, MTD).
Materials and Methods
B16-F10 Tumor Establishment and Tumor Measurements B16-F10 melanoma tumor cells (0.2×10$^6$) were injected intra-dermally into the shaved right flank of female C57BL/6 mice (Jackson Labs) on study day −12. The body weights were recorded and tumor dimensions (length [L] and width [W], defined in the list of abbreviations) were measured with calipers 2 to 3 times per week. Tumor volumes were calculated using the formula: $W^2 \times L \times \pi/6$.
Isolation and Expansion of PMEL Cells PMEL cells were isolated from the spleens and lymph nodes (inguinal, axillary and cervical) of 14 female transgenic PMEL mice (Jackson Laboratories, Bar Harbor, Me.). The spleens and lymph nodes were processed with a GentleMACS Octo Dissociator (Miltenyi Biotech, Auburn, Calif.) and passed through a 40 µm strainer. The cells were washed by centrifugation and the CD8a+ cells were purified using an IMACS naïve CD8a$^+$ isolation kit (Miltenyi Biotech,) and a MultiMACS cell 24 block (Miltenyi Biotech) and separator (Miltenyi Biotech) with 18 columns following the manufacturer's protocol. The non-CD8a$^+$ cells were removed by an affinity column and the CD8a$^+$ T-cells were collected in the column eluate. The purity of CD8a+ cells was confirmed by flow cytometry.

Upon isolation (DO) purified CD8a$^+$ cells from PMEL mice were plated into ten, 6-well tissue culture plates coated with anti-CD3 and anti-CD28 at a density of 5×10$^6$ cells/well and incubated for 24 hr at 37° C. and 5% CO2. Murine IL-2 (20 ng/mL) and murine IL-7 (0.5 ng/mL) were added 24 hr post plating (D1). On D2 and D3, the cells were counted and diluted to a concentration of 0.2×10$^6$ cells/mL with fresh media containing murine IL-21 (10 ng/mL). The cells were collected on D4 to obtain a total of 100×10$^6$ PMEL cells/mL in 28 mL of vehicle control.
Preparation of Deep IL-15 Primed PMEL T Cells Five mL of PMEL cells (100×10$^6$ cells/mL) were mixed with 5.5 mL of Deep IL-15 (1.36 mg/ml) and incubated with rotation for 1 hr at 37° C. to create Deep IL-15 Primed PMEL cells. Deep IL-15 Primed PMEL cells were washed (3×, first with medium and then twice with HBSS) by centrifugation (500 g) and counted. Deep IL-15 Primed PMEL cells were resuspended at a concentration of 50×10$^6$ cells/mL. The mice in Groups 5A and 5B were injected with 200 µL of this preparation for a total of 10×10$^6$ Deep IL-15 Primed PMEL cells per mouse. PMEL cells (15 mL at 100×10$^6$ cells/mL) were mixed with 15 mL of HBSS, incubated with rotation for 1 hr at 37° C., washed (3×, first with medium and then twice with HBSS) by centrifugation (500 g) and counted. PMEL cells were resuspended at a concentration of 50×10$^6$ cells/mL. The mice in Groups 2A and 2B were injected IV with 200 µL of this preparation for a total of 10×10$^6$ PMEL cells per mouse. The mice in Groups 3A and 3B were injected IV with 200 µL of this preparation for a total of 10×10$^6$ PMEL cells per mouse, and received a retro-orbital injection of IL15-Fc (10 µg/mouse in 50 µl HBSS; lot #TS0). Based on an average loading efficiency of 39%, the total amount of IL15-Fc associated with 10×10$^6$ PMEL cells is 58.5 µg, which is 5.85-fold higher than the amount delivered systemically by injection of IL15-Fc (10 µg) in Groups 3A and 3B.
Fc-IL-15 ELISA An Fc-IL15 Enzyme-Linked Immunosorbent Assay (ELISA) was used to determine the IL15 Fc concentration in the samples collected at 2 hr, D1, 2, 4 and 10 post-dose. ELISA plates (were coated overnight at 4° C. with Goat Anti-human IgG Fc Capture Antibody. Plates were washed and blocked with reagent diluent for at least 2 hours at 30° C. Plates were washed, samples (diluted in reagent diluent)

and IL15-Fc standards (in duplicate, 31 to 2000 pg/mL, in reagent diluent) were added to the wells, and plates were incubated for 1 hour at 37° C. Plates were washed followed by addition of biotin-anti-IL15 detection Antibody was added and incubated for 1 hour at 37° C. Plates were washed and incubated with Streptavidin-HRP for 20 min at 37° C. Plates were washed followed by addition of 3,3',5,5'-Tetramethylbenzidine (TMB) Substrate Solution and incubated for 20 min at room temperature in the dark until the reaction was stopped. Plates were read on a microplate reader (450 nm).

The assay was run twice. For the first run, samples were evaluated at the following dilutions: 1: 20000 for the 2 hr time point, 1:5000 for the D1 time point, and 1:250 for the D2, D4 and D10 time points. For the second run, samples from groups 3A and 3B, were diluted 1:5000 for the D1 time point, 1:250 for the D2 time point and 1:25 for the D4 and D10 time points. Samples from groups 1A and 1B, 2A and 2B and 5A and 5B were diluted 1:25 for all the time points analyzed. The data is reported for the second run. However, because the samples for the 2 hr time point were exhausted for the second run, and given that IL15-Fc concentrations at 24 hr were similar in groups 3A and 3B across the two runs, the 2 hr values from the first run were included with the other data points from the second run for the purpose of calculating pharmacokinetic (PK) parameters.

The lower limit of quantitation (LLOQ) in blood was 310 ng/ml for the 1:20000 dilution, 77.5 ng/ml for the 1:5000 dilution, 3.875 ng/ml for the 1:250 dilution and 0.3875 ng/ml for the 1:25 dilution.

Serum Cytokine Levels in Serum from Mice

ThermoFisher ProcartaPlex mouse high sensitivity panel 5plex Cat. #EPXSOSO-22199-901 kits were used according to manufacturer's protocol and samples were analyzed on a Bio-Plex 200 system. Serum was thawed on ice, and 20 μL of serum were tested for IFN-γ, TNF-α, IL-2, IL-4 and IL-6 levels. In a few samples, 20 μL of serum were not available, so a smaller volume was utilized. Dilution factors were adjusted, to calculate concentrations according to the standard curves. Statistical analysis was carried out in GraphPad Prism.

Results
Clinical Chemistry

Figure 9:
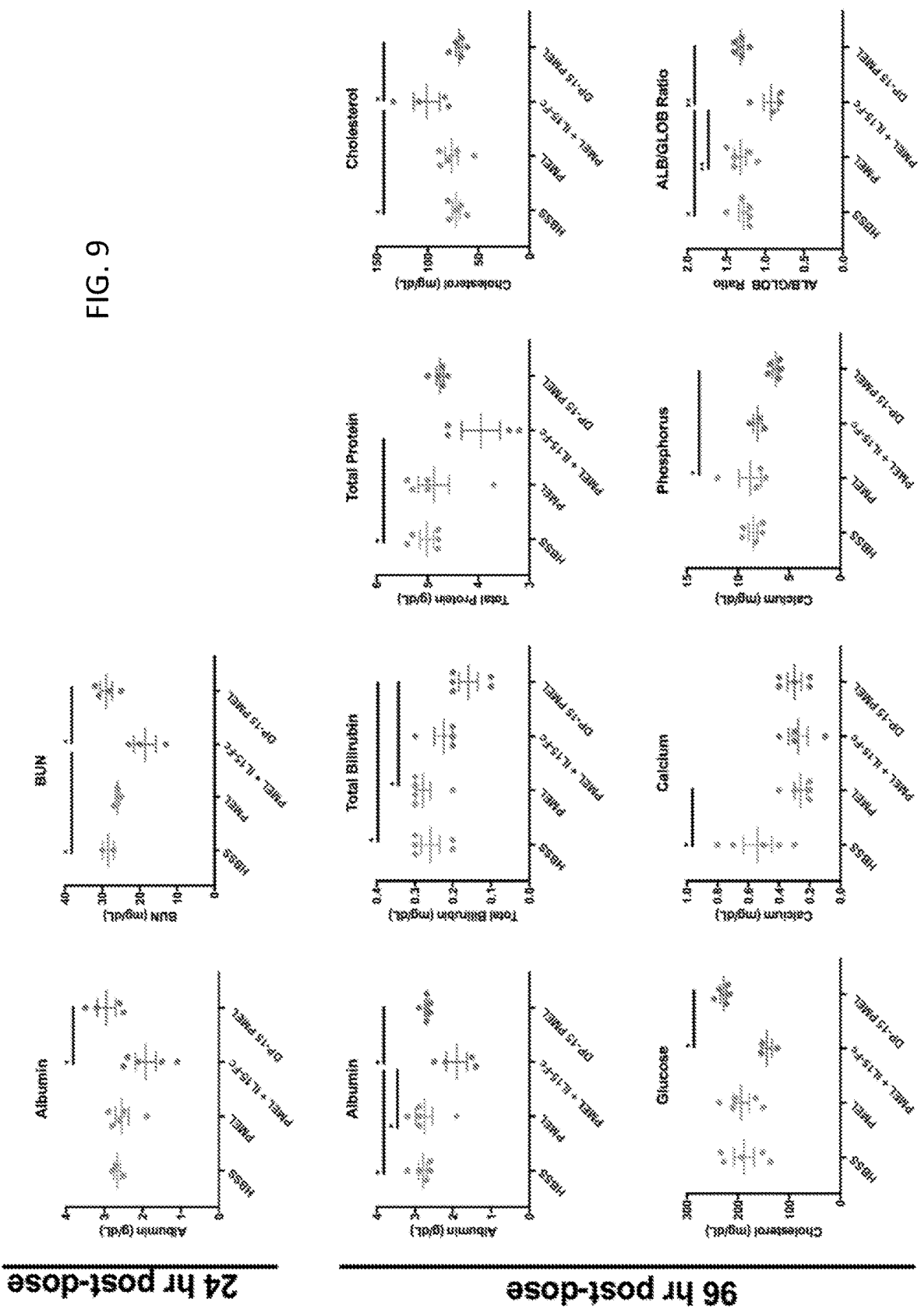
FIG. 9: Clinical chemistry parameters in naive mice at D1 and D4 post-dose. HBSS=vehicle control; DP-15 PMEL=Deep IL-15 Primed PMEL cells; D=Day. Statistical comparisons were made using ANOVA followed by Tukey's multiple comparison test. *=$p<0.05$; =$p<0.01$; *=$p<0.001$; ****=$p<0.0001$.

Clinical chemistry parameters were measured on serum samples. FIG. 9 shows clinical chemistry parameters where statistically significant changes were observed for the naïve mice at D1 and D4 post-dose. At D1 post-dose, a significant reduction ($p<0.05$) in Albumin levels was observed in the PMEL+IL15-Fc group relative to the Deep IL-15 Primed PMEL group as well as in the Blood Urea Nitrogen (BUN) levels compared to both vehicle control and Deep IL-15 Primed PMEL ($p<0.05$ for both). At D4 post-dose, the PMEL+IL15-Fc group showed significantly reduced Albumin ($p<0.05$ compared to all the other treatment groups), total protein ($p<0.05$ compared to vehicle control), Glucose ($p<0.05$ compared to the Deep IL-15 Primed PMEL), Albumin/Globulin (ALB/GLOB) ratio ($p<0.05$ compared to vehicle control, and $p<0.01$ compared to PMEL and Deep IL-15 Primed PMEL). Additionally, the PMEL+IL15-Fc group showed a significant increase ($p<0.05$ compared to vehicle control and Deep IL-15 Primed PMEL) in Cholesterol levels. All treatment groups showed a trend toward a reduction in Calcium levels compared to vehicle control, which was statistically significant with the PMEL group ($p<0.05$). The Deep IL-15 Primed PMEL group showed statistically significant changes in Total Bilirubin ($p<0.05$ compared to vehicle control and PMEL) and Phosphorus ($p<0.05$ compared to PMEL).

Figure 10:
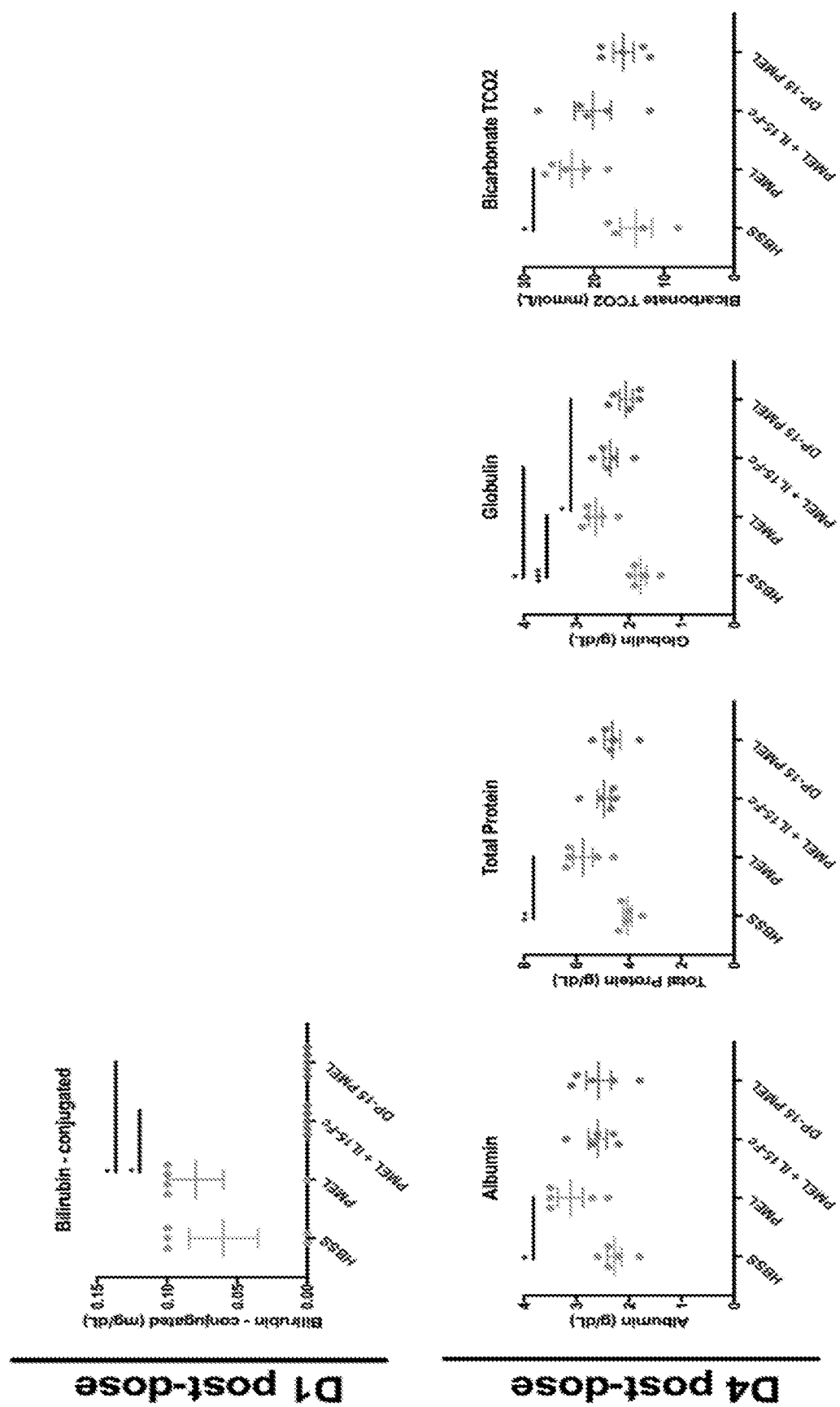
FIG. 10: Clinical chemistry parameters in tumor-bearing mice at D1 and D4 post-dose. HBSS=vehicle control; DP-15 PMEL=Deep IL-15 Primed PMEL cells; D=Day. Statistical comparisons were made using ANOVA followed by Tukey's multiple comparison test. *=$p<0.05$; =$p<0.01$; *=$p<0.001$.

FIG. 10 shows clinical chemistry parameters where statistically significant changes were observed for the tumor-bearing mice at D1 and D4 post-dose. At D1 post-dose, the only statistically significant change in clinical chemistry was a reduction in Bilirubin—conjugated, observed with both the PMEL+IL15-Fc and with the Deep IL-15 Primed PMEL group ($p<0.05$ compared to vehicle control for both). At D4 post-dose, statistically significant increases in Albumin ($p<0.05$ compared to vehicle control), Total Protein ($p<0.01$ compared to vehicle control) and Bicarbonate TCO2 ($p<0.05$ compared to vehicle control) were seen with the PMEL group. Additionally, a statistically significant increase in Globulin was observed with the PMEL group ($p<0.001$ compared to vehicle control; and $p<0.05$ compared to DP-15 PMEL) and with the PMEL+IL15-Fc group ($p<0.05$ compared to vehicle control).

Systemic Cytokine Release

Figure 11:
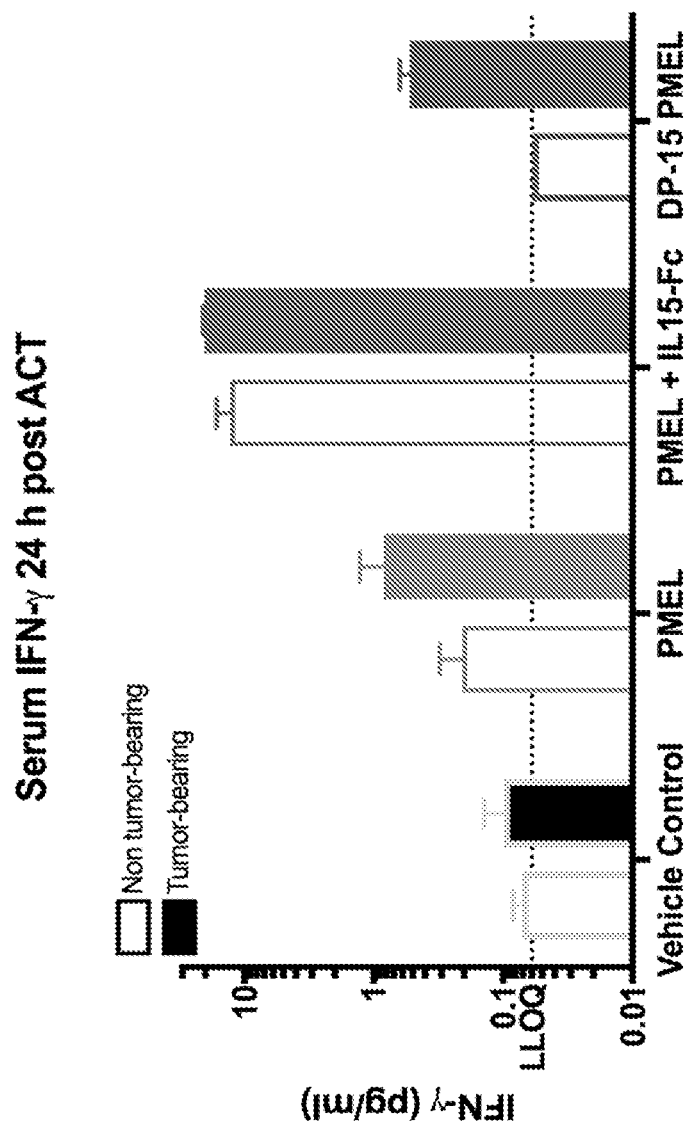
FIG. 11: Serum levels of IFN-γ in tumor-bearing compared to naïve mice 24 hr after ACT. The serum levels of IFN-γ in the PMEL+IL15-Fc group were significantly increased (2-way ANOVA with Tukey's multiple comparison, $p<0.001$) compared to both the PMEL and DP-15 PMEL groups in both naïve and tumor-bearing mice. ACT=adoptive cell transfer; DP-15 PMEL=Deep IL-15 Primed PMEL cells.

Using a Luminex 5-plex kit, serum cytokines (IFN-γ, IL-2, IL-4, IL-6, and TNFα) were measured at 2 hr, 24 hr and 96 hr post-dose. In the naïve non-tumor bearing mice, the levels of IFN-γ in the PMEL+IL15-Fc group were 12.8±3.7 μg/mL, while IFN-γ was below the lower limit of quantitation (LLOQ=0.06 pg/mL) in the Deep IL-15 Primed PMEL group (FIG. 11). In the tumor-bearing mice, there was on average a 41-fold higher IFN-γ concentration in the PMEL+IL15-Fc group (20.5±0.5 pg/mL) compared to the Deep IL-15 Primed PMEL group (0.5±0.1 pg/mL). Higher levels of IL-2, IL-6, and TNFα were also seen in the PMEL+IL15-Fc group compared to the other groups.

Pharmacokinetics of IL15-Fc in the Blood

A sandwich ELISA (anti-Fc capture antibody followed by anti-IL15 detection antibody) was used to measure IL15-Fc in the blood of mice injected with PMEL+IL15-Fc (10 μg) and Deep IL-15 Primed PMEL (carrying 58.5 ug of IL15-Fc).

The pharmacokinetics (PK) of a single dose administration of Deep IL-15 Primed PMEL and PMEL+IL15-Fc were determined for a composite animal in naïve and tumor-bearing mouse. For the PMEL+IL15-Fc group, maximum concentration (Cmax) was attained at 2 hr post dose administration in both naïve and tumor-bearing mice. In the Deep IL-15 Primed PMEL group, the first concentration measured was at 24 hr (the 2 hr samples were initially measured at a non-optimal dilution and no IL15-Fc was detected, and there was not sufficient sample available to repeat the measurement with ideal dilution). Tumor-bearing mice attained slightly lower concentrations than the naïve mice. The calculated mean t1/2 for IL15-Fc in the PMEL+IL15-Fc group was 28.9 hr and 7.12 hr in tumor bearing mice and non-tumor bearing mice, respectively.

Figure 12:
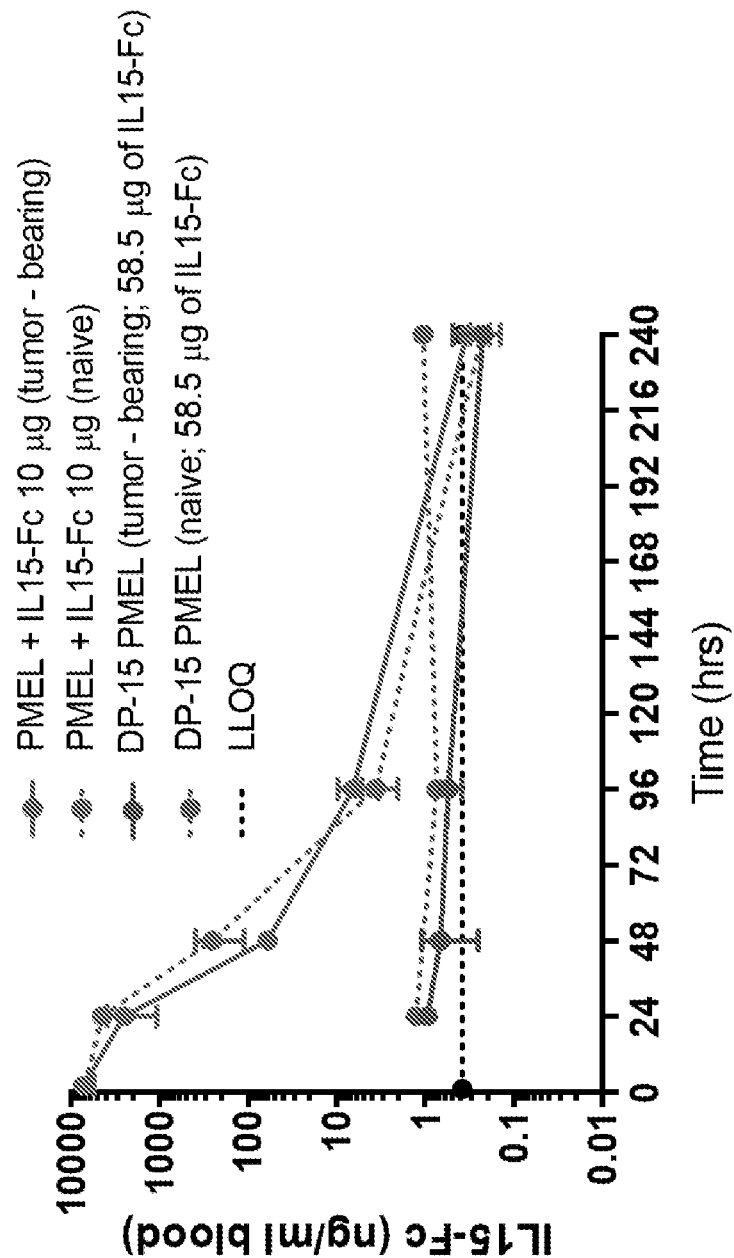
FIG. 12: IL15-Fc systemic exposure in mice treated with PMEL+IL15-Fc and Deep IL-15 Primed PMEL cells, in naïve and tumor-bearing mice.

The IL15-Fc concentrations at the 24 hr timepoint were compared between the PMEL+IL15-Fc and Deep IL-15 Primed PMEL groups. The total IL15-Fc concentration was higher in the PMEL+IL15-Fc (10 μg) group than in the Deep IL-15 Primed PMEL group (58.5 ug of IL15-Fc), approximately 3488-fold higher in the naïve mice and 3299-fold higher in the tumor bearing mice. Composite IL15-Fc PK parameters are summarized in Table 1 and the mean (SD) IL15-Fc PK profiles are depicted in FIG. 12.

TABLE 1

Composite IL15-Fc PK parameters for the PMEL + IL15-Fc group, in naïve and tumor - bearing mice (10 ug dose of IL15-Fc)

| Animal | Compound | Group | T1/2 (hr) | Cmax (ng/mL) | Tmax (hr) | Clast (ng/mL) | Tlast (hr) | AUClast (hr*ng/mL) | AUCINF (hr*ng/mL) |
|---|---|---|---|---|---|---|---|---|---|
| Composite | IL15-Fc | Non-tumor bearing | 7.12 | 6931 | 2 | 3.64 | 96 | 202387 | 202424 |
|  |  | Tumor Bearing | 28.9 | 7300 | 2 | 0.448 | 240 | 156335 | 156353 |

Inhibition of Tumor Growth

Figure 13:
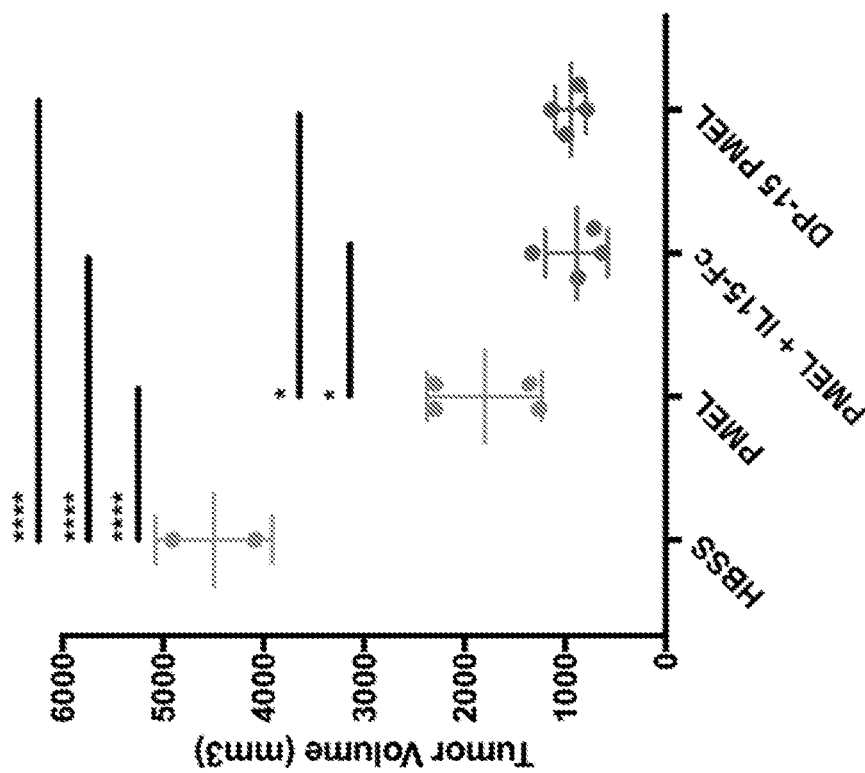
FIG. 13: Mean tumor volume over time and on Day 16. Tumor volumes were measured on D −5, Day −3, D0, D1, D2, D4, D6, D9, D10, D11, D14 and D16. Data are mean±SEM (left panel). Tumor volumes for individual animals on D16 are shown in the right panel. Statistical comparisons were made using ANOVA followed by Tukey's multiple comparison test. *=$p<0.05$; =$p<0.01$; *=$p<0.001$; ****=$p<0.0001$. The color of the asterisk represents which groups are statistically different. For example, a green asterisk over the grey (HBSS) line indicates that there is a significant difference between HBSS and PMEL cells. HBSS=vehicle control; ACT=adoptive cell transfer. DP-15 PMEL=Deep IL-15 Primed PMEL cells.
Figure 13:
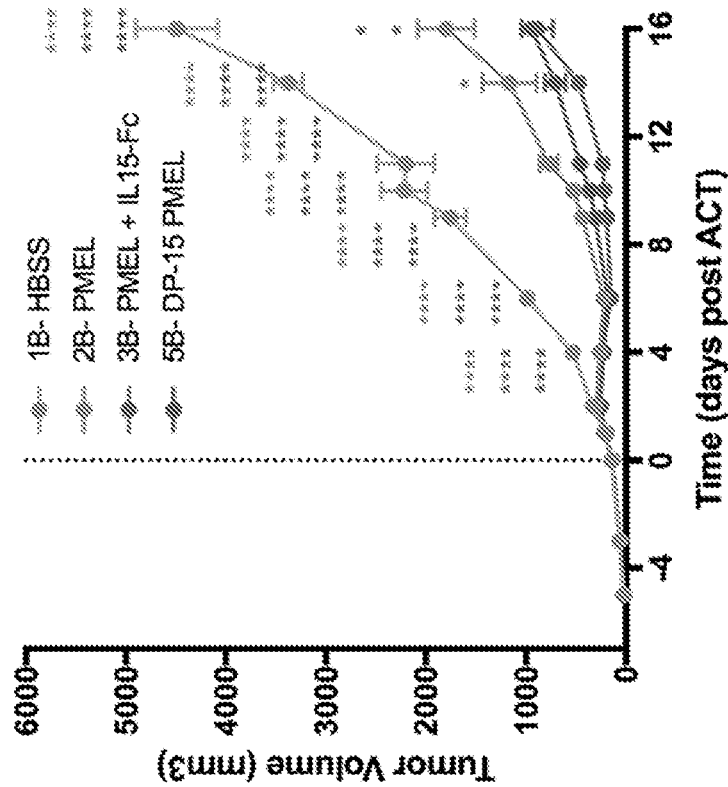
Figure 14:
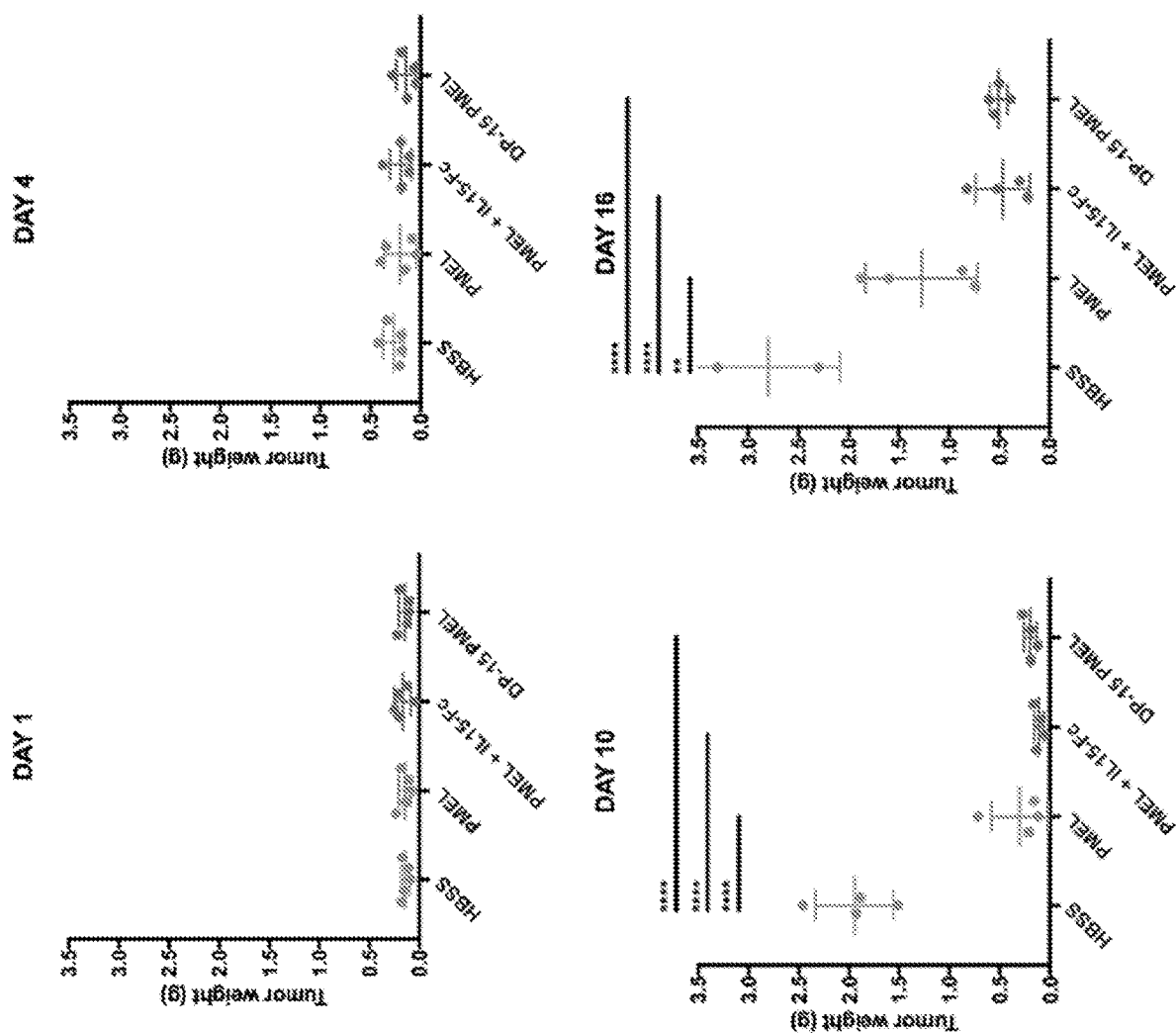
FIG. 14: Mean tumor weight at sacrifice (n=2-5/group/time point). Tumor weights were at sacrifice on Day 1, 4, 10 and 16 (n=2-5/group each time point). Statistical comparisons were made using ANOVA followed by Tukey's multiple comparison test. *=$p<0.05$; =$p<0.01$; **=$p<0.0001$. HBSS=vehicle control; DP-15 PMEL=Deep IL-15 Primed PMEL cells.

On D0 (the day of dosing) tumors had reached an average volume of approximately 140 mm$^3$. A statistically significant inhibition of tumor growth was observed at D4 post-dose in all treatment groups compared to vehicle control ($p<0.0001$), and this difference became more pronounced over time (FIG. 13, left panel). On study D16 there were only ⅖ animals remaining in the vehicle control group (the others were sacrificed due to extensive tumor burden) but ⅘ animals remaining in each of the treatment groups. Tumor volumes in the vehicle control group were significantly ($p<0.0001$) different from all other groups. Tumor volumes in the PMEL group were significantly ($p<0.05$) larger than those in the Deep IL-15 Primed PMEL and PMEL+IL15-Fc groups. The inhibition of tumor growth in the PMEL+IL15-Fc and Deep IL-15 Primed PMEL groups were not different from each other on D16 (FIG. 13, left and right panels). Tumors were weighed post-sacrifice (n=2-5, each group, each time point) on D1, 4, 10 and 16 post-dose. Tumor weights are shown in FIG. 14.

Some animals were found moribund or dead prior to the study-specified endpoints. These included mice in the vehicle control (4 total: 1 on D9, 1 on D10 and 2 on D14), in the PMEL group (2 total: 1 on D2, and 1 on D6), in the PMEL+IL15-Fc group (2 total: 1 on D9 and 1 on D11) and in the Deep IL-15 Primed PMEL group (2 total: 1 on D9 and 1 on D16). These were not considered related to treatment since they were distributed across groups with the highest numbers (n=4) in the vehicle control. Finally, there was no difference in animals found moribund or dead associated with the Deep IL-15 Primed PMEL group compared to PMEL.

Conclusions

Major findings of the study are summarized below.
1. Deep IL-15 Primed PMEL cells were well tolerated at the administered dose of 10×10$^6$ cells.
2. Both PMEL, PMEL+IL15-Fc and Deep IL-15 Primed PMEL cells resulted in tumor growth inhibition compared to vehicle control. Inhibition was higher with PMEL+IL15-Fc and Deep IL-15 Primed PMEL cells compared to PMEL.
3. No toxicologically relevant clinical chemistry parameter changes were observed with either PMEL or Deep IL-15 Primed PMEL cells. Some changes were observed with PMEL+IL-15 Fc.
4. No changes in serum IFN-γ, TNF-α or IL-6 were detected with PMEL or Deep IL-15 Primed PMEL cells at any time point. Significant changes in serum IFN-γ and TNF-α were observed with PMEL+IL15-Fc at 24 hr. IL-6 was increased with PMEL+IL15-Fc at 2 hr (Non-tumor-bearing (naïve) mice only) and 24 hr.
5. The serum levels of IL15-Fc in the Deep IL-15 Primed PMEL group were over 3000-fold lower compared to the levels detected in the PMEL+IL15-Fc group, corresponding to no weight loss, no significant changes in CBCs and in endogenous immune cells (CD8$^+$, NK1.1$^+$ and CD4$^+$ cells), reduced IFN-γ serum levels and associated pharmacological changes compared to the PMEL+IL15-Fc group.

Modifications and variations of the described methods and compositions of the present disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure are intended and understood by those skilled in the relevant field in which this disclosure resides to be within the scope of the disclosure as represented by the following claims.

INCORPORATION BY REFERENCE

All patents and publications mentioned in this specification are herein incorporated by reference to the same extent as if each independent patent and publication was specifically and individually indicated to be incorporated by reference.

The invention claimed is:

1. A therapeutic composition comprising:
   a protein cluster comprising a plurality of therapeutic protein monomers reversibly cross-linked to one another; and
   a pharmaceutically acceptable carrier or excipient,
   wherein the protein cluster has a size between 30 nm and 1000 nm in diameter measured by dynamic light scattering
   and is produced by reacting the plurality of therapeutic protein monomers with a plurality of biodegradable cross-linkers of formula (II):

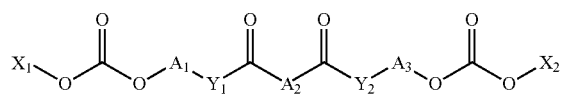

(II)

wherein:
   $X_1$ and $X_2$ are each independently selected from the group consisting of triflyl, tosyl, and N-succinimidyl;
   $A_1$ and $A_3$ are both —(CH$_2$)$_2$—;
   $A_2$ is —(CR$^1$R$^2$)m—;
   $Y_1$ and $Y_2$ are both O;

R¹ and R² at each occurrence are independently selected from the group consisting of hydrogen, halogen, hydroxyl, $C_{1-12}$ alkyl, $C_{2-12}$ alkenyl, $C_{3-12}$ cycloalkyl, $C_{2-12}$ heterocyclyl, $C_{6-12}$ aryl optionally substituted with 1 or more halo; hydroxyl; $C_{1-6}$ alkyl and/or $C_{1-6}$ alkoxyl, and $C_{4-12}$ heteroaryl optionally substituted with 1 or more halo; hydroxyl; $C_{1-6}$ alkyl and/or $C_{1-6}$ alkoxyl; and m is an integer selected from 0-12, thereby cross-linking the therapeutic protein monomers into the protein cluster, wherein the cross-linker portion of the protein cluster degrades, after administration into a subject in need thereof, under physiological conditions so as to release the therapeutic protein monomers from the protein cluster.

2. The therapeutic composition of claim 1, wherein the cross-linker is symmetrical.

3. The therapeutic composition of claim 1, wherein $X_1$ and $X_2$ are both N-succinimidyl.

4. The therapeutic composition of claim 1, wherein R¹ and R² are both hydrogen.

5. The therapeutic composition of claim 1, wherein $A_2$ is —$(CH_2)_2$—.

6. The therapeutic composition of claim 1, wherein the cross-linker is:

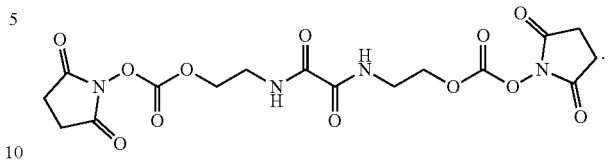

7. The therapeutic composition of claim 1, wherein $A_2$ is a bond.

8. The therapeutic composition of claim 1, wherein the therapeutic protein monomers comprise one or more cytokine molecules
selected from the group consisting of IL-15, IL-2, IL-7, IL-10, IL-12, IL-18, IL-21, IL-23, IL-4, IL-1α, IL-β, IL-5, IFNγ, TNFα, IFNα, IFNβ, GM-CSF, and GCSF.

9. The therapeutic composition of claim 1, further comprising a polycation on the surface of the protein cluster.

10. The therapeutic composition of claim 8, wherein the therapeutic protein monomers comprise IL-15.

* * * * *

UNITED STATES PATENT AND TRADEMARK OFFICE
CERTIFICATE OF CORRECTION

PATENT NO. : 11,524,033 B2  
APPLICATION NO. : 16/644647  
DATED : December 13, 2022  
INVENTOR(S) : Thomas L. Andresen Page 1 of 1

It is certified that error appears in the above-identified patent and that said Letters Patent is hereby corrected as shown below:

In the Claims

In Claim 6, at Column 38, Line 5, replace:

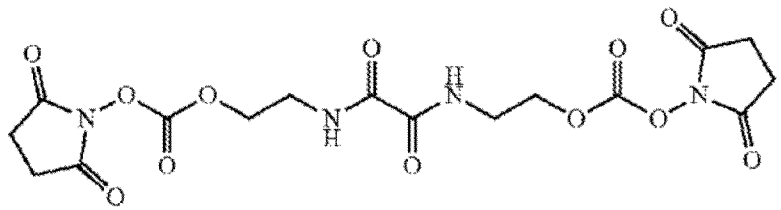

With:

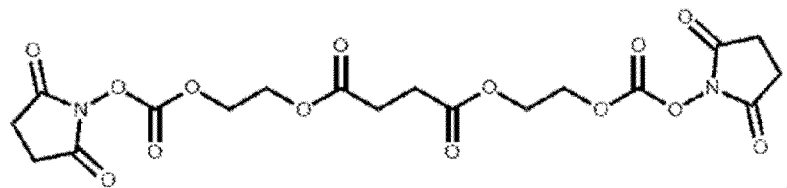

Signed and Sealed this  
Twenty-seventh Day of August, 2024

Katherine Kelly Vidal  
*Director of the United States Patent and Trademark Office*